(12) United States Patent
Canonne et al.

(10) Patent No.: US 8,092,661 B2
(45) Date of Patent: Jan. 10, 2012

(54) ELECTROPOLYMERISABLE MONOMERS, SOLUBLE IN AN AQUEOUS SOLUTION AND COMPRISING A METALLOPORPHYRIN

(75) Inventors: Frédéric Canonne, Buc (FR); Hafsa Korri-Youssoufi, Bruyeres le Chatel (FR); Jean-Pierre Mahy, Palaiseau (FR); Bernard Mandrand, Villeurbanne (FR); Martine Perree-Fauvet, Villebon sur Yvette (FR)

(73) Assignees: Biomerieux, Marcy l'Etoile (FR); Centre National de la Recherche Scientifique (CNRS), Paris Cedex (FR); Universite Paris SUD, Orsay Cedex (DE)

( * ) Notice: Subject to any disclaimer, the term of this patent is extended or adjusted under 35 U.S.C. 154(b) by 623 days.

(21) Appl. No.: 12/084,476

(22) PCT Filed: Nov. 2, 2006

(86) PCT No.: PCT/FR2006/051131
§ 371 (c)(1),
(2), (4) Date: Feb. 27, 2009

(87) PCT Pub. No.: WO2007/051947
PCT Pub. Date: May 10, 2007

(65) Prior Publication Data
US 2009/0314660 A1   Dec. 24, 2009

(30) Foreign Application Priority Data
Nov. 3, 2005 (FR) ..................................... 05 11187

(51) Int. Cl.
*G01N 27/26* (2006.01)
*G01N 27/327* (2006.01)

(52) U.S. Cl. .................. 204/403.01; 204/416; 204/418; 205/777.5; 205/792; 313/504; 526/241; 540/145; 540/465; 540/121; 534/11; 534/15; 514/183; 514/185; 514/63; 514/189; 514/740

(58) Field of Classification Search ............ 204/403.01, 204/416, 418; 313/504; 526/241; 540/145, 540/465, 121; 534/11, 15; 514/183, 185, 514/63, 189, 740; 205/777.5, 792
See application file for complete search history.

(56) References Cited

U.S. PATENT DOCUMENTS
6,004,530 A    12/1999  Sagner et al.
6,623,973 B2   9/2003   Levitsky et al.
7,663,301 B2 * 2/2010   Litz et al. ..................... 313/504

FOREIGN PATENT DOCUMENTS
| FR | 2607507 | 6/1988 |
| WO | 95/29199 | 11/1995 |
| WO | 00/31750 | 6/2000 |
| WO | 01/81446 | 11/2002 |
| WO | 2004/060904 | 7/2004 |

OTHER PUBLICATIONS

CAS Structure Search by EIC Library performed on Jun. 13, 2011.*
Wandrekar, Vinay, Trumble, Williams R. and Czuchajowski, Leszek, "Interactions of Porphyrinyl-Nucleosides with DNA using the example of Porphyrinyl-Thymidine" (1996) *Journal of Heterocylic Chemistry*, vol. 33, 1775-1783.
Millan, Kelly M. and Mikkelsen, Susan R., "Sequence-Selective Biosensor for DNA Based on Electroactive Hybridization Indicators" (1993) *Analytical Chemistry*, vol. 65, 2317-2323.
Rodriguez, Marisol and Bard, Allen J., "Electrochemical Studies of the Interaction of Metal Chelates with DNA. 4. Voltammetric and Electogenerated Chemiluminescent Studies of the Interaction of Tris (2,2'-bipyridine)osmium(II) with DNA" (1990) *Analytical Chemistry*, vol. 62(24), 2658-2662.
Bedioui, Fethi, Moisy, Philippe, and Devynck, Jacques, "Poly(Pyrrole Manganese Porphyrin) Film Electrode as a Catalyst in Electroassisted Oxidation Reactions using Molecular Oxygen: Comparison with Described Homogeneous Systems" (1989) *Journal of Molecular Catalysis*, vol. 56, 267-275.
Garnier, Francis, Korri-Youssoufi, Hafsa, Srivastava, Pratima, Mandrand, Bernard, Delair, Thierry, "Toward Intelligent Polymers: DNA sensors based on oligonucleotide-functionalized polypyrroles" (1999), Synthetic Metals, vol. 100, 89-94.
Korri-Youssoufi, H. and Vassar, A., "Electrochemical Probing of DNA Based on Oligonucleotide-Functionalized Polypyrrole" (2001), *Biomacromolecules*, vol. 2(1), 58-64.
Sadki, Saïd, Schottland, Philippe, Brodie, Nancy, and Sabouraud, Guillaume, "The Mechanisms of Pyrrole Electropolymerization" (2000), *The Royal Society of Chemistry*, vol. 29, 283-293.
Egholm, Michael, Buchardt, Ole, Nielsen, Pter E., and Berg, Rolf H., "Peptide Nucleic Acids (PNA). Oligonucleotide Analogues with an Achiral Peoptide Backbone" *American Chemical Society*, vol. 114(5), 1895-1897.
Fleischer, Everly B., Palmer Joan M., Srivastava, T.S., and Chatterjee, A., "Thermodynamic and Kinetic Properties of an Iron-Porphyrin System" (1971), *Journal of the American Chemical Society*, vol. 93(13), 3162-31667. Ye, Bao-Hui and Naruta, Yosinori, "A novel method for the synthesis of regiospecifcally sulfonated porphyrin monomers and dimmers" (2003), *Tetrahedron*, vol. 59, 3593-3601.
Massari, Aaron M., Gurney, Richard W., Wightman, Matt D., Kane Huang, Chien-Hao, Nguyen, SonBinh T., Hupp, Joseph T., "Ultrathin micropatterned porphyrin films assembled via zirconium phosphonate chemistry" (2003), *Polyhedron*, vol. 22, 3065-3072.
Kachadourian, Remy, Flaherty, Meghan M., Crumbliss, Alvin L., Patel, Manisha, Day, Brain J., "Synthesis and in virtro properties of manganese (III) β-octabromo-*meso*-tetrakis (4-carboxyphenyl)porphyrin" (2003), *Journal of Inorganic Biochemistry*, vol. 95, 240-248.
Little, Robert G., Anton, John A., Loach, Paul A., Ibers, James A., "The Synthesis of Some Substituted Tetraarylporphyrins" (1975), *Heterocylic Chemistry*, vol. 12, 343-349.

(Continued)

*Primary Examiner* — Bruce Bell
(74) *Attorney, Agent, or Firm* — Clark & Brody

(57) ABSTRACT

The invention relates to novel electropolymerisable monomers which are to be polymerised in an aqueous solution and comprise: an electropolymerisable pattern selected from acetylene, pyrrols, thiophenes, indols, anilines, azines, p-phenylene vinylenes, p-phenylenes, pyrenes, furanes, selenophenes, pyrridazines, carbazoles, acrylates, methacrylates and the derivatives thereof, and a metalloporphyrine which is substituted by at least two ionised or ionizable entities in an aqueous solution. The invention also relates to a method for the polymerization of such monomers, to the electroactive probe that can be obtained by the polymerization of such monomers, and to a method for detecting a target ligand in a biological sample using one such electroactive probe.

49 Claims, 5 Drawing Sheets

OTHER PUBLICATIONS

Figure 1:
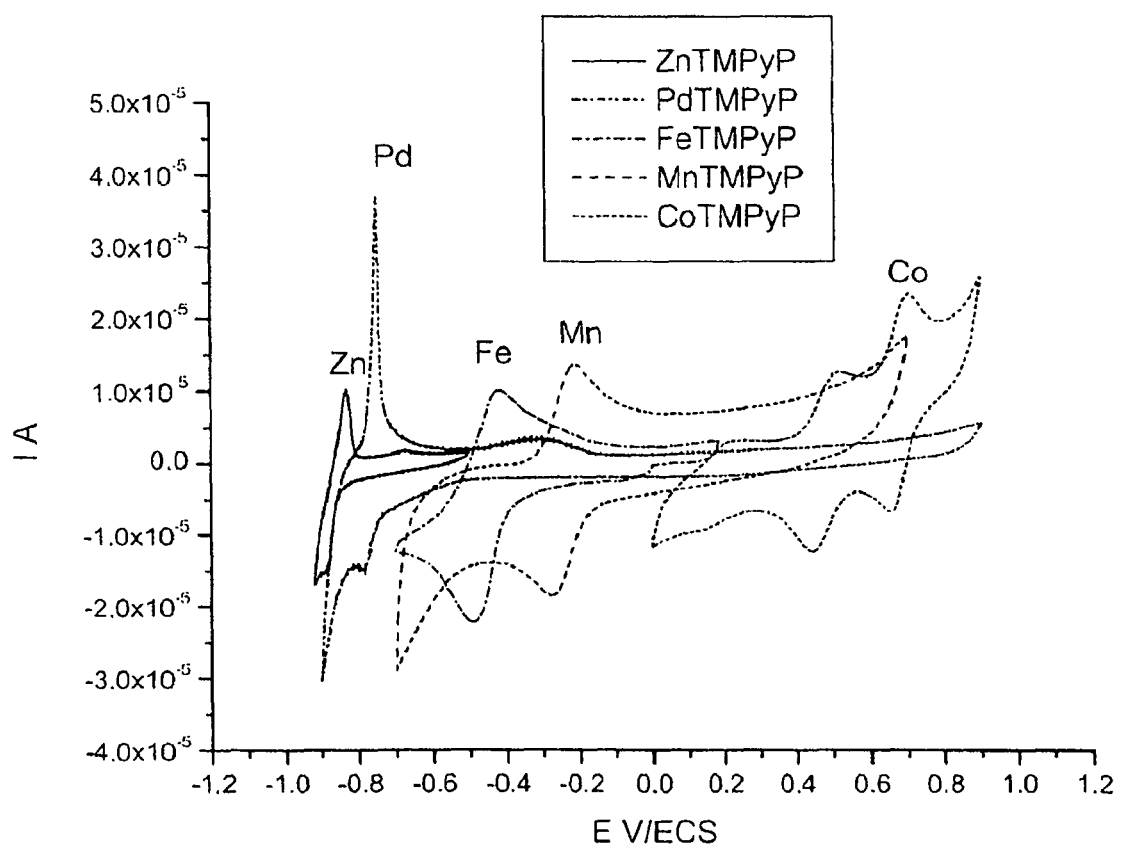

Adler, Alan D., Longo, Frederick R., Finarelli, John D., Goldmacher, Joel, Assour, Jacques, and Korsakoff, Leonard, "A Simplified Synthesis for *meso*-Tetraphenylporphin" (1966), Journal of Organic Chemistry, (1967), *Journal of Organic Chemistry*, vol. 32, 476.

Littler, Benjamin J., miller, Mark A., Hung, Chen-Hsiung, Wagner, Richard W., O'Shea, Donal F., Boyle, Paul D., and Lindsey, Jonathan S., "Refined Synthesis of 5-Substituted Dipyrromethanes" (1999), *Journal of Organic Chemistry*, vol. 64(4), 1391-1396.

Laha, Joydev K., Dhanalekshmi, Savithri, Taniguchi, Masahiko, Ambroise, Arounaguiry, and Lindsey, Jonathan S., "A Scalable Synthesis of Meso-Substituted Dipyrromethanes" (2003), Organic Process Research and Development, vol. 7(6), 799-812.

Gryko, Daniel T. and Tasior, Mariusz, "Simple route to meso-substituted trans-A2-B2-porphyrins bearing pyridyl units" (2003), Tetrahedron Letters, vol. 44, 3317-3321.

Rao, Polisetti Dharma, Dhanalekshmi, Savithri, Littler, Benjamin J., and Lindsey, Jonathan S., "Rational Syntheses of Porphyrins Bearing up to Four Different Meso Substituents" (2000).

Yan, Hao, "Nucleic Acid Nanotechnology" (2004), *Science*, vol. 306, 2048-2074.

Gobbi, Silvia, Rampa, Angela, Bisi, Alessandra, Belluti, Federica, Caputo, Anna, Zampiron, Antonella, and Carrara, Maria, "Synthesis and Antitumor Activity of New Derivatives of Xanthen-9-one-4-acetic Acid" (2002), *Journal of Medicinal Chemistry*, vol. 45(22), 4931-4939.

Cignarella, Giorgio, Barlocco, Daniela, Rossi, Guendalina, Rossi, Elisabetta, "Spirocyclopropane Carboxylic Acids Derived from 1-Tetralone and 4-Chromanone and their Conversion to the Corresponding Pyridazinones" (1990), *Synthesis*, 160-162.

Fürstner, Alois, Stelzer, Frank, Rumbo, Antonio, and Krause, Helga, "Total Sythesis of the Turrianes and Evaluation of their DNA-Cleaving Properties" (2002) *Journal of European Chemistry*, vol. 8(8), 1856-1871.

Ka, Jae-Won and Lee, Chang-Hee, "Optimizing the synthesis of 5,10-disubstituted tripyrromethanes" (2000), *Tetrahedron Letters*, vol. 41, 4609-4613.

Gryko, Dorota and Lindsey, Jonathan S., "Rational Sythesis of Meso-Substituted Porphyrins Bearing One Nitrogen Heterocyclic Group" (2000), *Journal of Organic Chemistry*, vol. 65(7), 2249-2252.

Littler, Bnjamin J., Miller, Mark A., Hung, Chen-Hsiung, Wagner, Richard W., O'Shea, Donal F., Boyle, Paul D., and Lindsey S. Jonathan, "Refined Synthesis of 5-Substituted Dipyrromethanes" (1999), *Journal of Organic Chemistry*, vol. 64(4), 1391-1396.

Rao, Polisetti Dharma, Dhanalekshmi, Savithri, Littler, Benjamin J., Lindsey, Jonathan S., "Rational Sytheses of Porphyrins Bearing up to Four Different Meso Substituents" (2000), *Journal of Organic Chemistry*, vol. 65(22), 7323-7344.

Laha, Joydev K., Dhanalekshmi, Savithri, Taniguchi, Masahiko, Ambroise, Arounaguiry, and Lindsey, Jonathan S., "A Scalable Synthesis of Meso-Substituted Dipyrromethanes" (2003), *Organic Process Research and Development*, vol. 7(6), 799-812.

Hunt, S., "Degradation of Amino Acids Accompanying in vitro Protein Hydrolysis" *Chemistry and Biochemistry of the Amino Acids*, Chapter 12, 376-398.

\* cited by examiner

ELECTROPOLYMERISABLE MONOMERS, SOLUBLE IN AN AQUEOUS SOLUTION AND COMPRISING A METALLOPORPHYRIN

The present invention relates the technical area of electropolymerisation. In particular, the subject of the invention is a novel, electropolymerizable monomer soluble in an aqueous solution and comprising a metalloporphyrin. The invention also relates to a method to polymerize said monomer, to the electroactive probe able to be obtained by polymerizing said monomer, and to a method to detect a target ligand in a biological sample using said electroactive probe.

The detection of biomolecules, such as proteins or nucleic acid sequences has undergone swift technological development in recent years, notably in the medical area. It has become possible for example to detect very small quantities of DNA through the development of DNA amplification methods, such as Polymerase Chain Reaction—PCR. The DNA of the infectious agent or of cells being examined is first isolated, then amplified using a PCR-type technique and finally the presence of absence of DNA is detected and quantified.

The development of new devices to detect biomolecules, based on real-time reading of detection with improvement sensitivity, improved specificity and at lesser cost is undergoing full expansion.

At the present time, the transducers generally used for detection are fluorescent detectors. This method is based on optical reading, namely measurement of light absorbed or emitted subsequent to a chemical or biochemical reaction. It is therefore an indirect method. Numerous compounds have fluorescence properties, in particular metalloporphyrins which are widely used in this context. Document U.S. Pat. No. 6,623,973 describes a method to detect volatile organic compounds through fluorescence change in porphyrin films. Wandrekar et al describe the interactions of the compound meso-tri(N-methyl-4-pyridinium)porphyrinyl-p-phenylene-5'O-thymidine) with a DNA molecule (J. Heterocyclic Chem., 1996, 33, 1775-1783). Document U.S. Pat. No. 6,004,530 describes a method to prepare a metalloporphyrin derivative coupled with biomolecules allowing fluorescence detection of proteins or oligonucleotides.

The major drawbacks of these indirect methods is their low sensitivity and specificity.

Direct detection techniques have been developed, such as electrochemical detection. This technique offers fast, specific detection of biomolecules. The high sensitivity of electrochemical transducers, their compatibility with micro-fabrication techniques and miniaturization technology, their low cost and minimum maintenance, means that these devices are important for diagnosis. Additionally, electrochemistry offers the sole pathway for electrical control over DNA hybridization in various denaturing processes, and more generally to detect the specific interaction of DNA with various molecules to produce an electric signal.

Several modes of electrochemical detection exist, such as coulemetric and potentiometric detection or detection by impedance measurement.

Electrochemical sensors based on the use of electroactive intercalators have been widely described in the literature (Millan et al, Anal. Chem., 1993, 65, 2317; Bard et al Anal. Chem., 1990, 62, 2658). The probe-target duplex formed after hybridization is exposed to an intercalator solution. The increase in electrochemical response due to the association of intercalator with the surface of the duplex acts as hybridization signal. Most of these biosensors use metal cation complexes such as $Co(phen)_3^{3+}$, $Co(bpy)_3^{3+}$ or daunomycin. The low specificity of these intercalators with respect to hybridization means that the selectivity of this method is very limited.

Other electrochemical sensors use an electrodonor group such as ferrocene as electrochemical probe. Document WO 01/81446 describes an electroactive polymer whose pyrrole unit carries a polynucleotide bound to ferrocene. Bedioui et al describe a film of poly(pyrrole-manganese porphyrin) used in a catalytic system (Journal of Molecular Catalysis, 1989, 56, 267-275). In these structures, the monomers used are hydrophobic and electropolymerisation is generally conducted in an organic solvent. However manipulations in an organic medium are not compatible with the use of biomolecules. Biomolecules are not soluble in such media and/or often become denatured therein and their properties are deteriorated. Regarding proteins, loss of active conformation is most often ascertained.

From this finding, two strategies have emerged up until now: the first, on a chip with electrodes, consists of forming several layers of conductor polymers which, starting from the electrode, comprise a polypyrrole layer (deposited in an organic solvent), a copolymer layer of pyrrole/pyrrole-electrodonor group (deposited in an organic solvent) and finally a copolymer layer of pyrrole/pyrrole covalently bound to a biomolecule (deposited in an aqueous medium). This so-called <<multi-layer>> strategy is described for example in FR 2849038. Polymers which may be used for this strategy are described in WO 95/29199 for example and in WO 01/81446. This <<multi-layer>> strategy is not fully satisfactory since it is time-consuming owing to the use of several organic solvent/aqueous medium transitions, with the need at each time for several rinse operations of the chip.

The other strategy is called post-functionalization: it consists of post-polymerization, covalent fixing of biomolecules, in an aqueous medium, using reactive functions located on the polymer layer. Reference may particularly be made to Synthetic Metals 1999, 89-94 and to Biomacromolecules 2001, 2, 58-64. This post-functionalization strategy does not allow biomolecule addressing. Additionally, it lacks pad-to-pad reproducibility owing to variable coupling efficacy of the biomolecule on the polymer.

The development is therefore still awaited of polymers having improved electroactive properties and compatible with an electropolymerisation reaction in an aqueous solution.

To overcome the drawbacks of the prior art the present invention proposes a monomer intended to be polymerized in an aqueous solution which comprises:
  an electropolymerizable unit chosen from among acetylene, pyrroles, thiophenes, indoles, anilins, azines, p-phenylenevinylenes, p-phenylenes, pyrenes, furans, selenophenes, pyrridazines, carbazoles, acrylates, methacrylates and their derivatives, and
  a metalloporphyrin substituted by at least two entities ionized or ionizable in an aqueous solution.

Advantageously, the electropolymerizable monomer such as defined above has any one of the characteristics given below, or several of the following characteristics when they are not exclusive of each other:
  the metalloporphyrin is substituted by three entities ionized or ionizable in an aqueous solution,
  the monomer is soluble in distilled water, at least up to a concentration of 10 mM, preferably at least up to a concentration of 30 mM,
  the metalloporphyrin is substituted by at least two entities ionized or ionizable in an aqueous solution, that are located at a meso position of the metalloporphyrin.

the ionized or ionizable entities comprise a function ionized or ionizable in an aqueous solution which has a pH of between 3 and 8, chosen from among the functions: ammonium, amine, polyamine, carboxylic acid, phosphonic acid, sulfonic acid and phosphate, two of the ionized or ionizable entities substituting the metalloporphyrin comprise an N-methylpyridinium group in the form of a salt or —COOH function, two of the ionized or ionizable entities substituting the metalloporphyrin are identical, the metalloporphyrin is substituted by at least two different entities ionized or ionizable in an aqueous solution, the metalloporphyrin, and in particular one of its meso positions, is substituted by a biological ligand, advantageously chosen from among the polynucleotides, in particular oligonucleotides, polypeptides, proteins, antigens, antibodies, haptenes, oligosaccharides and biotin, polynucleotides being preferred, the link between the electropolymerizable unit and the metalloporphyrin is made at the meso position of the metalloporphyrin, the link between the electropolymerizable unit and the metalloporphyrin is made via a spacer arm, the electropolymerizable unit is a pyrrole; preferably the link between the pyrrole and the metalloporphyrin is ensured at position 3 of the pyrrole, the metalloporphyrin is also substituted by one or more electron donor or attractor groups, preferably chosen from among: halogen atoms, cyano, nitro, $(C_1-C_4)$alkyl, $(C_1-C_4)$alkenyl, $(C_1-C_4)$alkynyl and $(C_1-C_4)$alkoxy groups, the metal of the metalloporphyrin is a transition metal (defined in Mendeleïev's table, version July 2005), or Mg, Al, Sn or Ge, and is preferably chosen from among: Co, Ni, Mg, Fe, Zn, Mn, Pd, Cu, Pt, V, Mo, Al, Sn and Ge, and preferably from among: Co, Zn and Mn;

the monomer does not comprise any biological ligand.

The monomers of the invention, through the presence of at least two entities ionized or ionizable in an aqueous solution, will be soluble in an aqueous solution thereby allowing their polymerization in said aqueous media.

Before describing the invention in more detail, some terms used in the description and claims are defined below.

By <<electropolymerizable monomer>> is meant a monomer comprising an electropolymerizable unit, said monomer being capable of reacting by electrochemical polymerization with other monomers to form a polymer. An electropolymerizable structure has alternate single and double bonds. In particular, under the invention, as electropolymerizable unit, use is made of pyrrole, acetylene, thiophene, azine, p-phenylene, p-phenylene vinylene, pyrene, furane, selenophene, pyridazine, carbazole, aniline, indole, acrylate, methacrylates and their derivatives.

By <<entity>> or <<group>> <<ionizable in an aqueous solution>> is meant a hydrophilic chemical group able to form a cation or anion in an aqueous solution. The ionized form in an aqueous solution is obtained without conducting a chemical reaction of hydrolysis or degradation type. The ionized form is obtained, for example, by proton exchange or in the form of a pair of ions in solution from a salt. Said ionized or ionizable entities particularly contain an ammonium group, an amine (—NHR" in which R" is a hydrogen atom or a $(C_1-C_4)$alkyl) group, a polyamine, carboxylic acid (—COOH), phosphonic acid (—OP(OH)$_2$), sulfonic acid (—SO$_3$H), phosphate (—O—P(O)$_2$(OR") in which R" is a hydrogen atom or a $(C_1-C_4)$alkyl) group. An ionizable entity lies in an ionic form when it is placed in an aqueous solution which has a pH of between 3 and 8, preferably between 5 and 8. Advantageously, the ionizable entity is in ionized form in distilled water.

Under the invention, by <<alkyl>> is meant a straight or branched hydrocarbon group having 1 to 15 carbon atoms and preferably 1 to 10 carbon atoms. A $(C_1-C_4)$alkyl group designates an alkyl group comprising 1 to 4 carbon atoms. Examples of $(C_1-C_4)$alkyl groups are methyl, ethyl, propyl, isopropyl, butyl, isobutyl, t-butyl groups.

By <<alkenyl>> is meant a hydrocarbon group, straight or branched, having 1 to 15 carbon atoms and preferably 1 to 10 carbon atoms and comprising one or more double bonds preferably 1 or 2 double bonds.

By <<alkynyl>> is meant a straight or branched hydrocarbon group having 1 to 15 carbon atoms and preferably 1 to 10 carbon atoms and comprising one or more triple bonds preferably 1 or 2 triple bonds.

By <<alcoxy>> is meant an —O-alkyl group, alkyl being defined as above.

By ammonium group is meant a quaternary amine in salt form such as N-methylpyridinium. The N-methylpyridinium group preferably corresponds to:

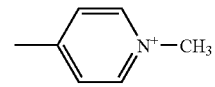

By <<halogen atom>> is meant a chlorine, bromine, fluorine or iodine atom.

When it is indicated that an integer is contained in the range of 1 to 3 for example, this means that this integer can be 1, 2 or 3.

By <<monomer soluble in an aqueous solution>> is meant a monomer soluble in an aqueous solution under polymerization conditions, namely conditions of temperature, pH and ionic strength used for a polymerization reaction via electrochemical route. Electropolymerisation is generally conducted in an aqueous solution whose pH lies between 3 and 8 and at a temperature in the order of 20 to 30° C. Preferably the solubility of a monomer of the invention is such that the addition of said monomer to distilled water at a temperature of 25° C. at least up to a concentration of 1 mM, preferably at least up a concentration of 10 mM, and further preferably at least up to a concentration of 30 mM, leads to a homogeneous solution transparent to the naked eye with no precipitation.

By <<polymerization>> is meant a reaction by chemical or electrochemical route of units of same chemical type allowing the assembly of a certain number of monomers to form a polymer (r×M→(M)$_r$ in which r is equal to or greater than 2. <<Polymerization>> encompasses copolymerization and homopolymerization. Under the invention it advantageously concerns the condensing of pyrrole units to form a polypyrrole. By copolymerization is meant the simultaneous polymerization of different units. The terms <<electropolymerisation>>, <<electrochemical copolymerization>> and <<electrochemical polymerization>> designate polymerization by electrochemistry. The electropolymerisation/electrocopolymerization step is performed using techniques well known to persons skilled in the art. For example it may be conducted by subjecting the monomers to sufficient scans of electric potential to cause polymerization by oxidation or polymerization by controlled current (chronopotentiometry) or by controlled potential (chronoamperometry). In one particular embodiment of the invention, polymerization is performed by chronoamperometry deposit or controlled potential deposit. This method consists of stepping a potential from equilibrium potential (zero current) up to a fixed value at which the reaction takes place at the electrode, and of measuring the current in relation to time.

The <<polymerization conditions>> designate pH, temperature and ionic strength of the aqueous solution used for polymerization. Regarding pyrrole, electropolymerisation is carried out via the Diaz mechanism (Sadki et al, Chem. Soc. Rev., 29: 283-293, 2000) which leads to the formation of polypyrrole. This polymerization occurs at positions 2 and 5 of the pyrrole monomers. A pyrrole substituted at position 3 or 4 of the pyrrole core is therefore able to polymerize or copolymerize with other pyrroles at positions 2 and 5. The pyrrole units substituted at position 3 are preferred.

By <<conductor polymer>> is meant a polymer whose electrons are highly delocalized, most often along a chain of simple and double bonds (conjugate bonds), causing it to behave like a semiconductor or conductor.

By biological ligand is meant a compound which has at least one recognition site enabling it to react with a target molecule of biological interest. A ligand/anti-ligand pair able to interact specifically to form a conjugate is also called a probe ligand/target ligand in the present invention.

As examples of biological ligands, mention may be made of polynucleotides and in particular of oligonucleotides, antigens, antibodies, polypeptides, proteins, haptenes, oligosaccharides and biotin . . . . It therefore appears that most of these biological ligands comprise a function that is ionizable in an aqueous solution. In the meaning of the invention, the term <<biological ligands>> and the terms <<polynucleotides>>, <<oligonucleotides>>, <<antigens>>, <<antibodies>>, <<polypeptides>>, <<proteins>>, <<haptenes>>, <<oligosaccharides>> and <<biotin>> may include a linker arm attached to the biological ligand under consideration and linking it with the metalloporphyrin. These linker arms may in particular include a —NH—CO— or —CO—NH-chain resulting from coupling of an amine or acid function, optionally in activated form, carried by the metalloporphyrin, with a reactive function carried by the biological ligand.

The term <<polynucleotide>> designates a chain of at least 2 nucleotides (deoxyribonucleotides or ribonucleotides), natural or modified, able to hybridize under suitable hybridization conditions with an, at least partly complementary oligonucleotide. By modified nucleotides is meant for example a nucleotide comprising a modified base and/or comprising a modification at the internucleotide linkage and/or at the backbone. As example of modified bases mention may be made of inosine, methyl-5-deoxycytidine, dimethylamino-5-deoxyuridine, diamino-2,6-purine and bromo-5-deoxyuridine. To illustrate a modified internucleotide linkage, mention may be made of phosphorothioate, H-phosphonate and alkyl-phosphonate linkages. The alpha-oligonucleotides such as those described in FR-A-62 607 507 and the PNAs subject of the article by M. Eghom et al, J. Am. Chem. Soc (1992) 114, 1895-1897 are examples of polynucleotides consisting of nucleotides whose backbone has been modified. Each of these modifications can be taken in combination. The polynucleotide can be an oligonucleotide, a natural nucleic acid or its fragment such as a DNA, ribosomic RNA, messenger RNA, transfer RNA, a nucleic acid obtained by an enzymatic amplification technique.

The term <<polypeptide>> particularly means any chain of at least two amino acids. By amino acids is meant the primary amino acids encoding proteins, derived amino acids after enzymatic action such as trans-4-hydroxyproline and natural amino acids not present in proteins such as norvaline, N-methyl-L leucine, staline (see Hunt S. in Chemistry and Biochemistry of the amino acids, Barett G. C. ed., Chapman and Hall, London 1985), the amino acids protected by chemical functions which can be used for synthesis on a solid carrier or in liquid phase, and non-natural amino acids. The term <<protein>> includes holoproteins and heteroproteins such as nucleoproteins, lipoproteins, phosphoproteins, metalloproteins and glycoproteins, both fibrous as globular in their characteristic conformational form.

The term <<haptene>> designates non-immunogenic compounds i.e. incapable themselves of causing an immune reaction by the production of antibodies, but capable of being recognized by antibodies obtained by immunizing animals under known conditions, in particular by immunization with a conjugate hapto-protein. These compounds generally have a molecular weight of less than 3000 Da, and most often less than 2000 Da, and can for example be glycosylated peptides, metabolites, vitamins, hormones, prostaglandins, toxins, antibiotics or various medicinal products, nucleosides and nucleotides.

The term <<antibody>> includes polyclonal or monoclonal antibodies, antibodies obtained by genetic recombination, and fragments of antibodies such as Fa or F(ab')2 or Fc fragments, and any antibody obtained by genetic modification or recombination. The term <<antigen>> designates a compound able to be recognized by an antibody whose synthesis it has induced by an immune response.

According to another of its aspects, the subject of the invention is monomers of formula (I) comprising a pyrrole unit and a metalloporphyrin:

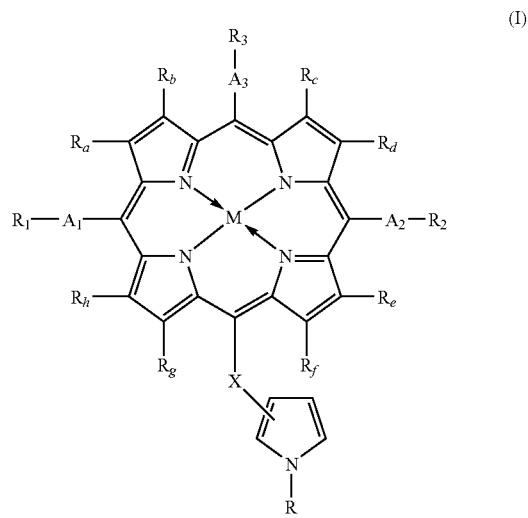

(I)

in which:
the groups $R_1$, $R_2$ and $R_3$, each independently of each other, represent a hydrogen atom, an ionized or ionizable group in an aqueous solution, or a biological ligand, on the understanding that at least two of groups $R_1$, $R_2$ and $R_3$, the same or different, are an ionized or ionizable group, $A_1$, $A_2$ and $A_3$, each independently of each other, represent a spacer arm, particularly chosen from among the following chains:

—$(CH_2)_{n1}$— in which n1 is an integer lying in a range from 0 to 5,

—(CH$_2$—CH$_2$—O)$_{n2}$— in which n2 is an integer lying in a range from 1 to 5,

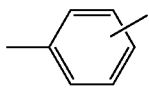 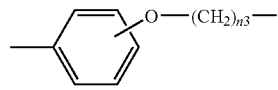

in which n3 is an integer ranging from 1 to 5,

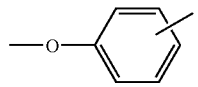

the groups R$_a$, R$_b$, R$_c$, R$_d$, R$_e$, R or R$_f$, R$_g$ and R$_h$, each independently of one another, represent a hydrogen atom, an electron donor group or an electron attractor group, X is a spacer arm, chosen in particular from among the following chains:
  —(CH$_2$)$_{m1}$— in which m1 is an integer lying in the range of 1 to 6,

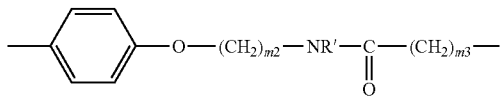

in which m2 and m3, each independently of one another are an integer lying between 1 and 3 and R' is a hydrogen atom or a (C$_1$-C$_4$)alkyl group,
  —C═(CH$_2$—CH$_2$—O)$_{m4}$— in which m4 is an integer lying in the range of 1 to 3,
  a polypeptide chain comprising 1 to 3 amino acids,
  —(CH═CH)$_{m5}$— in which m5 is an integer lying in the range of 1 to 3, M is a transition metal or Mg, Al, Sn or Ge, and
R is a hydrogen atom or a methyl, ethyl or methoxy group.

Advantageously, the monomers of formula (I) have one or more of the following characteristics, when they are not exclusive of one another:
  at least two of the groups R$_1$, R$_2$ and R$_3$ each independently comprise or are an ionized or ionizable function in an aqueous solution having a pH of between 5 and 8, chosen from among the functions: ammonium, amine, polyamine, carboxylic acid, phosphonic acid, sulfonic acid and phosphate,
  only one of the groups R$_1$, R$_2$ and R$_3$, preferably R$_3$, is a biological ligand chosen from among the polynucleotides, in particular oligonucleotides, polypeptides, proteins, antigens, antibodies, haptens, oligosaccharides and biotin,
  at least one of the groups R$_1$, R$_2$ and R$_3$ is an N-methylpyridinium in salt form or —COOH form,
  -A$_1$-R$_1$=-A$_2$-R$_2$ and preferably -A$_1$-R$_1$=-A$_2$-R$_2$═N-methylpyridinium in salt form or:

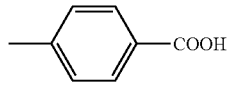

-A$_3$-R$_3$ is a group:

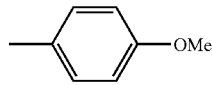

-A$_1$-R$_1$=-A$_2$-R$_2$=-A$_3$-R$_3$ and, preferably, -A$_1$-R$_1$=-A$_2$-R$_2$=-A$_3$-R$_3$═N-methylpyridinium in salt form,
  the linkage between the pyrrole and the metalloporphyrin is ensured at position 3 of the pyrrole,
  R is a hydrogen atom,
  R$_a$═R$_b$═R$_c$═R$_d$═R$_e$═R$_f$═R$_g$═R$_h$═H,
  at least one of groups R$_a$, R$_b$, R$_c$, R$_d$, R$_e$, R$_f$, R$_g$ and R$_h$ is an electron donor or attractor group chosen from among: halogen atoms, cyano, nitro, (C$_1$-C$_4$)alkyl, (C$_1$-C$_4$)alkenyl, (C$_1$-C$_4$)alkynyl and (C$_1$-C$_4$)alkoxy groups,
  the metal of the metalloporphyrin is chosen from among Co, Ni, Mg, Fe, Zn, Mn, Pd, Cu, Pt, V, Mo, Al, Sn and Ge and preferably among: Co, Zn and Mn,
  the monomer does not contain any biological ligand,
  X is a group:

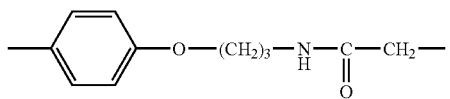

The ionizable entities present on the metalloporphyrin allow a monomer to be obtained that is soluble in an aqueous solution, despite the hydrophobic nature of the metalloporphyrin. These ionizable entities do not in any way deteriorate the properties of the electropolymerizable monomer present, polymerization possibly being conducted in an aqueous phase to form polymer layers which will preferably be conductive.

Additionally, by choosing the type of complexing metal, it is possible to obtain a very wide range of detection potentials according to the metal chosen, in relation to the desired domain of electro-activity. The polymers thus obtained have strong electroactivity and a broad range of detection potential. This extensive choice in the chemical nature of the complexing metal after monomer synthesis, and hence in the domain of electrochemical activity, allows subsequent use of these detection systems for multiplexing.

This range of potential can be broadened by varying the electronic nature of the substituent (donor or attractor) on the porphyrin cycle. It is possible for example to substitute the phenyl or pyrrole groups of the porphyrin of the invention with one or more donor or attractor groups which can modify the redox potential, advantageously chosen from among halogen, and from cyano, nitro, (C$_1$-C$_4$)alkyl and (C$_1$-C$_4$)alcoxy, (C$_1$-C$_4$)alkenyl and (C$_1$-C$_4$)alkynyl groups.

As examples, the syntheses are detailed below of a tri-cationic porphyrin functionalized with a pyrrole, a di-anionic porphyrin functionalized with a pyrrole and of a porphyrin functionalized at the four meso positions, one by a pyrrole group for electrochemical polymerization, another by an activated ester group to graft a probe oligonucleotide, and at the two other positions by two pyridinium groups to ensure solubility in an aqueous medium. It is within the reach of those skilled in the art to adapt these syntheses for the preparation of the other compounds according to the invention.

The synthesis of porphyrins carrying —SO$_3$H groups at meso position can be performed using the method published by Fleisher E. B. et al (J. Am. Chem. Soc., 1971, 93, 3162-3167) which consists of treating a porphyrin, substituted at meso position by phenyls, with concentrated sulfuric acid. A gentle method was subsequently published by Bao-Hui Ye et al (Tetrahedron 2003, 59, 3593-3601) which consists of synthesizing a porphyrin carrying trimethylsilylphenyl porphyrin groups, of conducting sulfonation in the presence of $ClSO_3$ $SiMe_3$ by reflux in $CCl_4$ for 4 h, then of hydrolyzing in the presence of NaOH.

The synthesis of porphyrins substituted by —OP(OH)$_2$ groups may follow the method described by A. M. Massari et al (Polyhedron, 2003, 22, 3065-3072) consisting of synthesizing 4 formyl phenyl phosphonate, condensing it on the desired dipyromethane as described previously, followed by hydrolysis in the presence of pyridine.

The synthesis of porphyrins substituted by attractor groups is described for boron for example by R. Kachadourain et al (J. Inorganic. Biochemistry, 2003, 95, 240-248) which uses the reaction of liquid dibromine in chloroform on the desired porphyrin.

Persons skilled in the art will be able to adapt these methods to arrive at the desired porphyrins.

1) Synthesis of a Tri-Cationic Porphyrin Functionalized with a Pyrrole

The first step consists of the synthesis of benzaldehyde substituted by a protected amine group in the form of a phthalimide group. This reaction is quantitative. It is conducted for example by alkylating 3-hydroxy-benzaldehyde with 3-bromopropyl-phthalamide in the presence of potassium carbonate according to SCHEME 1 below:

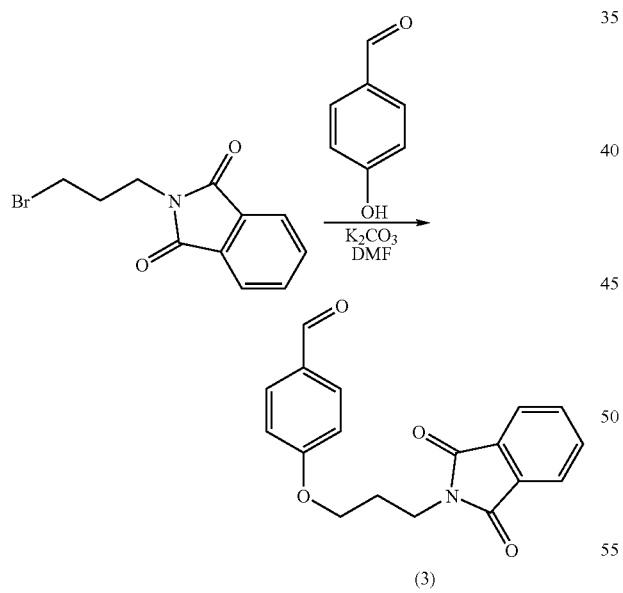

The synthesis of the porphyrin can use the benzaldehyde substituted by the phthalimide group previously synthesized, 4-pyridine-carboxaldehyde and pyrrole in propanoic acid, following the method of Adler et al (R. G. Little, J. A. Anton, P. A. Loach, J. A. Ibers, J. Heterocylic Chem., 1975, 343; Journal of Organic Chemistry, 1967 (32), p. 476) as illustrated in SCHEME 2 below:

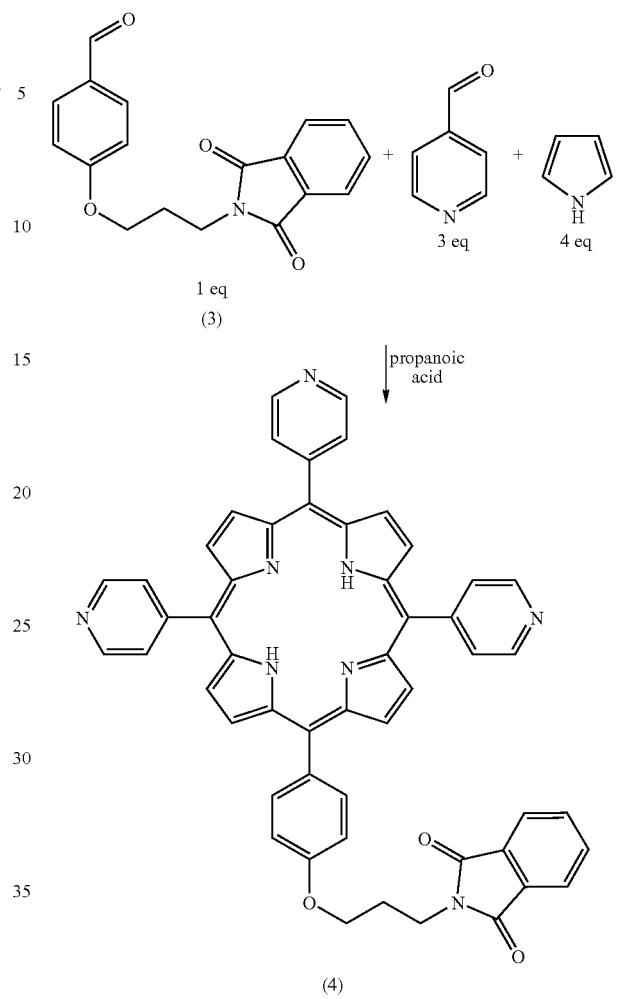

A mixture of six porphyrins is obtained. They are separated by chromatography on silica gel.

The amine function can then be obtained by deprotecting with hydrazine in a dichloromethane/ethanol mixture according to SCHEME 3 below:

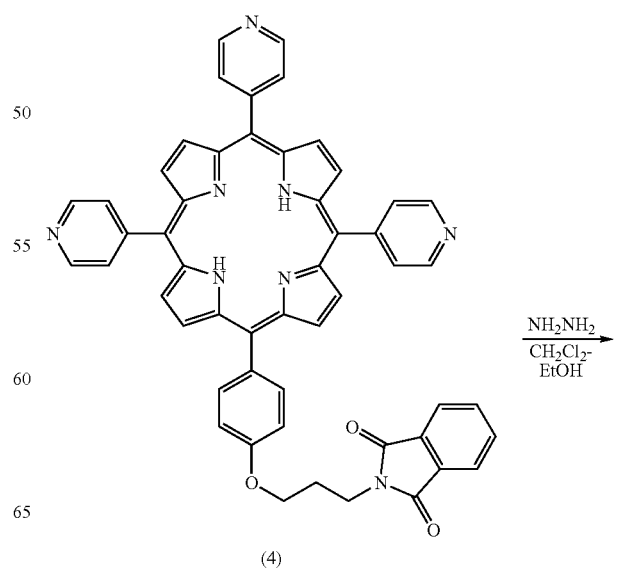

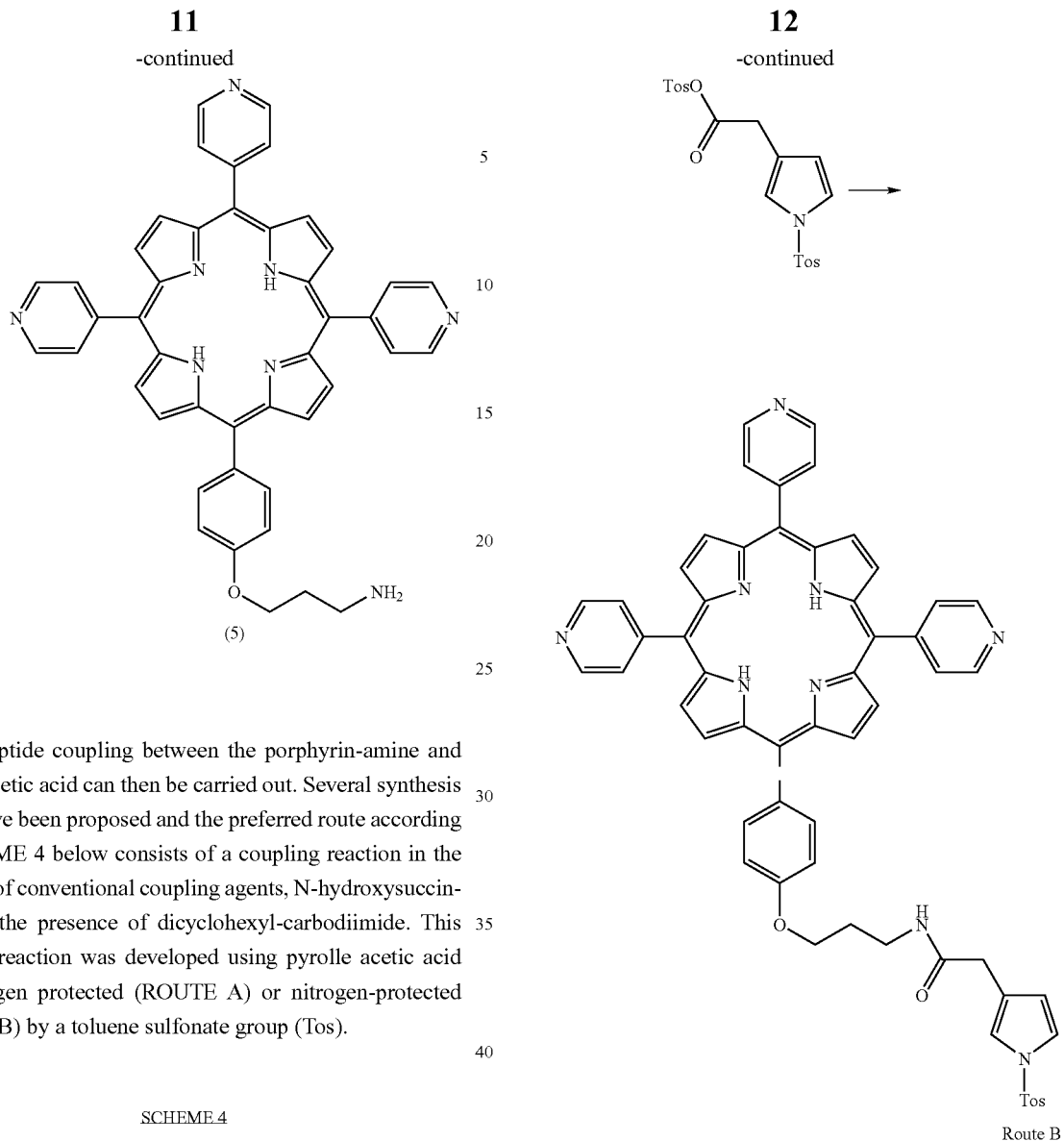

The peptide coupling between the porphyrin-amine and pyrrole acetic acid can then be carried out. Several synthesis routes have been proposed and the preferred route according to SCHEME 4 below consists of a coupling reaction in the presence of conventional coupling agents, N-hydroxysuccinimide in the presence of dicyclohexyl-carbodiimide. This coupling reaction was developed using pyrolle acetic acid non-nitrogen protected (ROUTE A) or nitrogen-protected (ROUTE B) by a toluene sulfonate group (Tos).

SCHEME 4

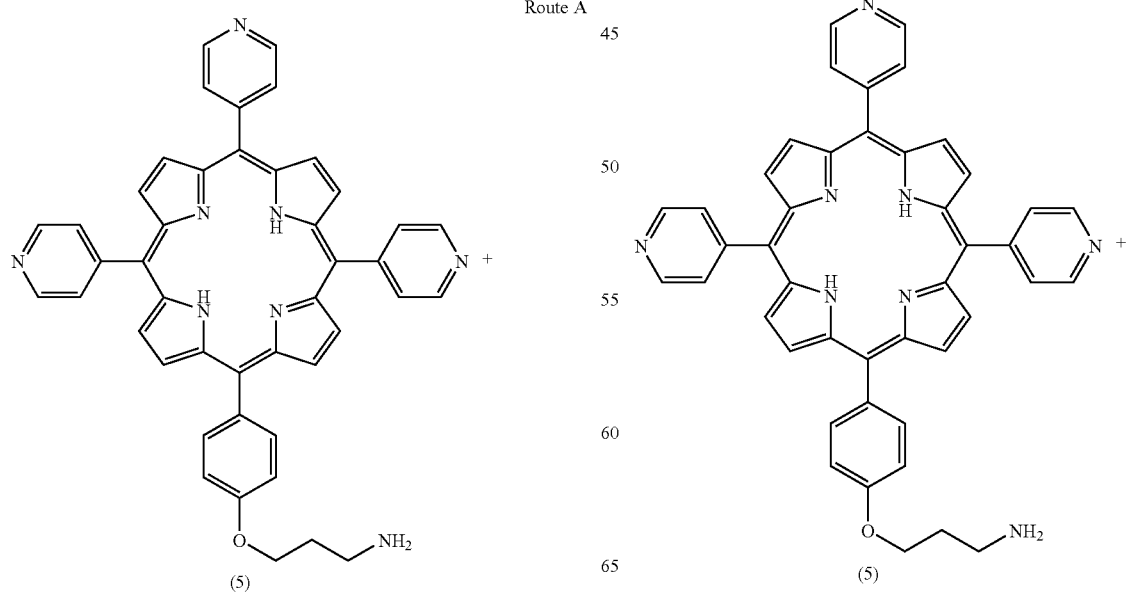

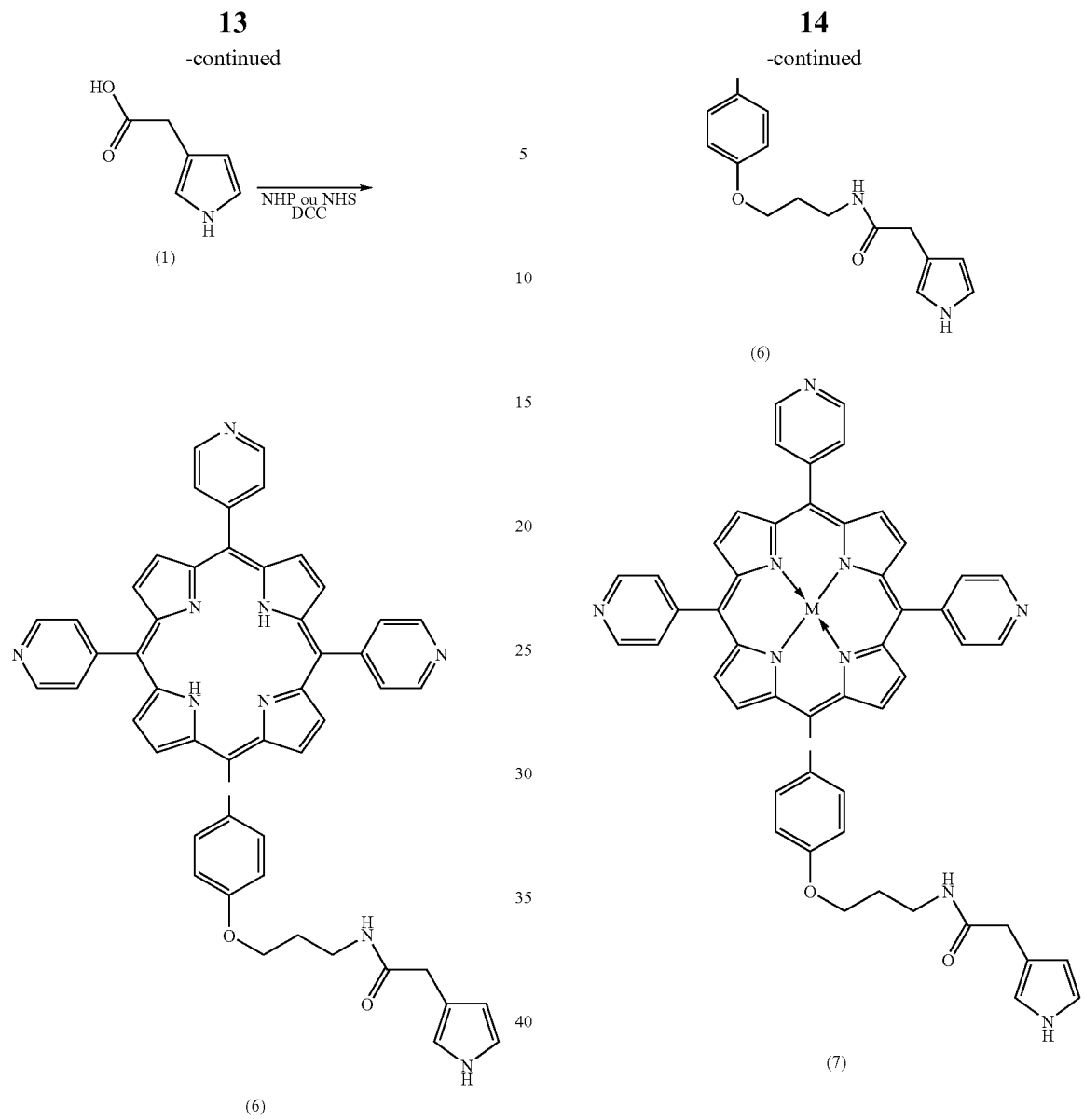

The metalation of the porphyrin is easy and quantitative. It is generally conducted in the presence of the metal chloride chosen at the second degree of oxidation in dimethylformamide according to SCHEME 5 below:

The last synthesis step is methylation of the pyridyl groups of the porphyrin to make it tri-cationic. This reaction is quantitative and is made for example in the presence of a large excess of methyl iodide in DMF (dimethylformamide) according to SCHEME 6 below:

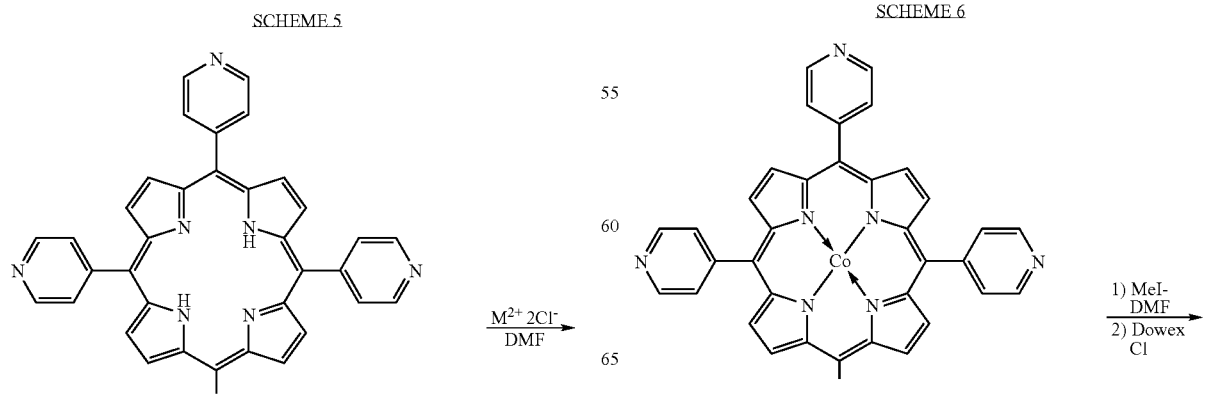

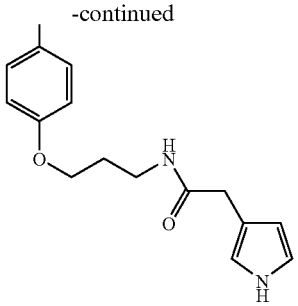

(7)

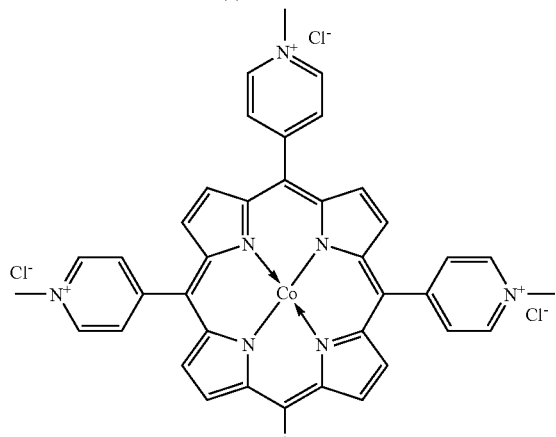

(10)

The passing through a Dowex-Cl column with water as eluent leads to counter-anion exchange and final purification.
2) Synthesis of a Di-Anionic Porphyrin Functionalized with a Pyrrole

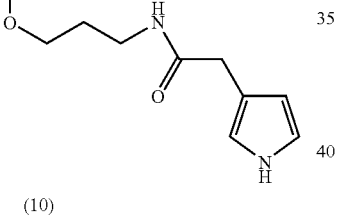

(20)

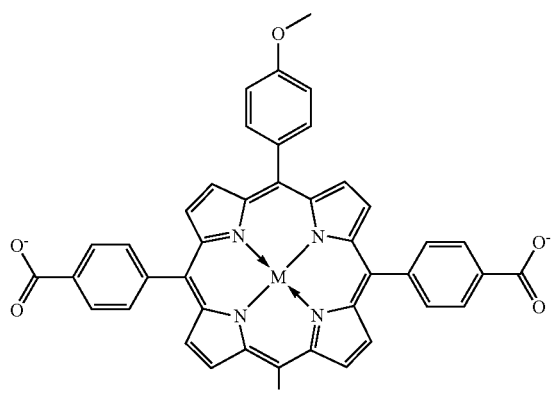

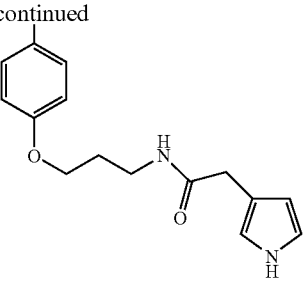

The desired porphyrin is meso-substituted by three types of different groups. In this case, Adler's method for its synthesis is less well adapted, since it would be necessary to separate twenty-one porphyrins. If two different substituents are positioned at trans, synthesis can be divided into two steps: synthesis of a dipyrromethane (B. J. Littler, S. Lindsey, *Journal of Organic Chemistry*, 1999 (64), p. 1391; J. K. Laha, S. Lindsey, *Organic Process Research Development*, 2003 (7), p. 799), then construction of the porphyrin cycle (D. T. Gryko, M. Tasior, *Tetrahedron Letters*, 2003 (44), p. 3317). It is also possible to follow the protocol described by Rao O. D., Dhanalekshmi S., Littler B. J. and Lindsey J. S., *Journal of Organic Chemistry*, 2000, 65, p. 7323-7344.

Synthesis of dipyrromethane can be conducted in accordance with SCHEME 7 below, by reaction of the corresponding aldehyde with the pyrrole used as solvent and in the presence of TFA as Lewis acid.

SCHEME 7

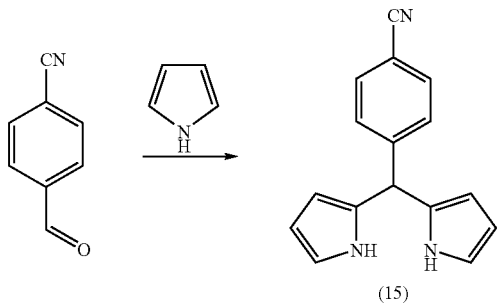

(15)

The porphyrin cycle can then be constructed as described by Rao P. D., Dhanalekshmi S., Littler B. J. and Lindsey J. S., *Journal of Organic Chemistry*, 2000, 65, p. 7323-7344 in accordance with SCHEME 8 below, by reaction in the presence of trifluoroacetic acid (TFA) of two equivalents of dipyrromethane with one equivalent of each of the two necessary aldehydes. Conjugation of the cycle is obtained for example by oxidation with 2,6-dichloro-3,5-dicyanobenzoquinone (DDQ). In theory, on completion of the synthesis, the mixture should consist of three different porphyrins.

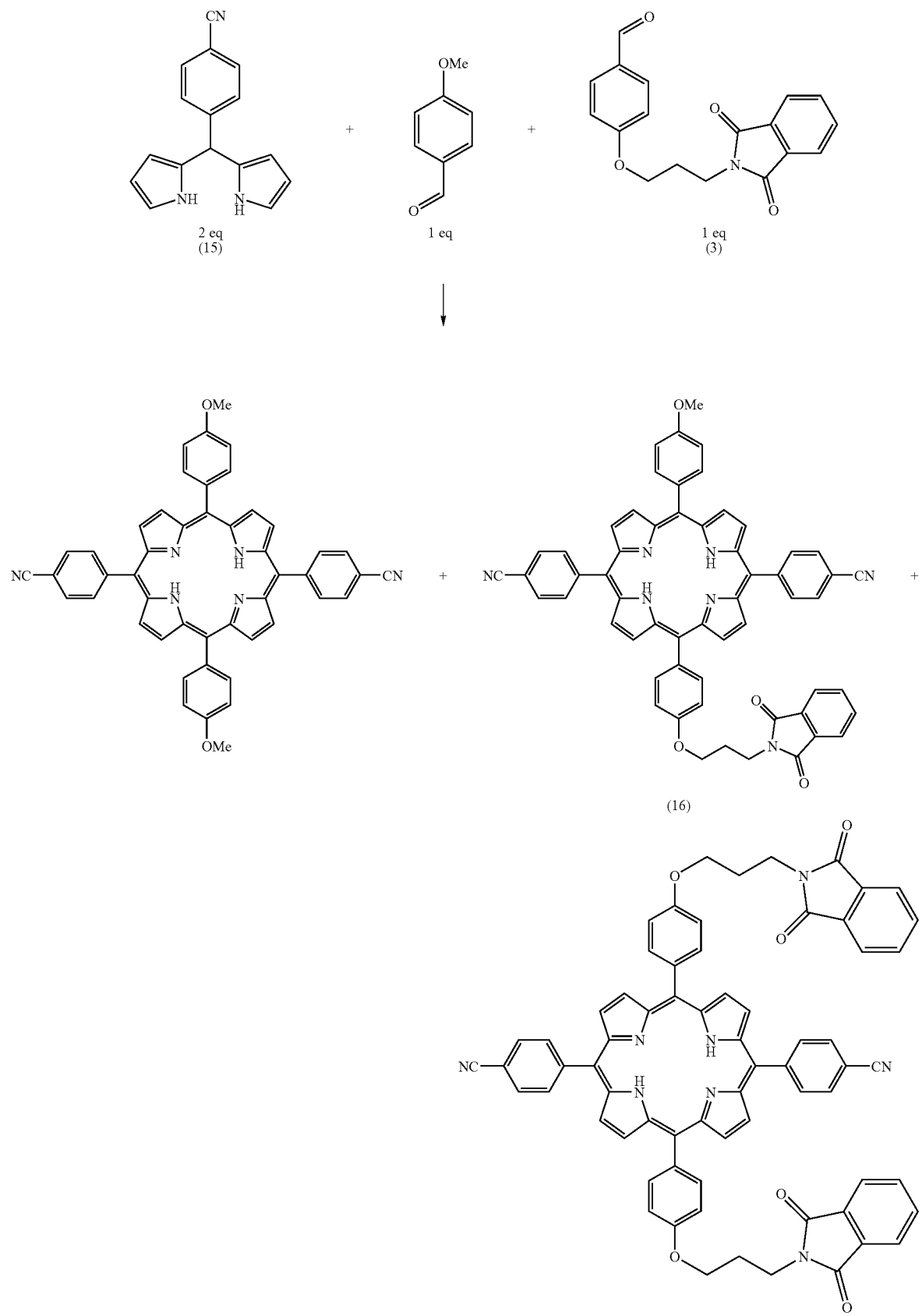

The three synthesized porphyrins can then be separated, notably by chromatography on silica gel.
Next, the amine function can be obtained by deprotection with hydrazine according to SCHEME 9 below:
SCHEME 9
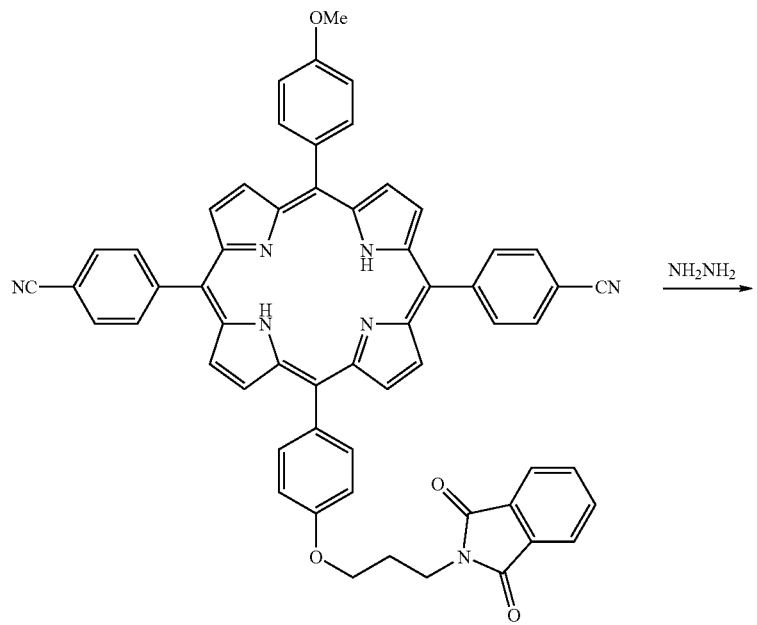
(16)
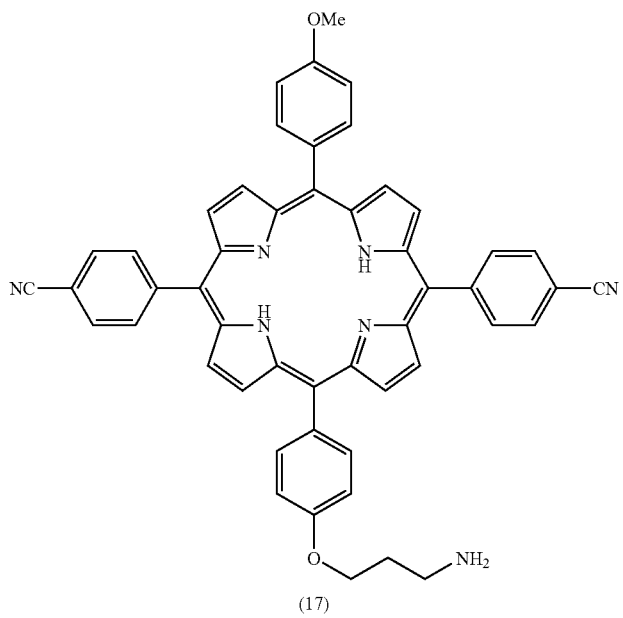
(17)

The peptide coupling of the porphyrin-amine with the pyrrole-acid is conducted in the presence of DCC (1,3-dicyclohexylcarbodiimide) and NHS(N-hydroxysuccinimide) according to SCHEME 10 below:
SCHEME 10
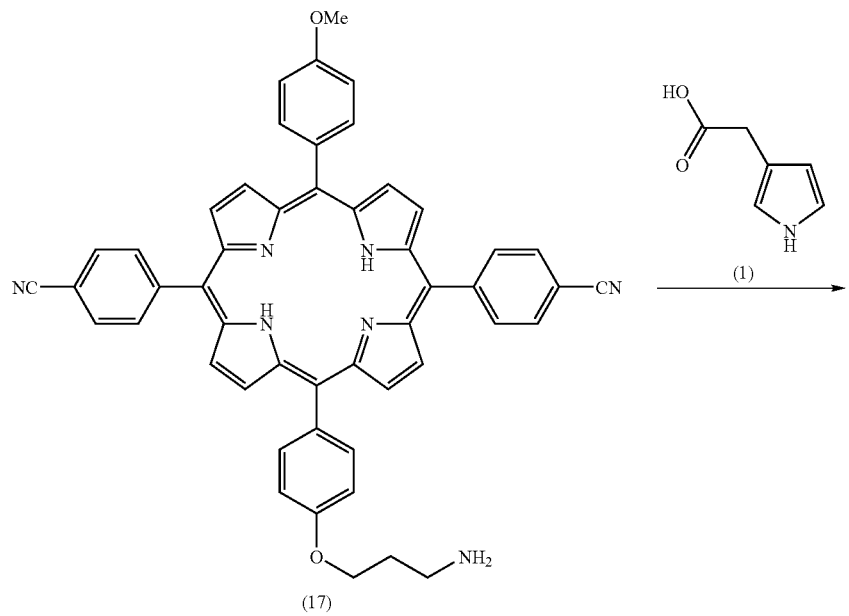
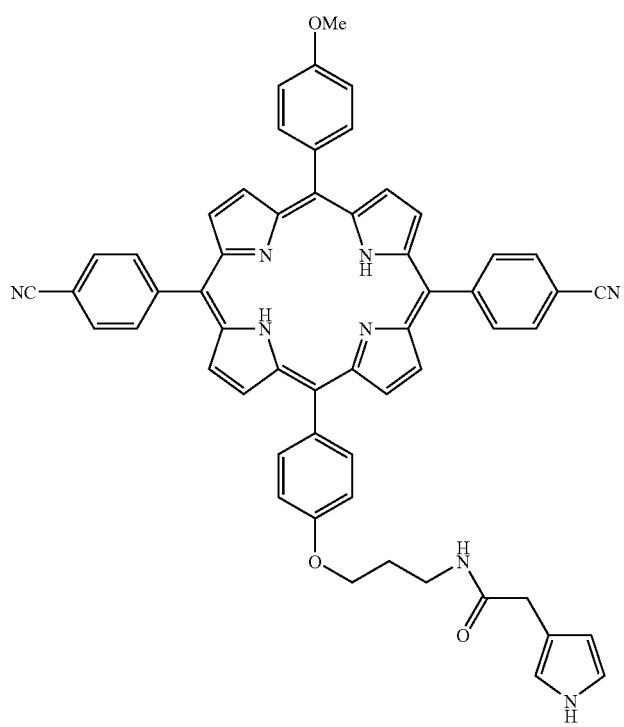

To obtain the porphyrin carrying two —COOH groups, the nitrile groups are then hydrolyzed in a basic medium and the porphyrin is metallated with the desired metal according to SCHEME 11 below:
SCHEME 11
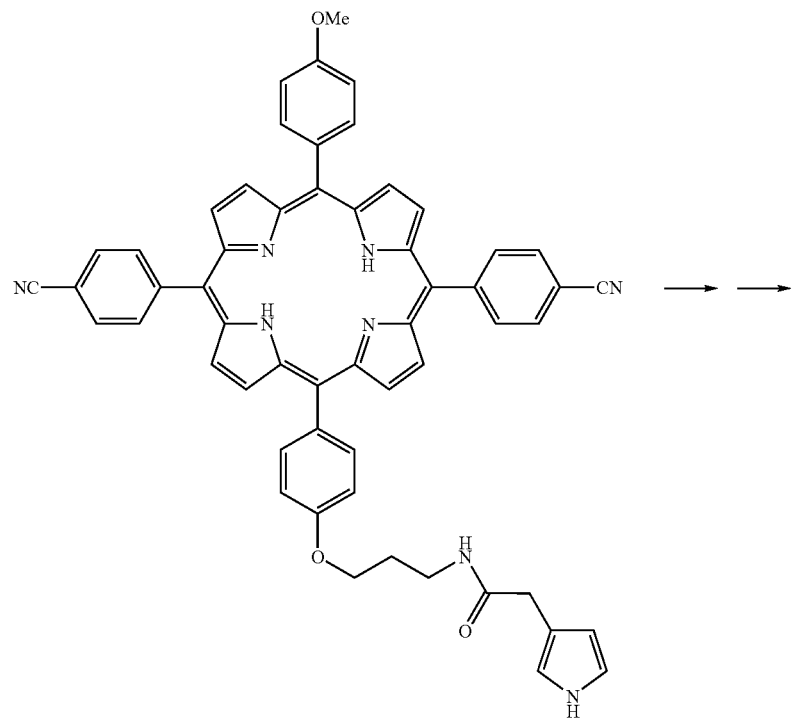
(18)
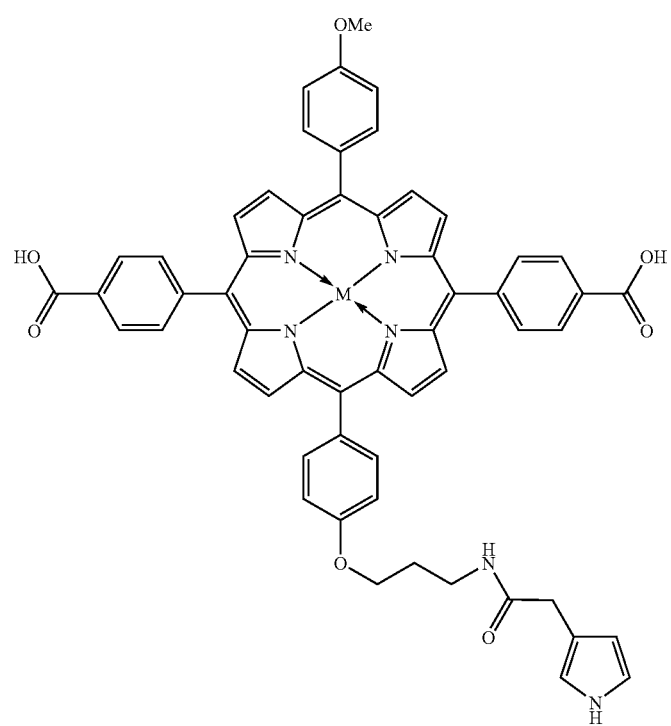
(20)

3) Synthesis of a Porphyrin Functionalized by a Pyrrole Group and by an Activated Ester Group:

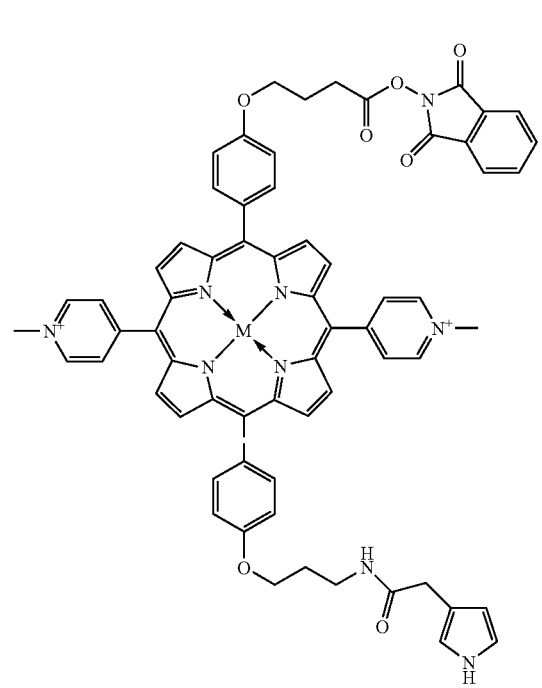

The remainder of the description relates to the preparation of a porphyrin functionalized on these four meso positions, one by a pyrrole group for electrochemical polymerization, another by an activated ester group to graft the oligonucleotide probe, and the two others by two pyridinium groups at the two other meso positions to ensure solubility in an aqueous medium. A molecular modeling study has shown that it is preferable to substitute the two functional groups, pyrrole and activated ester, at para position on the porphyrin to avoid steric genes during coupling reactions. The preparation of said porphyrin can be achieved firstly by synthesizing the two porphyrin moieties (dipyrromethanes) carrying the A functional group (dipyrromethane comprising a para-substituted phenyl by an ester function) and B functional group (dipyrromethane comprising a para-substituted phenyl by a spacer carrying a function able to react on a pyrrole), and subsequently by conducting a cyclizing reaction in the presence of the third group C (pyridin-carboxaldehyde). This synthesis is conducted following the method described by Lindsey et al. [D. T. Gryko, M. Tasior, Tetrahedron Letters, 2003, 44, 3317; J. Littler, S. Lindsey, J. Org. Chem., 1999, 64, 1391; J. K. Laha, S. Lindsey, Org. Process Res. Develop., 2003, 7, 799.]

The synthesis of the two dipyrromethanes can be performed using the aldehyde corresponding to the pyrrole as solvent and trifluoroacetic acid (TFA) as Lewis acid. For the dipyrromethane with the "nitrile" arm the operating mode according to SCHEME 12 below can be followed.

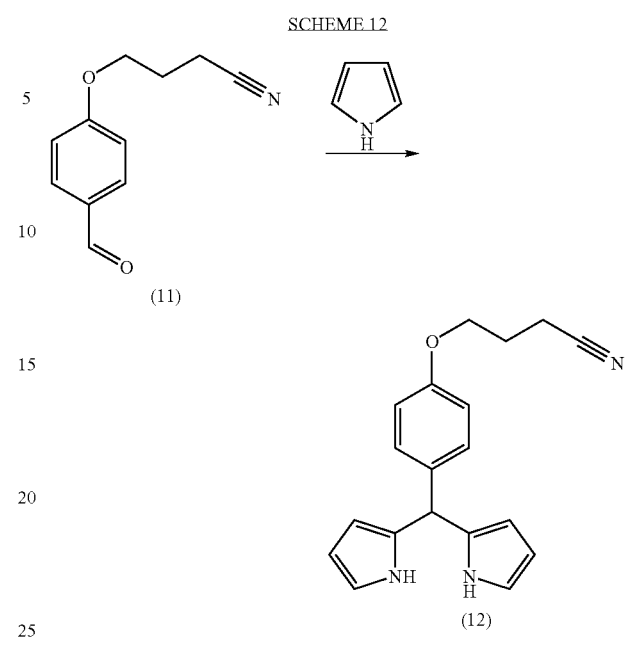

For the dipyrromethane with the "phthalimide" arm, the reaction is conducted according to SCHEME 13 below:

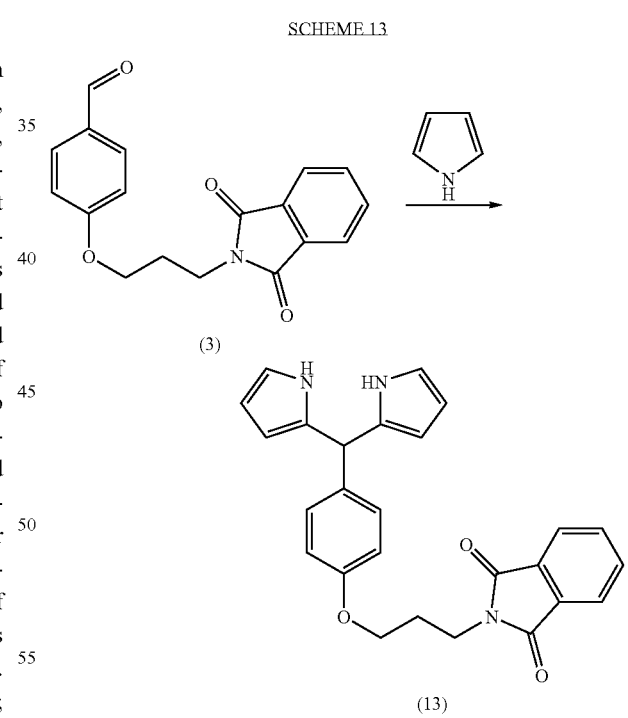

The porphyrin cycle is constructed from the two dipyrromethanes and the pyridine-carboxaldehyde in the presence of TFA. The conjugation of the cycle can be obtained by oxidation with 2,6-dichloro-3,5-dicyanobenzoquinone (DDQ), (SCHEME 14). On completion of the synthesis, the reaction mixture theoretically consists of three different porphyrins which can be separated by chromatography on silica gel.

SCHEME 14

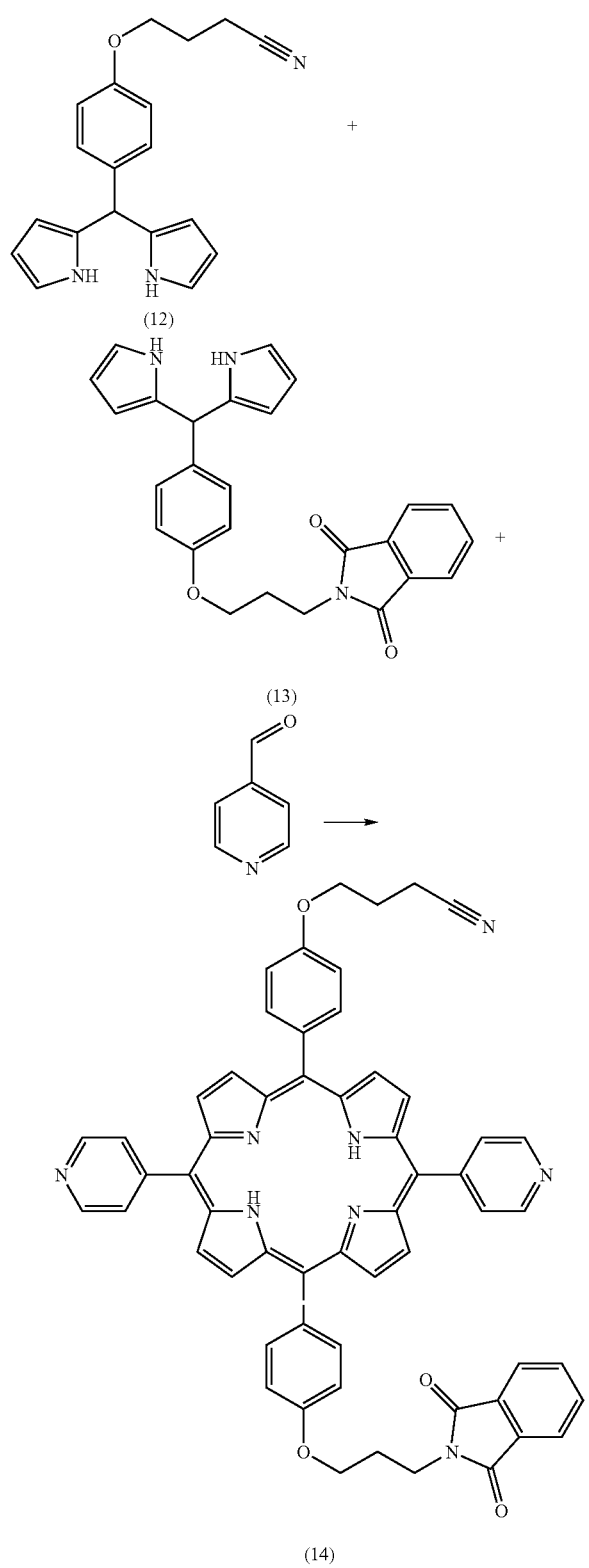

During synthesis, some functions, notably the amine function of the pyrrole may be protected, then deprotected. The protector groups of alcohols, amines and carboxylic acids are well known to those skilled in the art. Reference may be made to <<Protective Groups in Organic Synthesis>> $2^{nd}$ edition, Greene T. W. and Wuts P. G. M., ed. John Wiley and Sons, 1991. As protective group for amines, mention may be made of the trifluoroacetyl, tert-butoxycarbonyl or 9-fluorenyl-methoxycarbonyl groups for example.

4) Synthesis of a Di-Cationic Porphyrin Functionalized with a Pyrrole (26)

In the same manner as for the di-anionic porphyrin, this di-cationic porphyrin lies about a trans axis and has a methoxy function, mimicking the future arm receiving the ODN-probe.

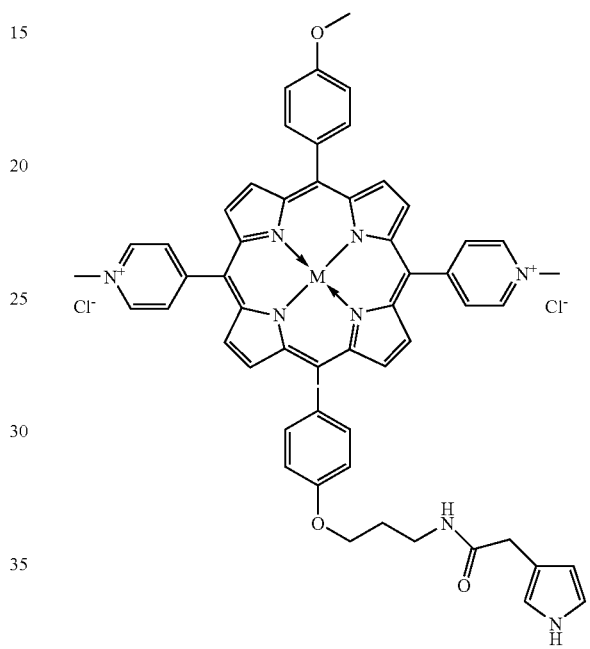

One preparation mode for the di-cationic monomer (26) is given in SCHEME 15 below. Since the porphyrin cycle is substituted by three types of different groups, but lies about a trans axis, the (2+2) method previously described is used for its synthesis. As previously, the terminal amine of the alcoxy chain substituting the porphyrin is protected in the form of a phthalimide, during the construction of the porphyrin cycle. The first step consists of the synthesis of the pyridyl dipyrromethane (21). After constructing the porphyrin cycle and deprotecting the amine (23), the amine is coupled with the pyrrole derivative (1). Finally the metalation and permethylation reactions lead to obtaining the desired di-cationic monomer 26.

SCHEME 15

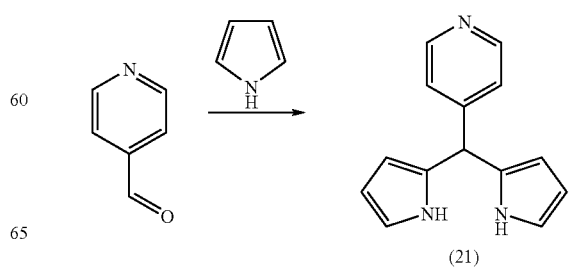

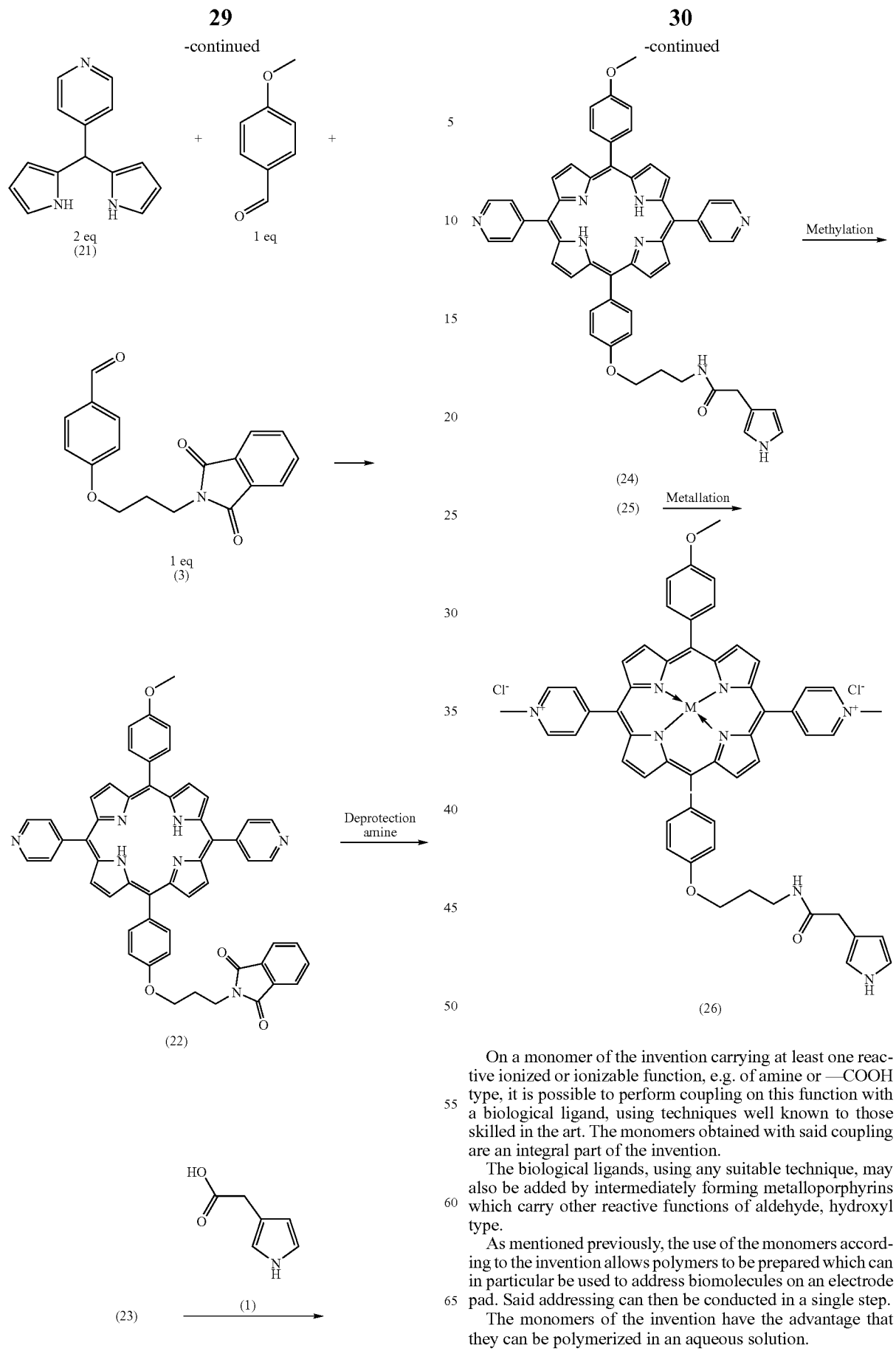

On a monomer of the invention carrying at least one reactive ionized or ionizable function, e.g. of amine or —COOH type, it is possible to perform coupling on this function with a biological ligand, using techniques well known to those skilled in the art. The monomers obtained with said coupling are an integral part of the invention.

The biological ligands, using any suitable technique, may also be added by intermediately forming metalloporphyrins which carry other reactive functions of aldehyde, hydroxyl type.

As mentioned previously, the use of the monomers according to the invention allows polymers to be prepared which can in particular be used to address biomolecules on an electrode pad. Said addressing can then be conducted in a single step.

The monomers of the invention have the advantage that they can be polymerized in an aqueous solution.

A further subject of the invention is an electropolymerisation method performed in an aqueous solution, using at least one of the monomers of the invention and in particular at least one monomer carrying a biological ligand. Electropolymerisation may or may not be conducted in a buffer solution advantageously containing a carrier electrolyte such as NaCl, LiClO$_4$. The pH of the solution is advantageously between 3 and 8.

This electropolymerisation can be a homopolymerization. In particular, homopolymerization with a soluble monomer conforming to the invention carrying a biological ligand. Homopolymerization may also be performed using a soluble monomer of the invention carrying a reactive amine, hydroxyl or carboxylic acid function, optionally in protected form. This homopolymerization may then be followed by coupling of said reactive function with a biological ligand.

Preferably, electropolymerisation is copolymerization between at least two different monomers of which at least one conforms to the invention. Preferably at least one, and preferably only one, of the monomers carries a biological ligand. Evidently, the monomer(s) used, other than those conforming to the invention, are soluble in an aqueous solution. Copolymerization uses at least two monomers according to any of claims 1 to 37 in which the metal is different.

According to one preferred variant, the polymerization reaction is conducted so as to obtain a polymer carrying at least two different biological ligands.

It is also advantageous that all the monomers used should comprise a pyrrole as electropolymerizable unit.

Copolymerization for example may be conducted between a monomer of the invention carrying a biological ligand and a non-substituted pyrrole or a pyrrole-3-alcanol, or between a monomer of the invention which does not carry a biological ligand, a non-substituted pyrrole or a pyrrole-3-alcanol and a pyrrole carrying a biological ligand at position 3. As pyrrole-3-alcanol, mention may be made of 3-(hydroxyethyl)pyrrole.

It is also possible to conduct copolymerization of at least one soluble monomer according to the invention carrying a reactive amine, hydroxyl or carboxylic acid function, optionally in protected form. This copolymerization reaction in aqueous phase is advantageously followed by coupling of said reactive function with a biological ligand.

A further subject of the present invention concerns polymers able to be obtained by said polymerization reactions, optionally followed by coupling with a biological ligand.

Therefore, a further purpose of the invention is to propose electroactive probes corresponding to a polymer of the invention carrying at least one biological ligand, and electrodes coated at least in part with said probe which are easier to produce and which allow more direct measurement of the probe ligand/target ligand interaction.

By «electroactive probe» is meant a probe whose electrochemical response is modified when a target ligand interacts specifically with a probe ligand carried by the probe. Therefore a change in the electrochemical signal is observed subsequent to the specific interaction with the analyte.

By «target ligand» is meant any molecule able to interact specifically with a probe ligand fixed to a monomer unit of the polymer according to the invention obtained from at least one monomer of the invention and hence able to be detected with this polymer. This target ligand may be a biomolecule such as nucleotide for example or a polynucleotide, nucleic acid, oligonucleotide, polypeptide, protein, antibody, antigen, peptide, lipid, steroid, or a sugar. The probe ligand carried by the polymer is specific to the target ligand to be detected.

A further subject of the present invention therefore concerns electroactive probes in the form of a conductor homopolymer, able to be obtained by electropolymerisation of soluble monomer according to the invention carrying a biological ligand.

Although not preferred, electroactive probes in the form of a conductor homopolymer able to be obtained by electropolymerisation of a soluble monomer according to the invention carrying a reactive amine, hydroxyl or carboxylic acid function optionally in protected form, followed by coupling of said reactive function with a biological ligand, form an integral part of the invention.

Preferably the subject of the present invention concerns electroactive probes in the form of a conductor copolymer able to be obtained by copolymerization of at least two different monomers of which at least one conforms to the invention. At least one and preferably only one of the monomers carrying a biological ligand. In this manner a spacing of the biological probe ligands is obtained which improves sensitivity. In particular, a soluble monomer conforming to the invention is used carrying a biological ligand and a 3-(hydroxyethyl)pyrrole monomer. Another preferred copolymer may be obtained by copolymerization of a soluble monomer according to the invention, which does not carry a biological ligand, with a monomer carrying a biological ligand preferably carried at position 3 of the pyrrole, and a 3-(hydroxyethyl)pyrrole monomer.

Here again, even if they are not preferred, the electroactive probes in the form of a conductor-copolymer able to be obtained by electropolymerisation of at least one soluble monomer according to the invention carrying a reactive amine, hydroxyl or carboxylic acid function, optionally in protected form, followed by coupling of said reactive function with a biological ligand, form an integral part of the invention.

According to another of its aspects, a further subject of the invention concerns electrodes comprising a conductor carrier of which all or part of the surface is coated with an electroactive probe such as defined above.

A further subject of the present invention is a method to detect a target ligand in a biological sample, in which the sample is contacted with an electroactive probe such as defined previously, carrying a probe ligand, under conditions suitable for the probe ligand/target ligand interaction, and the difference in potential or current emitted by the probe is evidenced and optionally quantified before and after contacting with the sample.

The polymers obtained from the monomers of the invention can be used in particular in any applications in which biological ligands are addressed and immobilized on a solid carrier.

More particularly, these polymers can be obtained in the form of stand-alone films or in the form of films on electrodes. The electrode, by measuring the current delivered during the reaction, effectively provides control over the progression of the polymerization reaction. The electrode can also be used to measure the subsequent electrochemical response of the polymer. The present invention therefore also concerns an electrode comprising a conductor carrier whose surface is coated with at least one electroactive conductor polymer functionalized with biological ligands according to the invention, i.e. an electroactive probe according to the invention.

In the prior art conductive carriers for electrodes are known and particular mention may be made of substrates in metal or carbon derivatives. For the fabrication of an electrode according to the invention, the polymer is generally deposited on the conductive carrier. Electrochemical polymerization is advantageously performed on the surface of the electrode to obtain an electrode comprising a conductive carrier coated on its surface with a polymer of the invention. In one advantageous embodiment of the invention, the electrode is obtained by depositing a polymer layer on the surface of a carrier in gold or platinum.

Since it is possible to limit and control electrochemical polymerization reactions at an electrode, the monomers of the invention enable the immobilization and addressing of biological ligands on small surfaces. This addressed electropolymerisation allows miniaturized, ordered, dot matrices to be obtained, each of the dots carrying a defined biological ligand. In one advantageous embodiment, the invention also relates to an electrode matrix.

The invention therefore also concerns an electrode matrix comprising at least one electrode according to the invention. Said electrode matrices may be in the form of an analysis card or chip comprising a series of wells, each well corresponding to an electrode.

In one advantageous embodiment, the different electrodes of the matrix carry different biological ligands. According to one particular embodiment, the invention concerns a plurality of electrodes or microelectrodes fixed on a solid carrier, these electrodes are coated with a copolymer according to the invention and advantageously carry different biological ligands. Said electrode matrices may advantageously be obtained by addressed electropolymerisation of monomers according to the invention, and in particular by copolymerization of a monomer carrying a biological ligand with a monomer non-functionalized with a ligand.

The electrodes and electrode matrices of the invention can be used in particular for the detection of analytes which may be present in a sample and able to react specifically with the biological ligands carried by the polymer.

With the present invention, it is possible to detect a target ligand in any type of sample. In one particular embodiment of the invention the sample is a biological sample. Advantageously, this sample may be taken from a patient for diagnosis purposes. For example, the sample may be a urine sample, blood, serum or plasma sample, cell extracts of a body fluid. Since the probe is electroactive, its electrochemical response is modified if a target ligand interacts specifically with the probe ligand carried by the polymer. The electroactive conductor polymer of the invention therefore translates the interaction with the target ligand into an electrochemical signal. The specific interaction of a target ligand with the probe ligand carried by the polymer generates a change in the electrochemical response of the polymer under consideration, compared with the response obtained before the target ligand is added. Advantageously, the detection of the target ligand is made by electric measurement. By <<electric measurement>> is meant measurement of a variation of potentiometric type, such as the variation in the oxidation potential of the polymer, or measurement of a variation of amperometric type i.e. variation in the oxidation current observed at a given potential. These variations are measured rapidly, sensitively and quantitatively following methods will known to those skilled in the art.

In one advantageous embodiment of the invention, electric measurement consists of measuring a variation in potential or in current. In one particular embodiment of the invention cyclic voltammetry is used. This is an electroanalytical method which consists of scanning a potential range in one direction then in the other at constant speed. The voltamperogram obtained gives the current response of the electrochemical system tested and allows its characterization.

Detection methods by electric measurement are preferred for the polymers of the invention. However other conventional detection method known to those skilled in the art may also be used.

In one particularly advantageous embodiment of the invention, the detection of the specific interaction between the target ligand and the probe ligand carried by the polymer can be conducted with the electrode used for electropolymerisation of the polymer. For example, the hybridization of a nucleic acid, complementary to the oligonucleotides carried by the polymer, can be detected by electrical measurement on the electrode which carries the polymer of the invention.

The hybridization of oligonucleotides can be monitored directly by measuring the variation in the detected electrochemical signal, or via an enzymatic reaction. In this case, the target oligonucleotide carries a biotin for example. After adding Streptavidin-Peroxidase and the enzyme substrate, detection can be conducted either at the substrate or via the electrochemical signal.

Similarly, it is possible, by means of variations in the electrochemical signal, to monitor protein/protein interactions of antibody/antigen type and antibody/protein type in particular.

It is also possible to use polymers able to be obtained with the monomers of the invention, for the assay of phosphate ions when monitoring a PCR reaction for example; to study the activity of an enzyme; in molecular electronic applications such as described for example in *Science* 2004, 306, 2048-2074.

In one particular embodiment of the invention, the electroactive polymer comprises different probe biomolecules. The metalloporphyrins are then complexed by different metals allowing the detection of several types of target molecules.

The following examples for the preparation of monomers and the electrochemical characterization of the polymers obtained, are given by way of illustration.

A. EXAMPLES OF MONOMER PREPARATION

I—Syntheses of Pyrroles Substituted by Acid and Alcohol Groups (1H-pyrrol-3-yl)acetic acid (1)

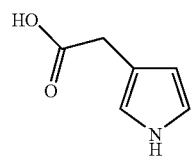

(1)

3.37 g (11.5 mmol) of [1-(toluene-4-sulfonyl)-1H-pyrrol-3-yl]methyl acetate are dissolved in 35 mL methanol and 35 mL of a 5N sodium hydroxide solution. The reaction medium is heated under reflux for 4 hours, concentrated to dryness and re-dissolved in water. The aqueous phase is washed with diethyl ether, then acidified slowly in an ice bath with a 6N hydrochloric acid solution until a pH of around 3 is obtained. The aqueous phase is extracted with diethyl ether. The ethereal phase is washed with a saturated NaCl solution, dried over $Na_2SO_4$, and concentrated to dryness. 949 mg of compound (I) is obtained in the form of white crystals, with a yield of 66%.

Remark: Compound (I) must be stored in solution in diethyl ether. Before use the solution must be filtered through a sintered glass filter and concentrated to dryness.

Molar mass M(g·mol$^{-1}$): 125.13
TLC: CH$_2$Cl$_2$/EtOH 95/5: R$_f$=0.16
$^1$H NMR: CDCl$_3$, δ (ppm): 8.17 (1H); 6.78 (2H; s); 6.21 (IH; s); 3.58 (2H; s)

2-(1H-pyrrol-3-yl)ethanol (2)

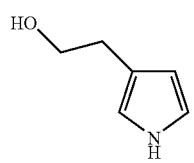

(2)

A solution of 5.0 g (17 mmol; 1 eq) of [1-(toluene-4-sulfonyl)-1H-pyrrol-3-yl]methyl acetate in minimum anhydrous THF is added dropwise, under argon, to a mixture of 60 mL THF (distilled over sodium) and 12 mL (24 mml; 1.4 eq) of a 2M solution of (BH$_3$)S(CH$_3$)$_2$ in THF. The reaction medium is heated under reflux for 4 hours, then gently poured onto 100 mL of a 6N sodium hydroxide solution placed in an ice bath. The aqueous phase is extracted with dichloromethane. The organic phase is then washed with a saturated NaCl solution, dried over Na$_2$SO$_4$ and concentrated to dryness. The mixture is purified by chromatography on silica gel with a 4/6 (v/v) mixture of AcOEt/petroleum ether.

The crude product is dissolved in 60 mL methanol and 60 ml of 5N sodium hydroxide. The reaction medium is heated under reflux for 3 hours, then concentrated to dryness and re-dissolved in ethyl acetate and water. The two phases are separated. The aqueous phase is extracted with ethyl acetate. The organic phase is washed with water and a saturated NaCl solution, dried over Na$_2$SO$_4$ and concentrated to dryness. The product obtained is solubilized in water and filtered through celite. 720 mg of compound (2) are obtained with a yield of 38%.

M(g·mol$^{-1}$): 111.14
$^1$H NMR: CD$_3$OD, δ (ppm): 6.61 (1H; s); 6.54 (IH; s); 5.96 (1H; s); 3.65 (2H; t; 7.5 Hz); 2.66 (2H; t; 7.5 Hz)

II—Synthesis of a Porphyrin Substituted by a Pyrrole and Three Pyridiniums

II-1 4-[1-propoxy-3-(N-phthalimide)]benzaldehyde (3)

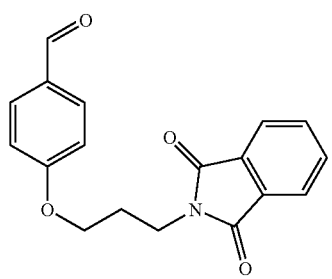

(3)

Under argon, 3.66 g (30 mmol; 1 eq) of 4-hydroxybenzaldehyde are dissolved in 20 mL DMF, and 8.3 g (60 mmol; 2 eq) of K$_2$CO$_3$ are added. After stirring for 1 hour at 70° C., the medium becomes pink. Using a dropping funnel, a solution of 9.65 g (36 mmol; 1.2 eq) of N-(3-bromopropyl)phthalimide in 20 mL DMF is added slowly. The reaction medium is stirred 1 hour at 70° C., then 2 hours at 90° C. After cooling, the medium is filtered through a sintered glass filter. The filtrate is diluted with dichloromethane until precipitation, then filtered again through sintered glass. The new filtrate is concentrated to dryness then re-dissolved in dichloromethane. The organic phase is washed twice with water then with a saturated NaCl solution, dried over Na$_2$SO$_4$ and concentrated to dryness. 10.03 g of compound (3) are obtained which is used without any additional purification.

M(g·mol$^{-1}$): 309.32
TLC: CH$_2$CL$_2$/MeOH 95/5: R$_f$=0.74
$^1$H NMR: CDCl$_3$, δ (ppm): 9.80 (1H; s); 7.77 (2H; dd; 5.5 Hz; 3.1 Hz); 7.73 (2H; d; 8.8 Hz); 7.67 (2H; dd; 5.5 Hz; 3.1 Hz); 6.83 (2H; d; 8.8 Hz); 4.07 (2H; t; 6.4 Hz); 3.87 (2H; t; 6.4 Hz); 2.17 (2H; qi; 6.4 Hz).

II-2 [5-[4-(3-(N-phthalimide)-1-propoxy)phenyl]-10,15,20-tri-pyridin-4-yl]porphyrin (4)

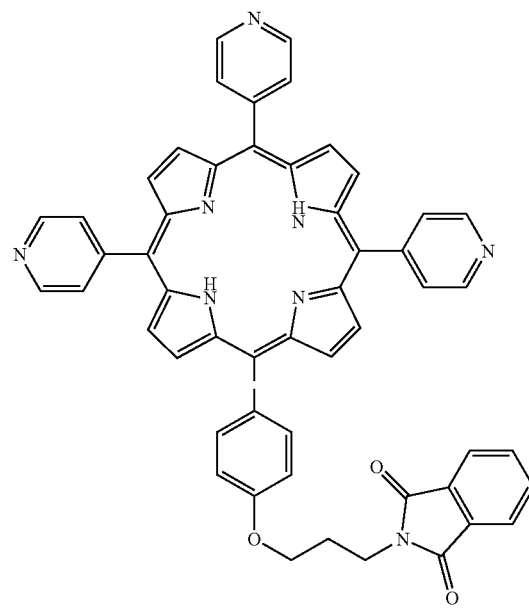

(4)

In 225 mL propanoic acid, 4.30 mL (45 mmol; 3 eq) of 4-pyridine-carboxaldehyde and 4.64 g (15 mmol; 1 eq) of compound (3) are dissolved. After adding pumice stone the reaction medium is heated under reflux using a water heater for 10 min.

Using a dropping funnel, a solution of 4.19 mL (60 mmol; 4 eq) of (distilled) pyrrole in 20 mL propanoic acid is added slowly. The medium turns black as soon as the first drops are added. The reaction medium is heated under reflux for 1 h 30. Half a spatula of chloranil is added then the medium is held under reflux for 30 min. The propanoic acid is fully evaporated. After a first filtration on silica with a 9/1 (v/v) mixture of CH$_2$Cl$_2$/EtOH the mixture is purified by chromatography on 600 g of silica gel with a mixture of CH$_2$Cl$_2$ containing increasing proportions of ETOH (from 1% to 5%). The product, after dissolution in minimum CH$_2$Cl$_2$, is precipitated with hexane. 847 mg of compound (4) are obtained with a yield of 6.9%.

M (g·mol$_{-1}$): 820.92

TLC: CH$_2$Cl$_2$/EtOH 95/5: R$_f$=0.17 (5th porphyrin/6)

$^1$H NMR: CDCl$_3$, δ (ppm): 9.04 (6H; dd; 4.4 Hz; 1.5 Hz); 8.95 (2H; d; 4.9 Hz); 8.85 (4H; s); 8.82 (2H; d; 4.9 Hz); 8.16 (6H; d; 4.4 Hz); 8.09 (2H; d; 8.3 Hz); 7.89 (2H; dd; 5.4 Hz; 2.9 Hz); 7.72 (2H; dd; 5.4 Hz; 2.9 Hz); 7.20 (2H; d; 8.3 Hz); 4.33 (2H; t; 6.4 Hz); 4.07 (2H; t; 6.4 Hz); 2.38 (2H; qi; 6.4 Hz); −2.89 (2H, s)

Mass Spectrometry (MS): Positive-ion electrospray ionization: (M+H)$^+$=821.

II-3 [5-(4-(3-amino-1-propoxy)phenyl-10,15,20-tri-pyridin-4-yl]porphyrin (5)

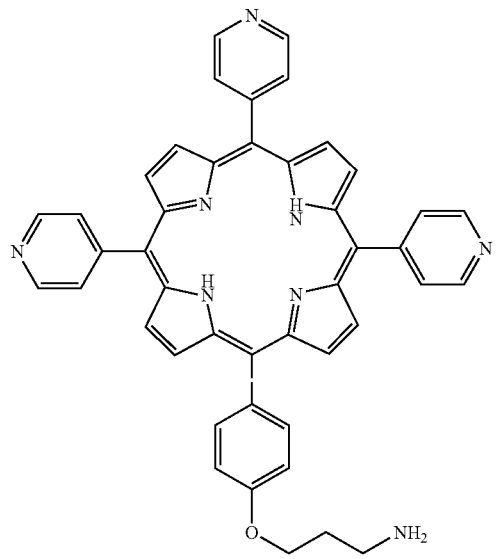

(5)

In 30 mL of a ½ (v/v) mixture of CH$_2$Cl$_2$/EtOH, 800 mg (0.97 mmol; 1 eq) of compound (4) and 0.5 mL (9.75 mmol; 10 eq) of a 64% hydrazine solution in water are dissolved. The reaction medium is heated under reflux for 24 hours, then stirred at ambient (AT) for 24 hours. A 10% hydrochloric acid solution is added. The medium is filtered through sintered glass and the filtrate is neutralized with a 10% sodium hydroxide solution until the solution changes from green to red. The aqueous phase is extracted continuously over 24 hours using a 95/5 (v/v) solution of CH$_2$Cl$_2$/EtOH 95/5. The organic phases are washed with a saturated NaCl solution, dried over Na$_2$SO$_4$ and concentrated to dryness. 462 mg of compound (5) are obtained with a yield of 69%.

M(g/mol$^{-1}$): 690.81

TLC: CH$_2$Cl$_2$/EtOH 9/1: R$_f$=0

$^1$H NMR: CDCl$_3$, δ (ppm): 9.05 (6H; dd; 4.4 Hz; 1.9 Hz); 8.97 (2H; d; 4.9 Hz); 8.86 (4H; s); 8.82 (2H; d; 4.9 Hz); 8.16 (6H; d; 4.4 Hz); 8.10 (2H; d; 8.8 Hz); 7.30 (2H; d; 8.8 Hz); 4.37 (2H; t; 6.4 Hz); 3.14 (2H; t; 6.4 Hz); 2.17 (2H; qi; 6.4 Hz); −2.86 (2H; s)

MS: Positive-ion electrospray ionization: (M+H)$^+$=691; [M+2]$^{2+}$/2=346

II-4 [5-(4-(3-(2-1H-pyrrol-3-yl-acetylamino)-1-propoxy)phenyl)-10,15,20-tri-pyridin-4-yl]porphyrin (6)

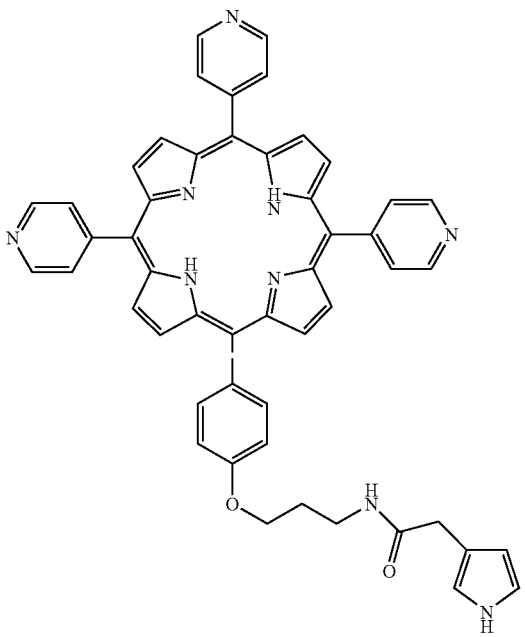

(6)

Under argon, 48 mg (0.38 mmol; 1.2 eq.) of compound (1), 78 mg (0.38 mmol; 1.2 eq.) of dicyclohexyl-carbodiimide (DCC) dried using a rotary vane pump, and 44 mg (0.38 mmol; 1.2 eq.) of N-hydroxysuccinimide (NHS) are dissolved in 2 mL CH$_2$Cl$_2$. The reaction medium is stirred at ambient temperature for 1 hour to obtain the activated ester. A solution of 221 mg (0.32 mmol; 1 eq.) of compound (5) in 2 mL CH$_2$Cl$_2$, with a few drops of triethylamine, is added slowly. The medium is stirred for 3 hours, then filtered through sintered glass and concentrated to dryness. The mixture obtained is purified by flash chromatography on 50 g of silica using as eluent a 95/5 (v/v) mixture of CH$_2$Cl$_2$/EtOH. 252 mg of compound (6) are obtained.

M (g·mol$^{-1}$): 797.93

TLC: CH$_2$Cl$_2$/MeOH 85/15: R$_f$=0.64

$^1$H NMR 400 MHz: CD$_3$OD, δ (ppm): 8.99 (m); 8.91 (m); 8.29 (m); 8.10 (d; 7.7 Hz); 7.98 (m); 7.38 (d; 7.7 Hz)

UV-Vis: DMF (200-775 nm) λ (nm): 235; 421 (Soret); 516, 550, 591, 650 (Q bands)

MS: Positive-ion electrospray ionization: (M+2NH$_4$$^+$)=830

II-5 Metalation of Compound (6)

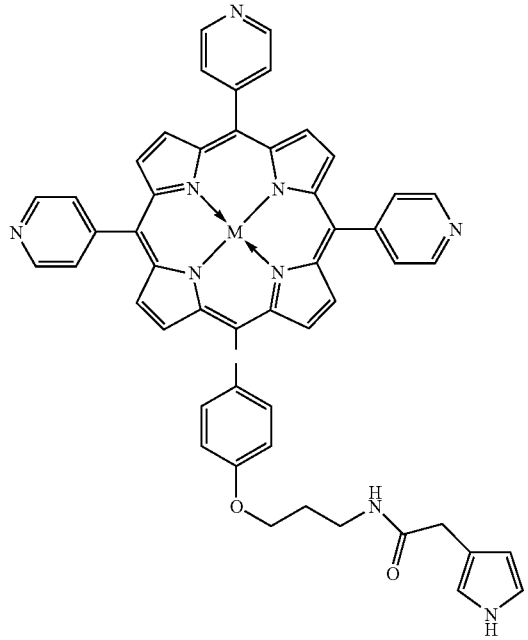

(7)

With M=Co

In 1 mL DMF, 50 mg (63 µmol; 1 eq.) of compound (6) and 80 mg (616 µmol; 10 eq.) of CoCl₂ (dried using a rotary vane pump) are dissolved. The reaction medium is heated at 80° C. for 2 hours, then concentrated to dryness. The mixture is re-dissolved in ethanol and filtered through a sintered glass filter. The solid is collected with a MeOH/CH₂Cl₂ mixture. 50 mg of compound (7) are obtained with M=Co [called (7-Co)], i.e. a yield of 93%.

M (g·mol⁻¹): 854.84

UV-Vis: pyridine (200-775 nm), λ (nm) 255; 341; 440 (Soret); 559 (Q bands)

II-6 Methylation of Compound (7)

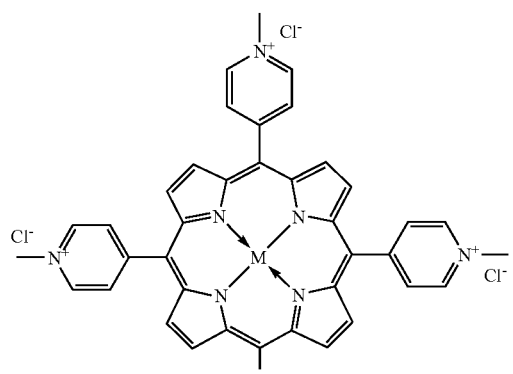

(8)

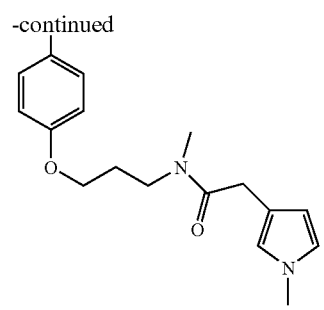

With M=Co

In an enclosed atmosphere 43 mg (0.05 mmol; 1 eq.) of compound (7-Co) are dissolved in 5 mL DMF, and 0.6 mL (10 mmol; 200 eq.) of methyl iodide are added. The reaction medium is stirred 40° C. for 3 hours, then concentrated to dryness and re-dissolved in water. The mixture is passed through an ion exchange column: 2 g Dowec-Cl, then lyophilized. 38 mg of compound (8) are obtained with M=Co, i.e. a yield of 75%. Mass analysis show the presence of the methylated product on all the amines present in the molecule.

M (g·mol⁻¹): 1034.36

MS: Positive-ion electrospray ionization: [M-3Cl]³⁺=927

MALDI: [M−3Cl+3H]=930

UV-Vis: water (200-775 nm), λ (nm): 225; 341; 440 (Soret); 559 (Q bands)

II-7 Methylation of Compound (6)

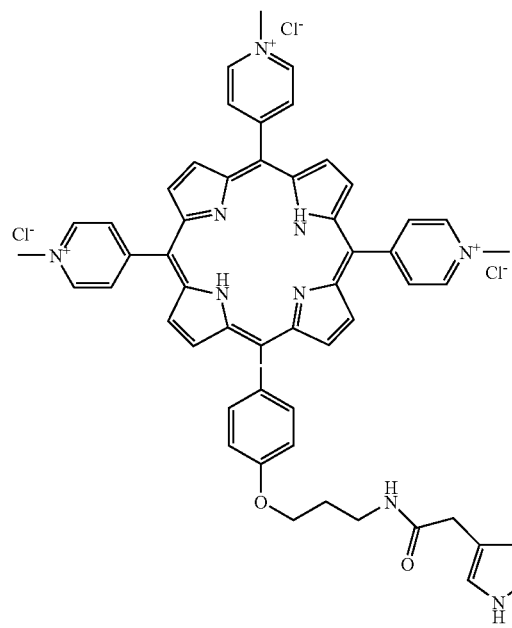

(9)

100 mg (0.125 mmol; 1 eq) of compound (6) are dissolved in 5 mL DMF, then 1.6 mL (25 mmol; 200 eq). methyl iodide are added. The reaction medium is stirred at AT for 18 hours then concentrated to dryness and re-dissolved in water. The mixture is passed through an ion exchange column: 10 g Dowec-Cl, then lyophilized. 100 mg of compound (9) are obtained, i.e. a yield of 84%. Mass analysis shows methylation solely on the pyridiniums.

M(g·mol$^{-1}$): 949.39

$^1$H NMR: CD$_3$OD at 318 K, δ (ppm): 9.99 (6H); 9.73, 9.61 (8H); 9.54 (6H); 8.63 (2H); 7.89 (2H); 7.4 (1H); 7.1 (1H); 6.6 (1H); 5.43 (9H); 4.86 (2H); 4.09 (2H); (3.1); 2.70 (2H).

UV-Vis: water (200-800 nm), λ (nm): 242; 426 (Soret); 522 (Q bands)

MS: M/Z electrospray (M-1Cl/2)=877

II-8 Metalation of Compound (9)

(10)

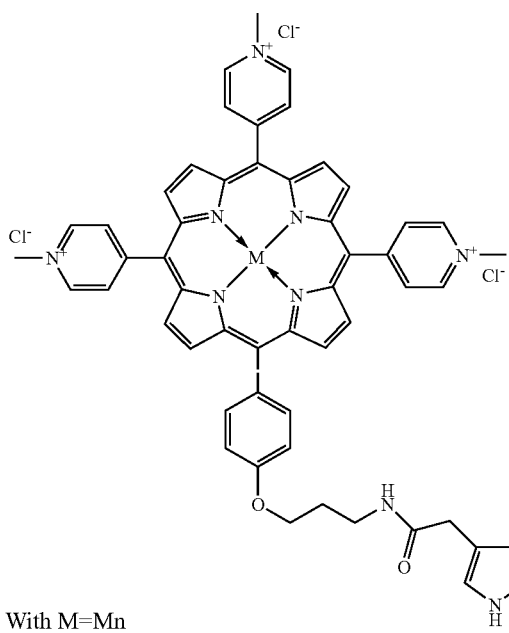

With M=Mn

In 20 mL water, 50 mg (53 mmol; 1 eq.) of compound (9) and 85 mg (527 µmol; 10 eq.) of MnCl$_2$.2H$_2$O are dissolved. The reaction medium is heated under reflux for 5 hours then concentrated to dryness. The mixture is dissolved in minimum methanol, precipitated with acetonitrile and filtered through a sintered glass filter. The solid is collected with a MeOH/H$_2$O mixture.

M (g·mol$^{-1}$): 1002.31

UV-Vis: water (200-800 nm), λ (nm): 250; 438 (Soret); 550 (Q bands)

III—Synthesis of Porphyrin Substituted by 3 Different Groups

III-1 4-(4-formylphenoxy)butyronitrile (11)

(11)

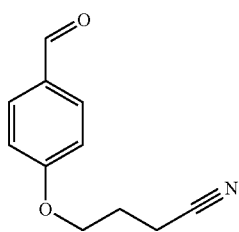

Under argon, 2.44 g (20 mmol; 1 eq.) of 4-hydroxybenzaldehyde are dissolved in 20 mL DMF, and 5.53 g (40 mmol; 2 eq.) of K$_2$CO$_3$ are added. After 1 hour's stirring at 70° C., the medium becomes pink. Using a dropping funnel, a solution of 2.4 mL (24 mmol; 1.2 eq.) of 4-bromobutyronitrile in 6 mL DMF are added slowly. The reaction medium is stirred 1 hour at 70° C. then 2 hours at 90° C. After cooling, the medium is filtered through a sintered glass filter. The filtrate is diluted with dichloromethane until precipitation, then filtered again through a sintered glass filter. The new filtrate is concentrated to dryness then re-dissolved in dichloromethane. The organic phase is washed twice in water then with a saturated NaCl solution, dried over Na$_2$SO$_4$ and concentrated to dryness. 4.15 g of compound (11) are obtained and used without any additional purification (quantitative yield).

M (g·mol$^{-1}$): 189.22

TLC: CH$_2$Cl$_2$/MeOH 9/1: R$_f$=0.55

$^1$H NMR: CDCl$_3$, δ (ppm): 9.82 (1H); 7.77 (2H; d; 8.8 Hz); 6.94 (2H; d; 8.8 Hz); 4.11 (2H; t; 6.3 Hz); 2.56 (2H; t; 6.3 Hz); 2.12 (2H; qi; 6.3 Hz)

III-2 4-[4-(bis-(1H-pyrrol-2-yl)methyl)phenoxy]butyronitrile (12)

(12)

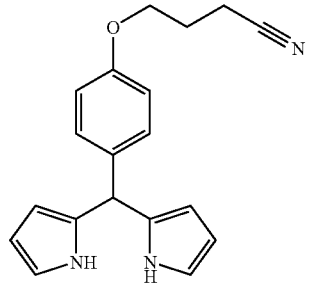

Under argon, in 14 mL (195.5 mmol; 25 eq.) of (distilled) pyrrole, 1.48 g (7.8 mmol; 1 eq.) of compound (11) are dissolved. 60 µL (0.8 mmol; 0.1 eq.) of TFA are added. The reaction medium is stirred at AT for 10 min. 10 mL (1 mmol) of a 0.1N sodium hydroxide solution are added. After diluting the solution with water, the aqueous phase is extracted with ethyl acetate. The organic phase is washed with water and with a saturated NaCl solution, dried over Na$_2$SO$_4$ and concentrated to dryness. The mixture obtained is purified by chromatography on 100 g of silica using as eluent a 95/5 (v/v) solution of CH$_2$Cl$_2$/MeOH. Approximately 1 g of compound (12) is obtained i.e. a yield of around 42%.

M (g·mol$^{-1}$): 305.38

TLC: CH$_2$Cl$_2$/MeOH 99/1: R$_f$=0.57

$^1$H NMR: CDCl$_3$, δ (ppm): 8.00 (2H); 7.21 (2H; d; 8.8 Hz); 6.94 (2H; d; 8.8 Hz); 6.69 (2H; m); 6.25 (2H; m); 5.97 (2H; m); 5.41 (1H; s); 4.07 (2H; t; 6.3 Hz); 2.56 (2H; t; 6.3 Hz) 2.12 (2H; qi; 6.3 Hz).

III-3 2-[3-[4-(bis-(1H-pyrrol-2-yl)methyl)phenoxy]propyl]isoindole-1,3-dione

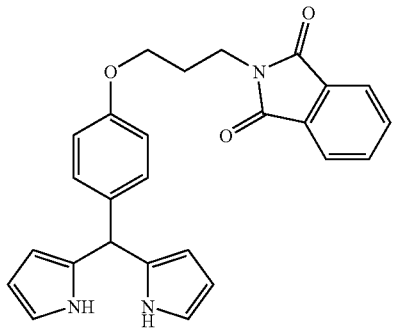

(13)

Under argon, in 35 mL (500 mmol; 25 eq.) of (distilled) pyrrole, 6.19 g (20 mmol; 1 eq.) of compound (3) are dissolved. 150 μL (2 mmol; 0.1 eq.) of TFA are added. The reaction medium is stirred at AT for 5 min. 2.4 g (60 mmol; 3 eq.) of powder sodium hydroxide are added. The reaction medium is stirred at AT for 30 min, filtered through a sintered glass filter, washed with hexane and concentrated to dryness. The mixture obtained is purified by chromatography on 400 g silica using as eluent a 995/5 (v/v) mixture of CH$_2$Cl$_2$/MeOH. Approximately 1.52 g of compound (13) are obtained i.e. a yield of around 18%.

M (g·mol$^{-1}$): 425.49

TLC: CH$_2$Cl$_2$/MeOH 99/1: R$_f$=0.6

$^1$H NMR: CDCl$_3$, δ (ppm): 8.21 (2H); 7.85 (2H; m); 7.75 (2H; m); 7.11 (2H; d; 8.3 Hz); 6.76 (2H; d; 8.3 Hz); 6.70 (2H; m); 6.20 (2H; m); 5.94 (2H; m); 5.40 (1H; s); 4.02 (2H; t; 6.1 Hz); 3.92 (2H; t; 6.1 Hz); 2.21 (2H; qi; 6.1 Hz).

III-4 [5-[4-(3-(N-phthalimide)-1-propoxy)phenyl]-15-[4-(3-cyano-1-propoxy)phenyl]-10,20-tri-pyridin-4-yl]porphyrin (14)

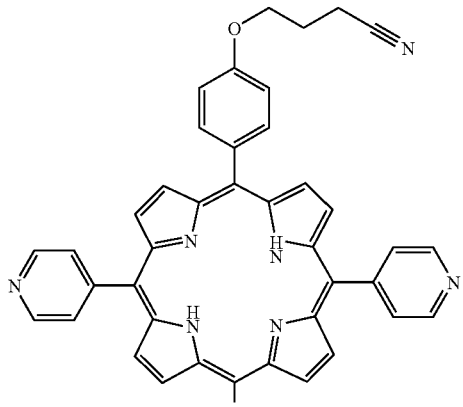

(14)

-continued

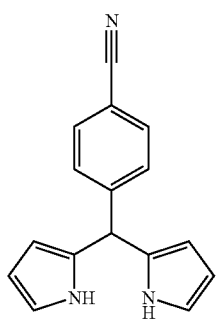

In 500 mL of CH$_2$Cl$_2$, 1.00 g (3.27 mmol; 1 eq.) of compound (12), 1.39 g (3.27 mmol; 1 eq.) of compound (13) and 0.6 mL (6.55 mmol; 2 eq) of 4-pyridine-carboxaldehyde are dissolved. 2 mL (26.2 mmol; 8 eq.) of TFA are added. The reaction medium is stirred at AT for 30 min. 250 mL of THF, 3.6 mL (26.2 mmol; 8 eq.) of triethylamine, then a solution of 2.22 g (9.82 mmol; 3 eq.) of DDQ in THF are added. The reaction medium is stirred at AT for 3 hours, then concentrated to dryness. After re-dissolving in dichloromethane, TFA is added until neutralization. After concentrating to dryness and a first filtration on silica with a 97/3 mixture of CH$_2$Cl$_2$/EtOH, the mixture is purified by chromatography on a column of 350 g silica with a mixture of CH$_2$Cl$_2$ containing increasing proportions of EtOH (from 0.3% to 0.5%). The fraction obtained is analyzed by proton NMR and shows the presence of the right product.

M (g·mol$^{-1}$): 903.02

1H NMR: CDCl$_3$, δ (ppm): 8.85 (8H; s); 8.12 (2H; d; 8.8 Hz); 8.06 (2H; d; 8.8 Hz); 7.91 (2H; dd; 2.9 Hz; 5.4 Hz); 7.74 (2H; dd; 2.9 Hz; 5.4 Hz); 7.26 (2H; d; 8.8 Hz); 7.18 (2H; d; 8.8 Hz); 4.39 (2H; t; 6.2 Hz); 4.33 (2H; t; 6.5 Hz); 4.08 (2H; t; 6.5 Hz); 2.78 (2H; t; 6.2 Hz); 2.36 (4H; m).

IV—Synthesis of a Di-Anionic Porphyrin Functionalized with a Pyrrole

Synthesis was conducted in accordance with SCHEMES 7 to 11 previously described.

IV-1 Synthesis of 5-(4-cyanophenyl)dipyrromethane (15)

(15)

The synthesis of 5-(4-cyanophenyl)dipyrromethane (15) is conducted by reaction of 4-cyanobenzaldehyde for 10 minutes at ambient temperature, with a pyrrole/aldehyde ratio of 25/1 and 0.1 eq TFA.

Under argon, 3.28 g of 4-cyanobenzaldehyde (25 mmol; 1 eq.) are dissolved in 44 mL (630 mmol; 25 eq.) of (distilled) pyrrole, then 0.2 mL (2.5 mmol; 0.1 eq.) of TFA are added. The reaction medium is stirred at ambient temperature (AT) for 10 min. An aqueous NaOH solution (30 mL; 0.1M) is added. The mixture is diluted in ethyl acetate. The organic phase is separated by decanting, washed with water until neutralization then saturated with a NaCl solution, dried over $Na_2SO_4$ and concentrated to dryness. The mixture obtained (7.83 g) is purified by chromatography on 400 g of silica using $CH_2Cl_2$ as eluent.

Molar mass (g·mol$^{-1}$): 247.30 ($C_{16}H_{13}N_3$)
TLC: $CH_2Cl_2$: $R_f$=0.4
$^1$H NMR: CDCl$_3$, δ (ppm): 8.02 (2H; s); 7.60 (2H; d; 8 Hz); 7.31 (2H; d; 8 Hz); 6.73 (2H; d; 3 Hz); 6.16 (2H; d; 3 Hz); 5.85 (2H; m); 5.53 (1H; s).

IV-2 Construction of the Porphyrin Cycle (16)

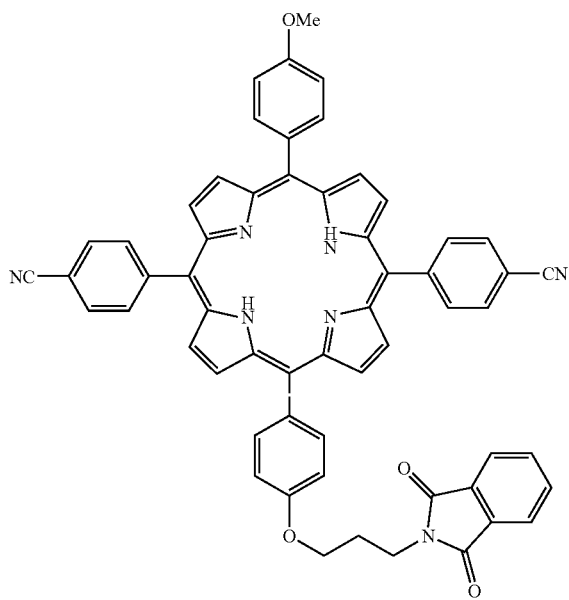

(16)

Under argon, 2.47 g (10 mmol; 2 eq.) of 5-(4-cyanophenyl) dipyrromethane (15) 4-methoxybenzaldehyde (0.68 g; 5 mmol; 1 eq.) and 1.55 g of 4-[1-propoxy-3-(N-phthalimide)] benzaldehyde (5 mmol; 1 eq.) are dissolved in $CH_2Cl_2$ (1 L). 2.3 mL of TFA (30 mmol; 6 eq.) are added. The reaction medium is stirred at ambient temperature for 30 min. Next, 250 mL THF, 7 mL Et$_3$N (50 mmol; 10 eq.) then a DDQ solution (3.41 g; 15 mmol; 3 eq.) in THF (250 mL) are added. The reaction medium is stirred at ambient temperature for 2 hours, then concentrated to dryness. The mixture (16.8) is purified by filtration on silica gel with a 99/1 mixture of $CH_2Cl_2$/EtOH. The product obtained (3.53 g) is purified by chromatography on a column of 400 g silica with a $CH_2CL_2$ mixture. The product is purified once more (1.3 g) on silica gel (200 g) with $CH_2Cl_2$. The porphyrin (16) (950 mg) is obtained.

M (g·mol$^{-1}$): 898.00 ($C_{58}H_{39}N_2O_4$)
TLC: $CH_2Cl_2$/MeOH 99/1: $R_f$=0.41
$^1$H NMR: CDCl$_3$, δ (ppm): 8.94-8.97 (4H; 2d; 4.5 Hz); 8.74-8.77 (4H; 2d; 4.5 Hz); 8.28 (4H; d; 8 Hz); 8.13 (2H; d; 8.5 Hz); 8.07 (2H; d; 8.5 Hz); 7.98 (4H; d; 8 Hz); 7.78 (2H; dd; 5.5 Hz; 3 Hz); 7.58 (2H; dd; 5.5 Hz; 3 Hz); 7.29 (2H; d; 9 Hz); 7.16 (2H; d; 9 Hz); 4.24 (2H; t; 6 Hz); 4.07 (3H; s) 4.01 (2H; t; 6 Hz); 2.33 (2H; qi; 6 Hz); −2.83 (2H; wide s).

Mass Spectrometry MS: Positive-ion electrospray ionization: 188.0 (100); [M]+=898.3 (30); [M+H]$^+$=899.3 (19)

UV-Vis spectroscopy: $CH_2Cl_2$ (350-750 nm), λ (nm): 422 (Soret); 518; 552; 592; 648

IV-3 Deprotection of the Amine Function and Preparation of the Porphyrin (17)

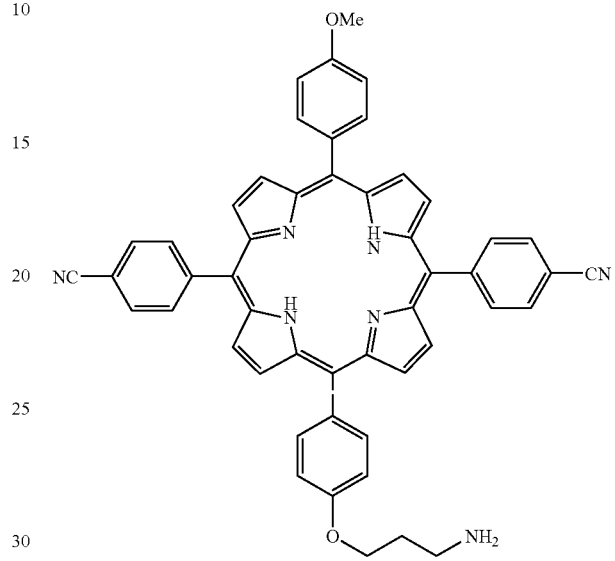

(17)

The amine function is obtained by deprotection with hydrazine, making different modifications compared with the operating conditions used for the preceding porphyrins: large excess hydrazine is used (100 equivalents) and the reaction medium is heated at 60° C. for 24 hours.

The porphyrin (16) (917 mg; 1.02 mmol; 1 eq.) is dissolved in 20 mL $CH_2Cl_2$, then 40 mL MeOH. 5 mL of 64% $NH_2NH_2$ (102 mmol; 100 eq) is added. The reaction medium is stirred at 60° C. for 24 hours. A 10% solution of HCl is added until the mixture turns green. The solution is then filtered. Water is added until neutralization. The solution becomes violet. $CH_2Cl_2$ and MeOH are evaporated. The solution is extracted several times with $CH_2Cl_2$. The organic phase is washed several times with water, dried then concentrated to dryness.

It is noted that with this di-nitrile porphyrin (17) it is not necessary to use a continuous extraction assembly for purification by washing with water. Under NMR spectrometry the two signals characteristic of the phthalimide group are seen to disappear at 7.9 and 7.7 ppm, and under mass spectrometry a majority peak at 711.2 is observed corresponding to the molecule fragmented at the ether bridge of the propyloxy chain, as well as a peak corresponding to [M+H]$^+$ at 768.3 (15%).

M (g·mol$^{-1}$): 767.90 ($C_{50}H_{37}N_2O_2$)
TLC: $CH_2Cl_2$/MeOH 95/5: $R_f$~0
$^1$H NMR: CDCl$_3$, δ (ppm): 8.93-8.94 (4H; 2d; 4.5 Hz); 8.73-8.74 (4H; 2d; 4.5 Hz); 8.31 (4H; d; 7.5 Hz); 8.12 (2H; d; 8 Hz); 8.10 (2H; d; 6 Hz); 8.04 (4H; d; 7.5 Hz); 7.30 (2H; d; 8H); 7.27 (2H; d; 6 Hz); 4.34 (2H; t; 6.5 Hz); 4.10 (3H; s) 3.09 (2H; t; 6.5 Hz); 2.34 (2H; qi; 6.5 Hz); −2.78 (2H; s)

Mass spectrometry (MS) by MALDI-TOF: [(Porphyrin-O.)+2H]$^+$=711.2 (100); [M+H]$^+$=768.3 (15)

Fourier Transform Infrared Spectrometry (FTIR): U (cm$^{-1}$): 3315; 2930; 2228; 1604; 1504; 1472; 1245; 1173; 982; 966; 790; 734

IV-4 Peptide Coupling Between the Porphyrin (17) and the Carboxylic Acid Derivative of Pyrrole, Preparation of Porphyrin (18)
The peptide coupling of the porphyrin-amine (17) with the pyrrole—non-protected acid is conducted in the presence of DCC/NHS according to SCHEME 16.
SCHEME 16
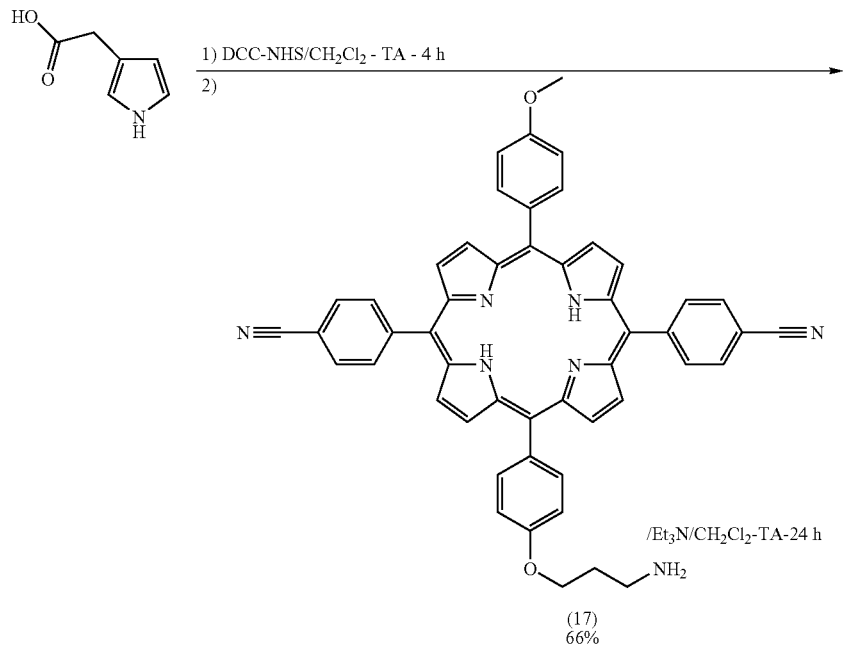
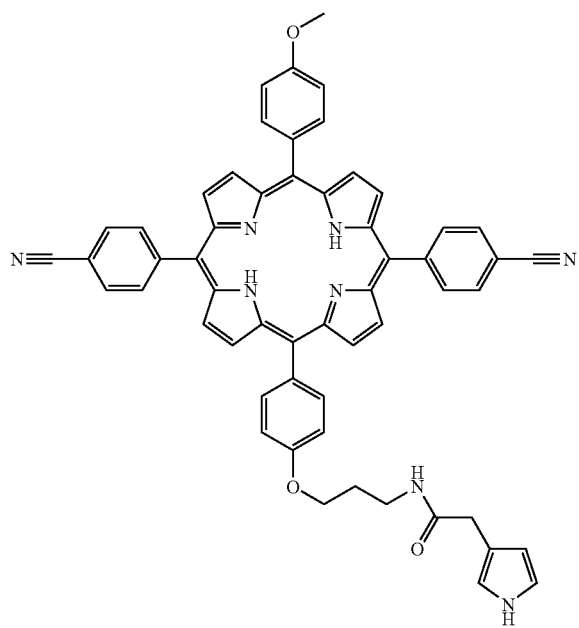

Purification is performed on a neutral alumina gel, to prevent any polymerization of the compound (18), which would occur on silica gel, and to avoid adding triethylamine to the eluent (as previously). The porphyrin was characterized by NMR spectrometry for purity, and by MALDI mass spectrometry through the presence of a non-characterized majority peak at 907.0 as well as peaks corresponding to [M]$^+$ and [M+H]$^+$ at 875.1 (65%) and 876.1 (50%) respectively.

IV-5 Metalation and Hydrolysis Reactions of the Nitrile Groups of Compound (18)

To obtain the metallated and di-anionic porphyrin, the two reactions: metalation and hydrolysis can be performed without any order of preference. However, if it is desired to complex the porphyrin with different metals, it is more advantageous to perform hydrolysis firstly. Nonetheless, the carboxylate functions of the molecule, in this case, might complex the metal salts and raise problems of reactivity and purification. Metalation was therefore conducted before hydrolysis.

IV-5-1 Metalation and Preparation of the Porphyrins (19)

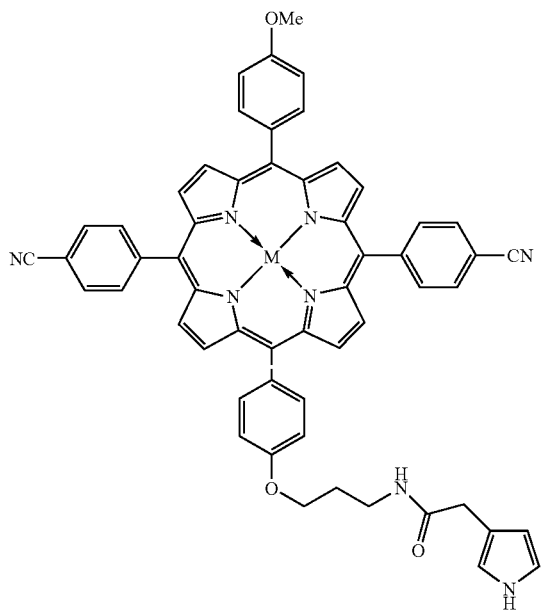

The porphyrin (18) reacts with the acetate of the desired metal salt in DMF at 40° C. for 24 hours.

Several metalloporphyrins complexed by the desired metal: cobalt, iron, manganese and zinc, were synthesized with yields of 94% to 100% depending on the metal. Addition of the metal was ascertained under UV-Vis spectrometry, by observing disappearance of two of the four Q bands, and shifting of the Soret band: from 422 nm to 419 nm for cobalt, to 414 nm for iron, to 466 nm for manganese and to 428 nm for zinc. Under MALDI mass spectrometry, cobalt porphyrin exhibits a majority peak corresponding to [M+H]$^+$ at 932.3 and the manganese porphyrin a majority peak corresponding to [M]$^+$ at 927.3.

Operating Mode

Operating mode with M=Co

Compound (18) (350 mg; 0.4 mmol; 1 eq) and Co(acetate)$_2$. 4H$_2$O (5 g; 20 mmol; 50 eq) are dissolved in DMF (20 mL) under argon. The reaction medium is heated at 50° C. for 24 hours, then concentrated to dryness. The product is dissolved in ethyl acetate, and the organic phase is washed several times with water. After concentration, compound (19)-Co (355 mg) is obtained.

M (g·mol$^{-1}$): 931.93 (C$_{56}$CoH$_{40}$N$_8$O$_3$)
TLC: CH$_2$Cl$_2$/MeOH 95/5: R$_f$=0.35
MS: MALDI-TOF: [M+H]$^+$=932.3 (100); [M+Na]$^+$=954.3 (59); [M]$^+$=931.3 (52)
UV-Vis: DMF (350-750 nm). λ (nm): 419 (Soret); 532

With M=Fe

Compound (18) (50 mg; 57 μmol; 1 eq) and FeCl$_2$.4H$_2$O (568 mg; 2.9 mmol; >50 eq) are dissolved in DMF (5 mL) under argon. The reaction mixture is heated at 50° C. for 48 hours, then concentrated to dryness. The product is dissolved in ethyl acetate and the organic phase is washed several time in water. After concentration, compound (19)-Fe (50 mg) est obtenu.

M (g·mol$^{-1}$): 928.84 (C$_{56}$H$_{40}$FeN$_8$O$_3$)
TLC: CH$_2$Cl$_2$/MeOH 85/15: R$_f$=0.67
MS: MALDI-TOF: 568.1 (100); [M+Na]$^+$=951.2 (33); [M+H]$^+$=929.3 (31); [M+$^{35}$Cl]$^+$=963.3 (16)
UV-Vis: DMF (350-750 nm). λ (nm): 414 (Soret); 574; 622; 649

IV-5-2 Hydrolysis of the Nitrile Groups and Preparation of the Metalloporphyrins (20)

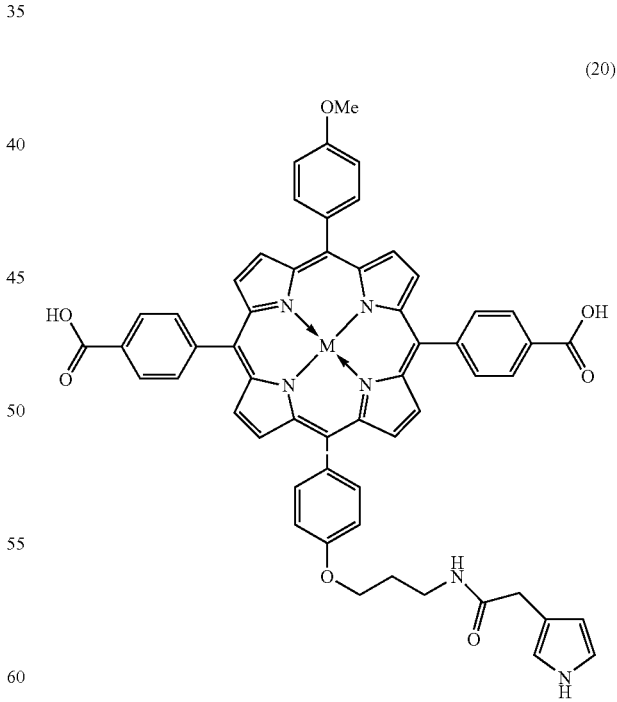

The hydrolysis reactions of the nitrile groups into carboxylic acids are generally conducted in an acid medium, such as in the work by S. Gobbi et al [Gobbi S., Rampa A., Bisi A., Belluti F., Valenti P., Caputo A., Zampiron A. and Carrara M., "Synthesis and Antitumor Activity of New Derivatives of Xanthen-9-one-4-acetic Acid", *Journal of Medicinal Chemistry*, 2002, 45, p. 4931-4939]. However for the preparation of compounds (20) in which a pyrrole substituent, highly sensitive to the acid medium, is present on the molecule, hydrolysis is advantageously conducted in a basic medium [Cignarella G., Barlocco D., Rossi G. and Rossi E., "Spirocyclopropane Carboxylic Acids Derived from 1-Tetralone and 4-Chromanone and their Conversion to the Corresponding Pyridazinones", *Synthesis*, 1990, p. 160-162; Fürstner A., Stelzer F., Rumbo A. and Krause H., "Total Synthesis of the Turrianes and Evaluation of Their DNA-Cleaving Properties", *Chemistry—A European Journal*, 2002, 8, p. 1856-1871]. All the protocols are similar: HO⁻ as base, water-alcohol mixture and heating under reflux. The only difference lies in the strength of this base, determined in relation to the counter-cation used ($K^+$, $Na^+$, $L^+$).

Analysis by infrared spectrometry shows full disappearance of the band at 2228 cm$^{-1}$, characteristic of nitrile groups.

Operating Mode with M=Co

Compound (19)-Co (355 mg; 0.4 mmol; 1 eq) is dissolved in a KOH solution (1N) in methanol (20 mL). The reaction mixture is heated at 50° C. for 24 hours, then concentrated to dryness. The product is dissolved in water and ethyl acetate is added. A 1N solution of HCl is added until neutralization. During neutralization the pH is controlled to prevent polymerization of the pyrrole.

The product is extracted with ethyl acetate and the organic phase is washed with water. After concentration, compound (20)-Co (237 mg) is obtained.

M (g·mol$^{-1}$): 969.93 ($C_{56}CoH_{42}N_6O_2$)

MS: MALDI-TOF: [(PorphyrinCN/COOH)+H+31]$^+$=982.2 (100); [M+31]$^+$=1000.2 (97); [M+H+31]$^+$=1001.2 (86); [(PorphyrinCN/COOH—O.)+H]$^+$=785.2 (86); [(PorphyrinCN/COOH)+31]$^+$=981.2 (25); [(Porphyrin-O.)+H]$^+$=804.2 (25); [M]$^+$=969.2 (21); [(PorphyrinCN/COOH)+H]$^+$=951.2 (19); [M+H]$^+$=970.2 (16)

UV-Vis: DMF (350-750 nm). λ (nm): 420 (Soret); 536

FTIR: υ (cm$^{-1}$): 3381; 2924; 1714; 1655; 1247; 1017; 952; 757

V—Synthesis of a Di-Cationic Porphyrin Functionalized with a Pyrrole (26)

The synthesis pathway for the di-cationic monomer (26) was given previously in SCHEME 15.

V-1 Synthesis of 5-(4-pyridyl)dipyrromethane (21)

The synthesis of 5-(4-pyridyl)dipyrromethane can be conducted following different methods. The operating conditions used by J.-W. Ka and C.-H. Lee [Ka J.-W. and Lee C.-H., "Optimizing the synthesis of 5,10-disubstituted tripyrromethanes", *Tetrahedron Letters*, 2000, 41, p. 4609-4613] entail stirring at ambient temperature for 5 minutes, with a pyrrole/aldehyde ratio of 5/1 and using 0.1 equivalent TFA. The low yield, 35%, they obtained is due to protonation of the nitrogen heterocycle, which reduces the quantity of acid catalyst in the medium and gives numerous secondary products.

D. Gryko and J. S. Lindsey [Gryko D. and Lindsey J. S., "Rational Synthesis of Meso-Substituted Porphyrins Bearing One Nitrogen Heterocyclic Group", *Journal of Organic Chemistry*, 2000, 65, p. 2249-2252] proposed another protocol without using a Brönsted acid. They conducted synthesis of 5-(4-pyridyl)dipyrromethane with a yield of 58%, by heating a 14/1 mixture of pyrrole/aldehyde to 85° C. for 15 hours.

5-(4-pyridyl)dipyrromethane (21) was prepared following the operating conditions set forth under SCHEME 17, without acid at high temperature.

SCHEME 17

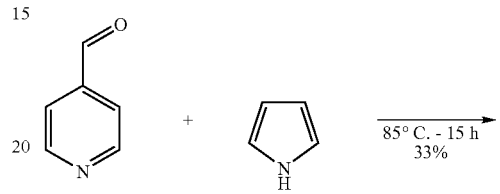

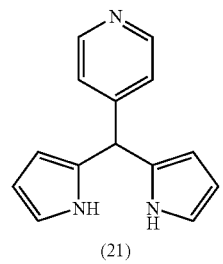

(21)

V-2 Construction of the Porphyrin Cycle (22)

Construction of the porphyrin cycle was carried out under the same operating conditions described previously by D. T. Gryko and M. Tasior (5-pyridyldipyrromethane with equivalents of TFA for 30 minutes at ambient temperature) using two different aldehydes: compound (6) and 4-methoxybenzaldehyde according to SCHEME 18.

SCHEME 18

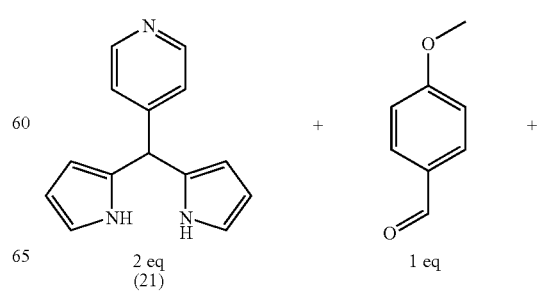

2 eq
(21)

1 eq

53
-continued

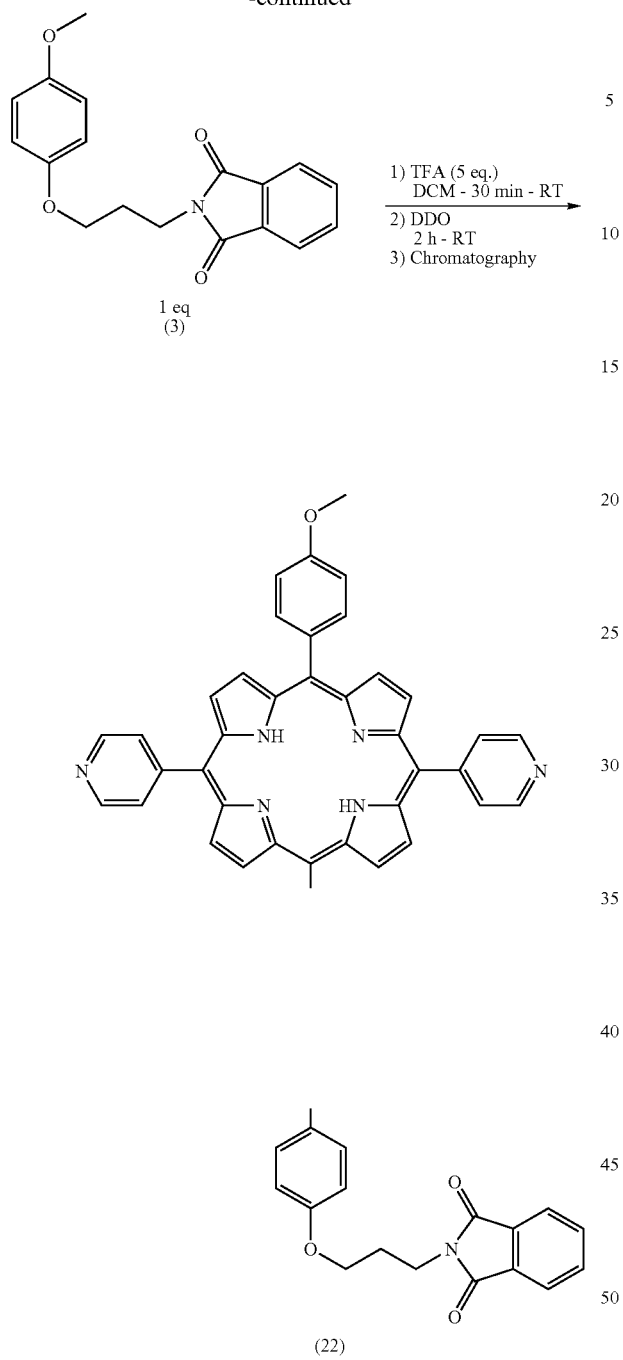

SCHEME 19

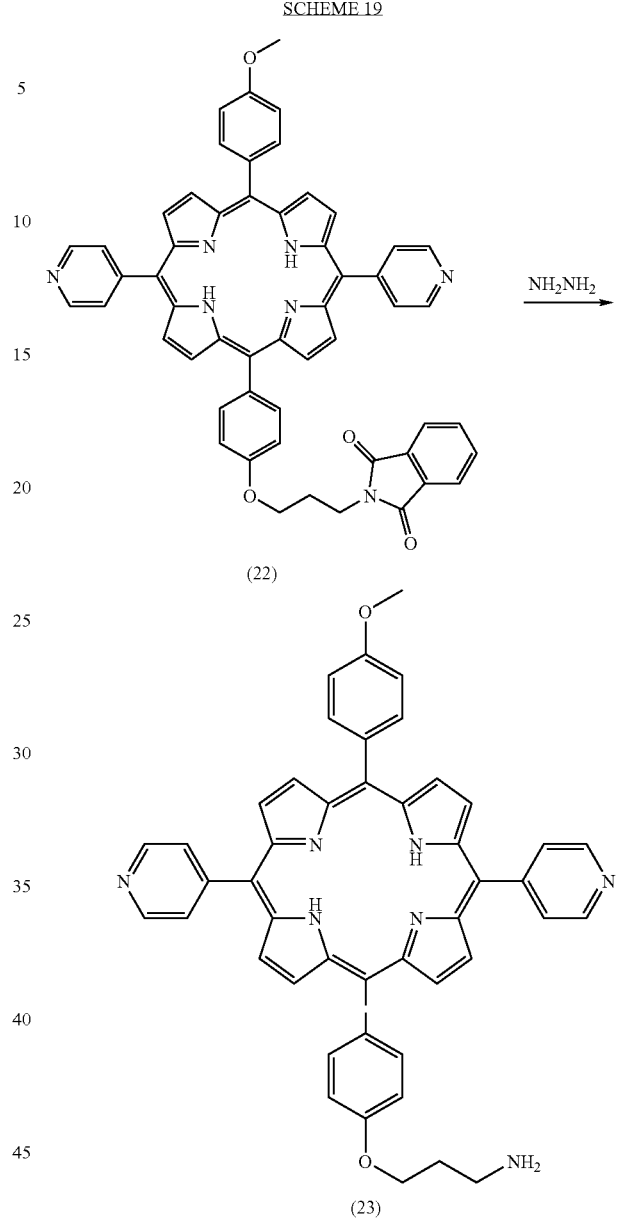

The desired porphyrin (22) is then isolated from the mixture of three porphyrins by chromatography on silica. The porphyrin was characterized by NMR spectrometry.

V-3 Deprotection of the Amine Function

The amine function of porphyrin (23) is obtained by deprotection with 100 equivalents of hydrazine (SCHEME 19).

The porphyrin (23) was characterized by NMR and MALDI mass spectrometry, with the presence of a majority peak corresponding to $[M+H]^+$ at 720.3.

V-4 Peptide Coupling Between the Amino Porphyrin (23) and the Carboxylic Acid Derivative of Pyrrole (1)

Peptide coupling of the amine-porphyrin (23) with the non-protected pyrrole acid (1) is conducted in the presence of DCC/NHS (SCHEME 20), under the same operating conditions as for the previous monomers.

SCHEME 20
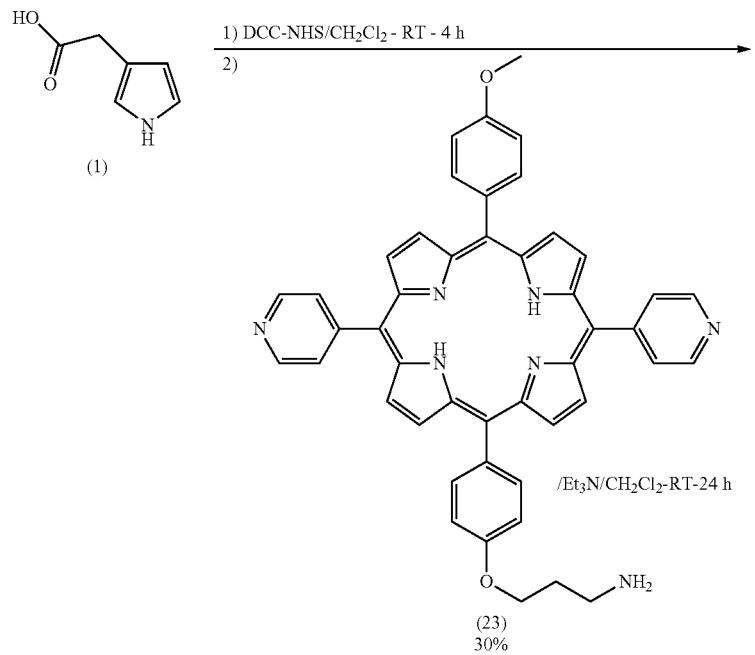
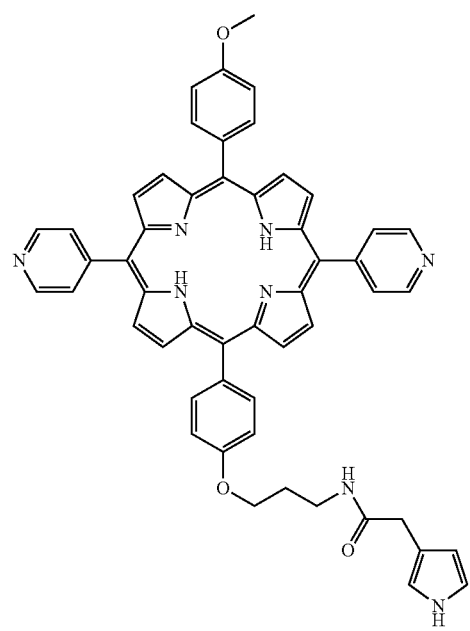

Coupling was monitored by NMR and MALDI mass spectrometry, with the presence of a majority peak at 850.3 corresponding to [M+Na+H]$^{2+}$ and a peak at 849.3 (87%) corresponding to [M+Na]$^+$.

V-5 Metalation and Permethylation Reactions of the Pyridyl. Groups

As for the preceding monomer, the metalation and permethylation reactions can be performed with no order of preference, however it is always preferable to methylate firstly if it is desired to use different metals. It was therefore chosen to conduct the permethylation reaction then to separate different batches for different metals, and finally to metallate the hydrosoluble porphyrin.

V-5-1 Methylation

The permethylation reaction of the two pyridyl groups is conducted with a large excess of methyl iodide at 40° C. (SCHEME 21).

SCHEME 21

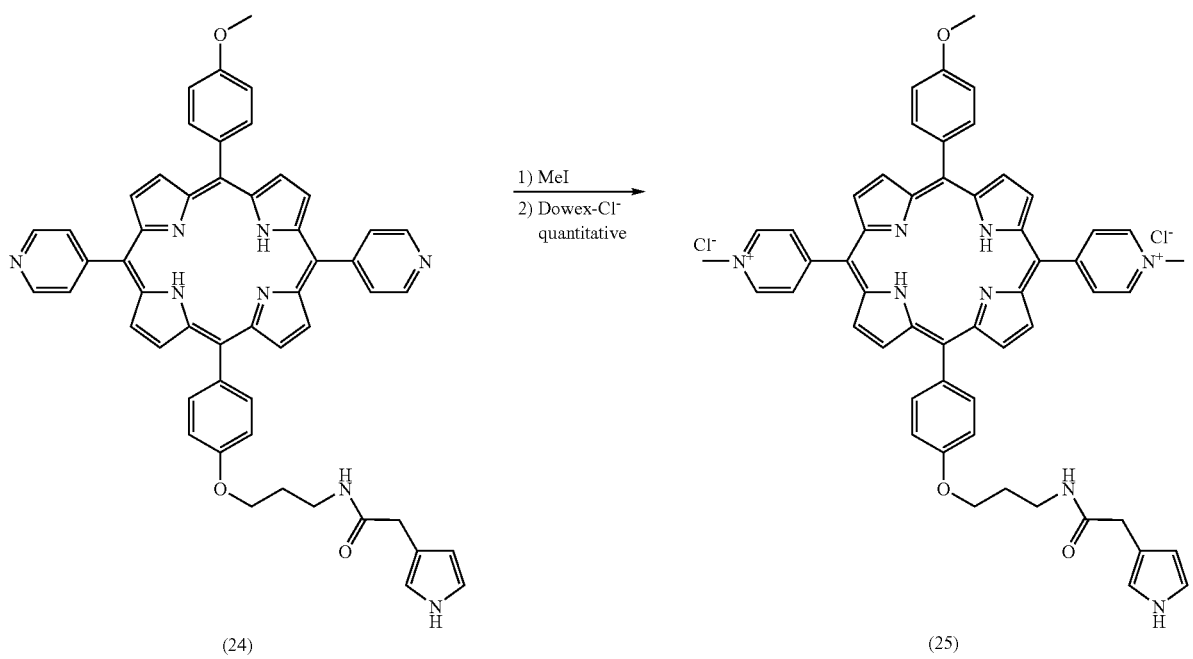

To make the porphyrin hydrosoluble, the di-iodine compound is passed through a Dowex-Cl⁻ column to exchange the iodides into chloride counter-anions. The reaction is quantitative.

Under atmosphere, the compound (24) (26 mg; 31 μmol; 1 eq) is dissolved in DMF (6 mL), and iodomethane (0.4 mL; 6.3 mmol; 200 eq) is added. The reaction mixture is stirred at ambient temperature for 48 hours, then concentrated to dryness and dissolved in water. The mixture is passed through a Dowex-Cl ion exchange resin column and lyophilized. 57 mg of compound (25) are isolated.

M (g·mol⁻¹): 927.94 ($C_{54}H_{48}Cl_2N_8O_3$)

MS: MALDI-TOF: [M(−2Cl)+Na]⁺=879.4 (100); [(Porphyrin-O.)(−2Cl)+H]⁺=692.3 (10)

UV-Vis: DMF (350-750 nm), λ (nm): 428 (Soret); 521; 559; 599; 655

V-5-2 Metalation

Metalation of the porphyrin is performed with a very large excess of the acetate of the desired metal salt, in DMF at 40° C. (SCHEME 22).

solved in DMF (5 mL) under argon. The reaction mixture is heated at 50° C. for 48 hours, and concentrated to dryness. The mixture is dissolved in water. To precipitate the porphyrin, $NH_4PF_6$ is added. After filtering and washing with water, the product is dissolved in water. The mixture is passed through a Dowex-Cl ion exchange resin column and lyophilized. 35 mg of compound (26)-Mn are isolated.

M (g·mol⁻¹): 980.86 ($C_{54}H_{46}Cl_2MnN_8O_3$)

MS: MALDI-TOF: [M(−2Cl)+Na−H]⁺=931.3 (100); [M(−2Cl)+Na]⁺=932.3 (60); [M(no-metalled)(−2Cl)+Na]⁺= 879.4 (60); [(Porphyrin-O.)(−2Cl)+H]⁺=759.3 (25)

UV-Vis: DMF (350-750 nm), λ (nm): 429; 468 (Soret) 524; 573; 632

B. ELECTROCHEMICAL CHARACTERIZATIONS

Reference is made to appended FIGS. 1 to 7.

FIG. 1 Voltammograms of the meso-tetramethyl-pyridiniumyl-porphyrins complexed with different metals in an aqueous medium, in the presence of 0.5M NaCl. Scan rate 100 mV/s.

SCHEME 22

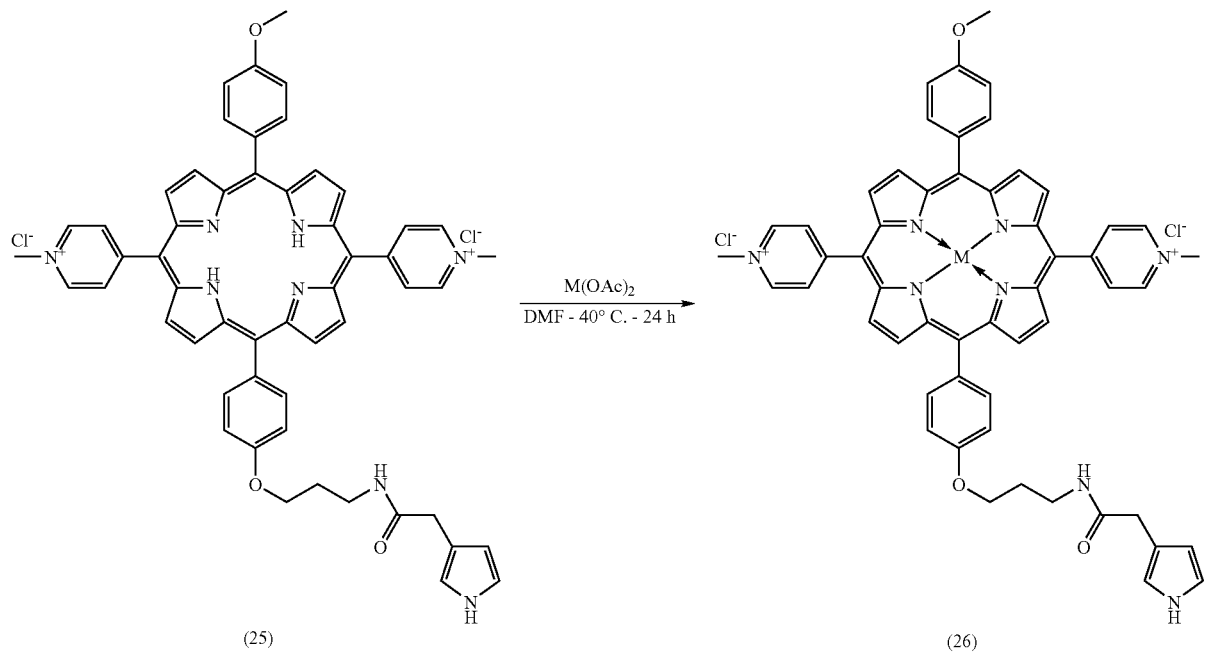

The insertion of the metal in the macrocycle was verified under UV-Vis spectrometry, by shifting of the Soret band from 428 nm to 468 nm.

The separation of the remaining metal salts from the hydrosoluble metalloporphyrin is made by precipitation. In an aqueous solution, excess hexafluorophosphate anions is added, which leads to precipitation of the porphyrin. After filtering, a pass through a Dowex-Cl⁻ column allows a soluble metalloporphyrin to be collected with chloride counter-anions. In fact, iodide counter-anions are sufficient to make the porphyrin insoluble in an aqueous solution. Therefore it may be of interest not to pass the molecule (25) through the Dowex-Cl⁻ column, after methylation, to gain a step.

Figure 2:
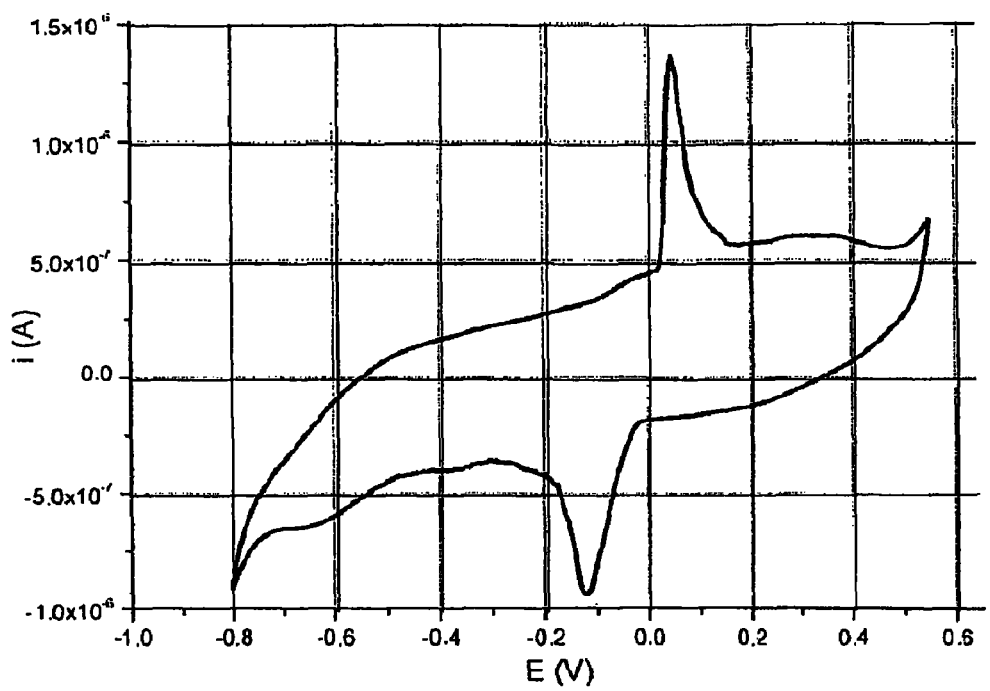

The compound (25) (47 mg; 51 μmol; 1 eq) and dried Mn(acetate)₂.4H₂O (750 mg; 3.1 mmol; 100 eq) are dis- FIG. 2 Voltammogram of a polypyrrole film functionalized by a zinc tri-cationic porphyrin.

Figure 3:
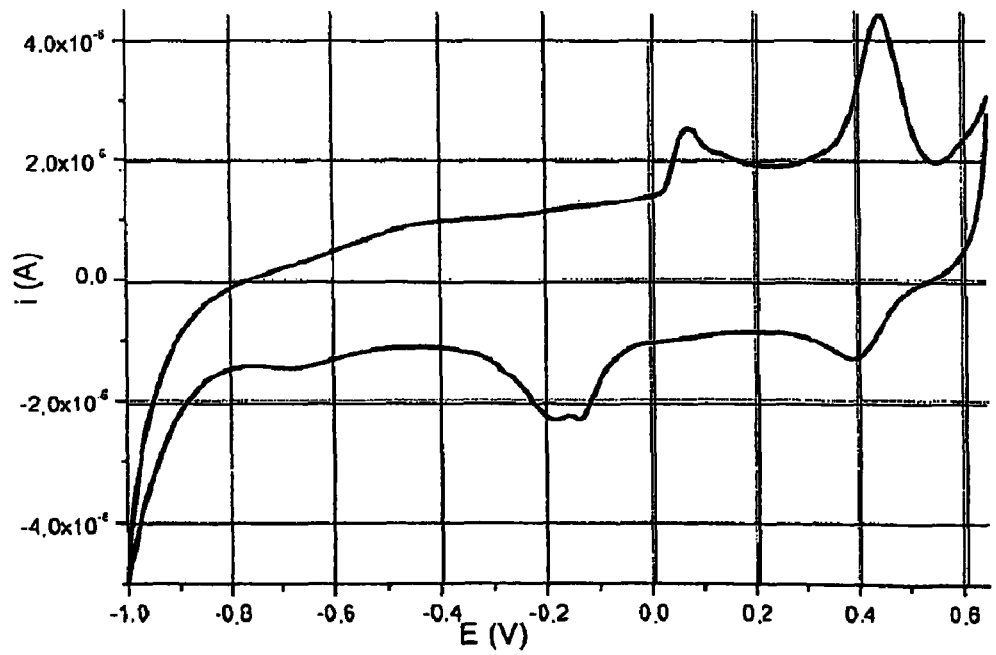

FIG. 3 Voltammogram of a polypyrrole film functionalized by a zinc tri-cationic porphyrin after 12 h in a buffer solution.

Figure 4:
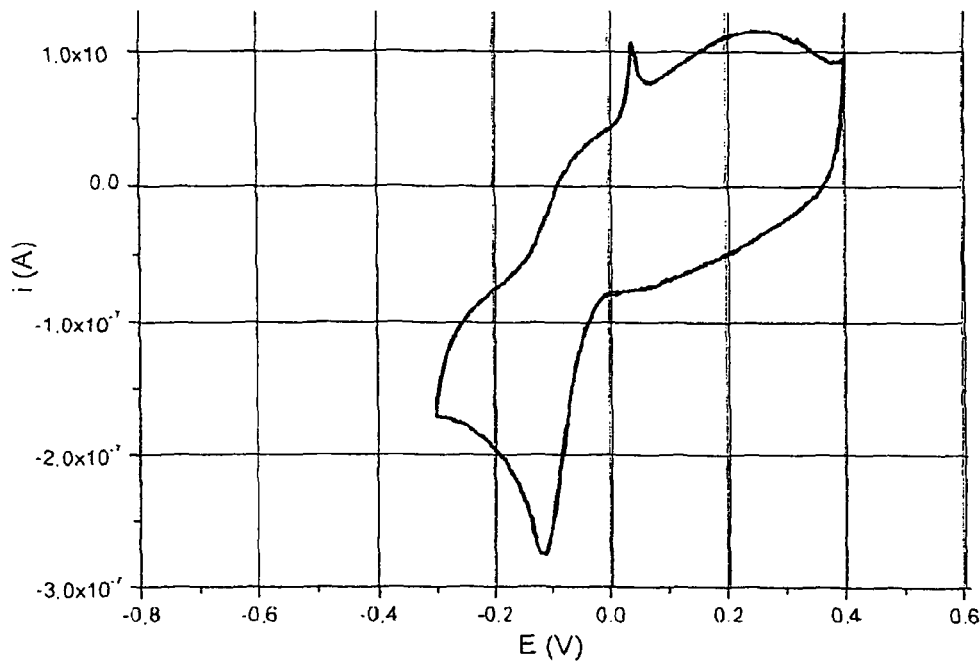

FIG. 4 Voltammogram of a polypyrrole film functionalized by a cobalt tri-cationic porphyrin.

Figure 5:
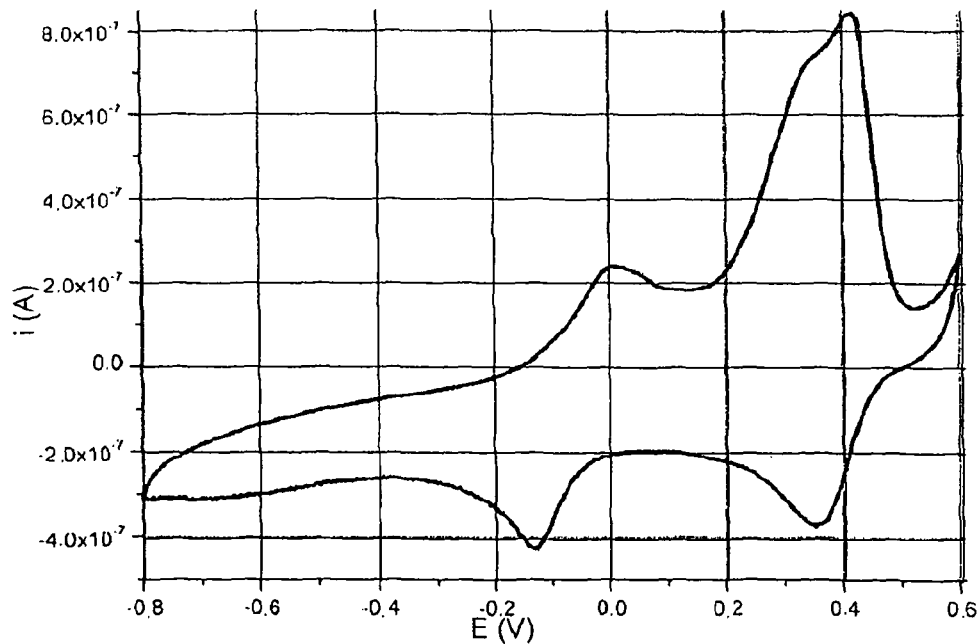

FIG. 5 Voltammogram of a polypyrrole film functionalized by a cobalt tri-cationic porphyrin after 12 h in a buffer solution.

Figure 6:
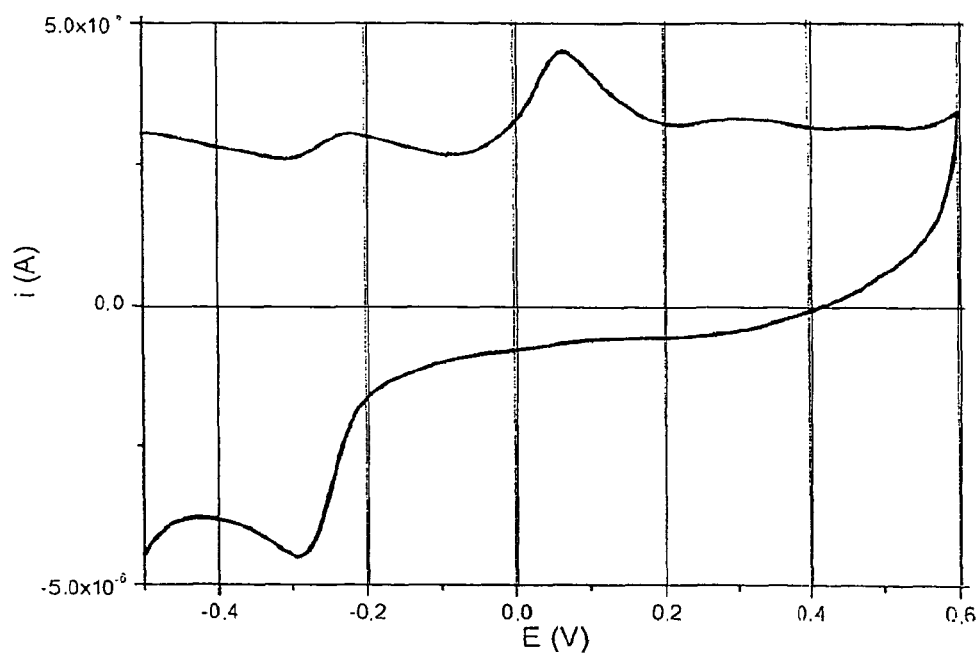

FIG. 6 Voltammogram of a polypyrrole film functionalized by a manganese tri-cationic porphyrin.

Figure 7:
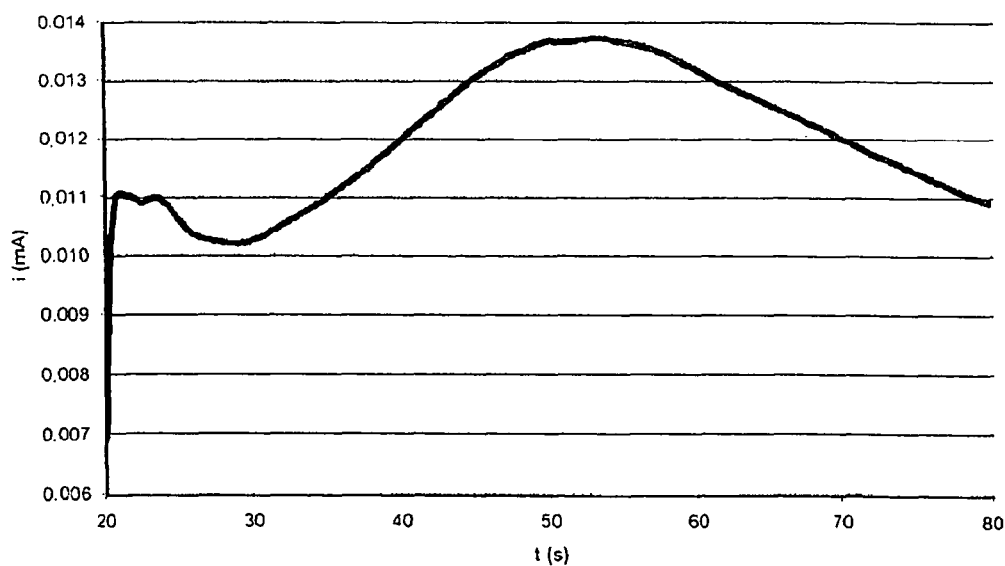

FIG. 7 Copolymerization with the cobalt porphyrin at 0.7 V.

Figure 8:
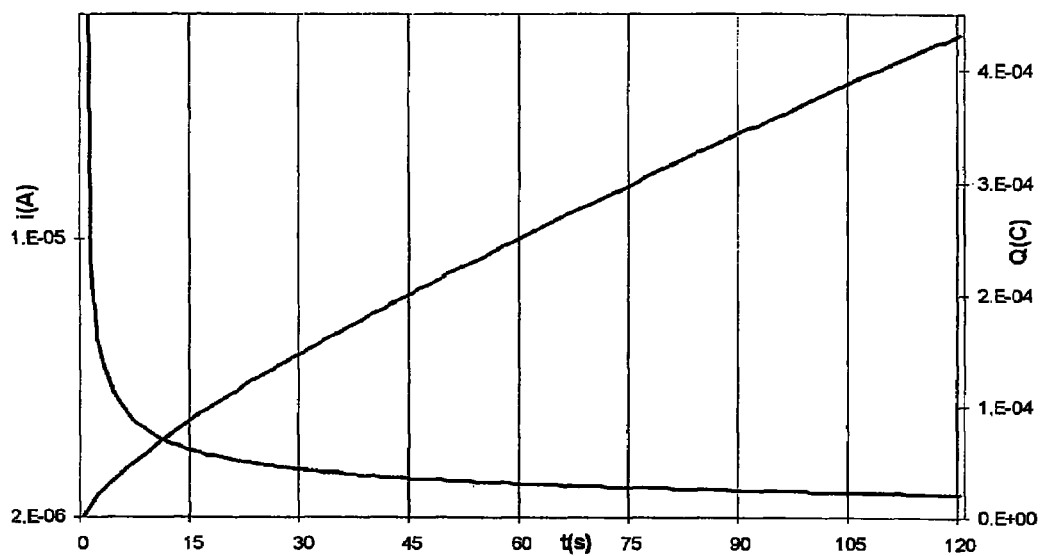
Figure 9:
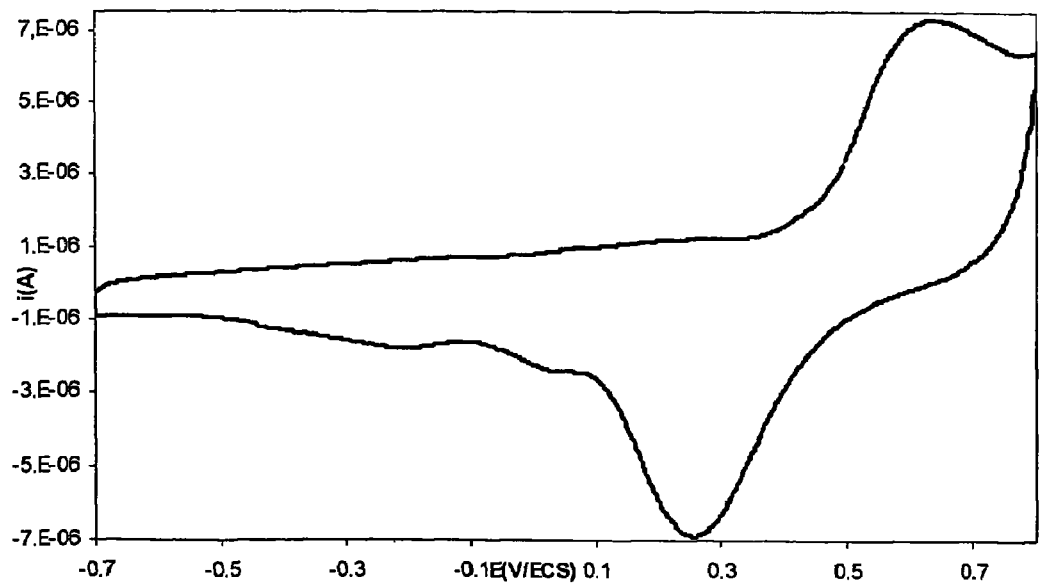

FIG. 8: Polymerization of the pyrrole monomer functionalized with the zinc diacid porphyrin at 900 mV/ECS FIG. 9: Voltammogram of a polypyrrole film functionalized by a zinc diacid porphyrin

I—Porphyrins Substituted on the Four Meso Positions by Pyridinium Groups and Complexed by Various Metals This electrochemical analysis is conducted in an aqueous medium in the presence of 0.5M NaCl and FIG. 1 shows the voltammograms obtained. It appears that, depending on the chemical nature of the metal, the redox potential varies strongly over a wide range of potentials ranging from −0.9 V/ECS to +0.9 V/ECS. It is therefore possible to modulate the electroactivity of the porphyrin, in relation to the metal used, over a wide range of potentials which corresponds to approximately 2V since, depending on the chosen complexing metal, the redox potentials are extremely different.

II—Electrochemical Analyses of Carried Tri-Cationic Porphyrins

Electrochemical analyses are firstly conducted on platinum macro-electrodes, 1 cm in diameter. Different polymerization tests are conducted at a fixed potential of 0.9V with zinc, cobalt and manganese porphyrins of formula (10):

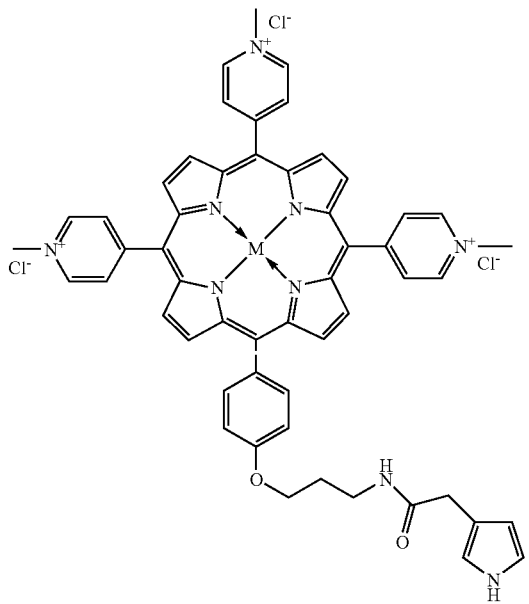

(10)

in a 0.5M aqueous solution of sodium chloride. The deposited films are analyzed by cyclic voltammetry in a 0.5M aqueous solution of sodium chloride.

II-1 Zinc Porphyrin

A potential of 0.9V is applied for 30 min to an aqueous 0.5M sodium chloride solution and 3 mM zinc monomer-metalloporphyrin. The charge is 20 mC. The deposited film is analyzed by cyclic voltammetry in a 0.5M aqueous sodium chloride solution (FIG. 2). Analysis of the film shows a reversible redox pair whose oxidation potential is +0.05V and the reduction potential is −0.12V.

Next, the film is left to soak 12 hours in an aqueous solution to test its stability, then analyzed by cyclic voltammetry in a 0.5M aqueous sodium chloride solution (FIG. 3). Analysis of the film shows the presence of the redox system related to the polypyrrole at the same potentials as previously, i.e. at an oxidation potential of +0.08V and a reduction potential of −0.13V. A second reversible redox pair is observed with an oxidation potential of +0.45V and a reduction potential of +0.40V.

II-2 Cobalt Porphyrin

A potential of 0.9V is applied for 30 min to a 0.5M aqueous solution of sodium chloride and 12 mM cobalt monomer-metalloporphyrin of formula (10). The deposited charge is 325 mC. The deposited film is analyzed by cyclic voltammetry in a 0.5M aqueous sodium chloride solution (FIG. 4). Analysis of the film shows a reversible redox pair whose oxidation potential is +0.05V and the reduction potential is −0.12V, which corresponds to the polypyrrole system.

The film is subsequently left to soak in an aqueous solution to test its stability, and is then analyzed by cyclic voltammetry in a 0.5M aqueous sodium chloride solution (FIG. 5). Analysis of the film shows the reversible redox pair of the polypyrrole whose oxidation potential is +0.01V and the reduction potential −0.13V, with improved electroactivity after hydration. Analysis of the film also shows the electrochemical signal of cobalt porphyrin whose oxidation potential is +0.42V and the reduction potential +0.35V. It is also possible to make out the two systems Co(I)/Co(II) and Co(II)/Co(III) under the oxidation wave at +0.42V.

II-3 Manganese Porphyrin

A potential of 0.9V is applied for 30 min to a 0.5M aqueous solution of sodium chloride and 4 mM manganese monomer-metalloporphyrin of formula (10). The deposited charge is 40 mC. The deposited film is analyzed by cyclic voltammetry in a 0.5M aqueous sodium chloride solution (FIG. 6). Analysis of the film shows the electrochemical signal of the polypyrrole whose oxidation potential is +0.07. Analysis of the film also shows the reversible redox pair of the manganese porphyrin whose oxidation potential is −0.22V and the reduction potential −0.29V.

II-4 Study on Chips

The cobalt porphyrin of formula (10), in a 50 mM solution, is copolymerized at a fixed potential of 0.7V in the presence of 3-(hydroxyethyl)pyrrole, in a 50 mM solution (FIG. 7). Polymerization tests and analyses are conducted on chips with carbon electrodes consisting of eight pads, with a solution of 400 mM sodium chloride and 100 mM lithium perchlorate. Several polymerization waves are observed. The polymerization curve shown FIG. 7 shows that the copolymer is deposited on the electrode.

II-5 Electropolymerisation of a Di-Anionic Porphyrin Functionalized with a Pyrrole (20)-Zn An aqueous solution of pyrrole monomer functionalized with the zinc diacid porphyrin (20)-Zn is obtained with an approximate concentration of 2 mM. The monomer is electropolymerized by applying a fixed potential of 900 mV/ECS in an aqueous monomer solution containing 500 mM NaCl and sodium hydroxide, using a 7 mm$^2$ platinum electrode. The polymerization curve is shown FIG. 8.

The final charge deposited on the surface of the platinum electrode is 6 mC·cm$^{-2}$. Analysis of this surface (FIG. 9) is then conducted in an aqueous solution without monomer containing 0.5M NaCl (scan rate 100 mV/s). The voltammogram given FIG. 9 shows two waves at 644 mV/ECS and at 257 mV/ECS corresponding to oxido-reduction of the polypyrrole.

The invention claimed is:

1. Electropolymerizable monomer, intended to be polymerized in an aqueous solution, comprising:
  an electropolymerizable unit chosen from among acetylene, pyrroles, thiophenes, indoles, anilines, azines, p-phenylenevinylenes, p-phenylenes, pyrenes, furanes, selenophenes, pyrridazines, carbazoles, acrylates, methacrylates and their derivatives, and
  a metalloporphyrin substituted by at least two different entities ionized or ionizable in an aqueous solution, wherein the metalloporphyrin, and in particular one of its meso positions, is substituted by a biological ligand, preferably chosen from among the polynucleotides, notably oligonucleotides, polypeptides, proteins, antigens, antibodies, haptenes, oligosaccharides and biotin, polynucleotides being preferred.

2. Monomer according to claim 1, characterized in that the metalloporphyrin is substituted by three entities ionized or ionizable in an aqueous solution.

3. Monomer according to claim 1, characterized in that it is soluble in distilled water, at least up to a concentration of 10 mM, preferably at least up to a concentration of 30 mM.

4. Monomer according to claim 1, characterized in that the metalloporphyrin is substituted by at least two entities ionized or ionizable in an aqueous solution, located at the meso position of the metalloporphyrin.

5. Monomer according to claim 1, characterized in that the ionized or ionizable entities comprise a function ionized or ionizable in an aqueous solution which has a pH of between 3 and 8, chosen from among the functions: ammonium, polyamine, carboxylic acid, phosphonic acid, sulfonic acid and phosphate.

6. Monomer according to claim 5, characterized in that two of the ionized or ionizable entities substituting the metalloporphyrin comprise an N-methylpyridinium group in salt form or a —COOH function.

7. Monomer according to claim 1, characterized in that two of the ionized or ionizable entities substituting the metalloporphyrin are identical.

8. Monomer according to claim 1, characterized in that the linkage between the electropolymerizable unit and the metalloporphyrin is made via a spacer arm.

9. Monomer according to claim 1, characterized in that the linkage between the electropolymerizable unit and the metalloporphyrin is made at the meso position of the metalloporphyrin.

10. Monomer according to claim 1, characterized in that the electropolymerizable unit is a pyrrole.

11. Monomer according to claim 10, characterized in that the linkage between the pyrrole and the metalloporphyrin is ensured at position 3 of the pyrrole.

12. Monomer according to claim 1, characterized in that the metalloporphyrin is also substituted by one or more electron donor or attractor groups.

13. Monomer according to claim 12, characterized in that the electron donor or attractor group(s) is (are) chosen from among: halogen atoms, cyano, nitro, $(C_1-C_4)$alkyl$(C_1-C_4)$alkenyl, $(C_1-C_4)$alkynyl and $(C_1-C_4)$alcoxy groups.

14. Monomer according to claim 1, characterized in that the metal of the metalloporphyrin is a transition metal, or Mg, Al, Sn or Ge.

15. Monomer according to claim 14, characterized in that the metal is chosen from among: Co, Ni, Mg, Fe, Zn, Mn, Pd, Cu, Pt, V, Mo, Al, Sn et Ge, Co, Zn and Mn being preferred.

16. Monomer according to claim 1, characterized in that it does not contain any biological ligand.

17. Polymerization method, characterized in that polymerization is performed by electropolymerisation in an aqueous phase from at least one monomer according to claim 1.

18. Polymerization method according to claim 17, characterized in that polymerization is copolymerization which uses at least two of the monomers in which the metal is different.

19. Polymer able to be obtained following the polymerization method defined in claim 17.

20. Monomer of formula (I):

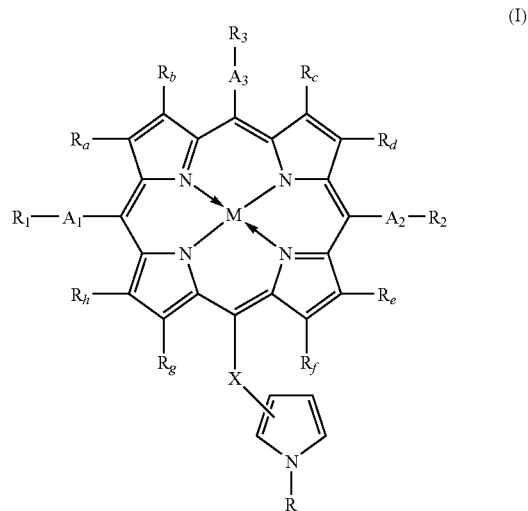

in which:
  the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group,
  $A_1$, $A_2$ and $A_3$ each independently of each other, represent a spacer arm particularly chosen from among the following chains:
    —$(CH_2)_{n1}$— wherein n1 is an integer lying in a range of 0 to 5,
    —$(CH_2$—$CH_2$—$O)_{n2}$— wherein n2 is an integer lying in a range of 1 to 5,

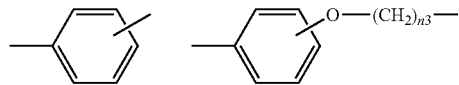

wherein n3 is an integer in a range of 1 to 5,

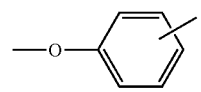

the groups $R_a$, $R_b$, $R_c$, $R_d$, $R_e$, R or $R_f$, $R_g$ and $R_h$ each independently of each other, are a hydrogen atom, an electron donor group or an electron attractor group, X is a spacer arm, notably chosen from among the following chains:

—$(CH_2)_{m1}$— wherein m1 is an integer lying in a range of 1 to 6,

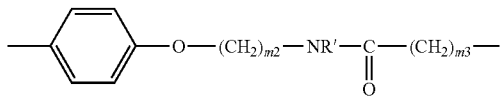

wherein m2 and m3 each independently of each other, represent an integer lying in a range of 1 to 3 and R' represents a hydrogen atom or a $(C_1$-$C_4)$alkyl group, —$(CH_2$—$CH_2$—$O)_{m4}$— wherein m4 represents an integer lying in a range of 1 to 3, a polypeptide chain comprising 1 to 3 amino acids, —$(CH{=}CH)_{m5}$— wherein m5 is an integer lying in a range of 1 to 3, M is a transition metal, or Mg, Al, Sn or Ge, and R is a hydrogen atom or a methyl, ethyl or methoxy group, characterized in that only one of groups $R_1$, $R_2$ or $R_3$, preferably $R_3$, represents a biological ligand chosen from among the polynucleotides and in particular oligonucleotides, polypeptides, proteins, antigens, antibodies, haptenes and biotin.

21. Monomer of formula (I) according to claim 20 characterized in that at least two of groups $R_1$, $R_2$ et $R_3$ each independently comprise or represent a function ionized or ionizable in an aqueous solution having a pH of between 3 and 8, chosen from among the functions: ammonium, amine, polyamine, carboxylic acid, phosphonic acid, sulfonic acid and phosphate.

22. Monomer of formula (I) according to claim 20, characterized in that at least two of groups $R_1$, $R_2$ and $R_3$, each independently, represent an amine or carboxylic acid function.

23. Monomer of formula (I) according to claim 20, characterized in that the linkage between the pyrrole and the metalloporphyrin is ensured at position 3 of the pyrrole.

24. Monomer of formula (I) according to claim 20, characterized in that R represents a hydrogen atom.

25. Monomer according to claim 20, characterized in that $R_a{=}R_b{=}R_c{=}R_d{=}R_e{=}R_f{=}R_g{=}R_h{=}H$.

26. Monomer of formula (I) according to claim 20, characterized in that at least one of groups $R_a$, $R_b$, $R_c$, $R_d$, $R_e$, $R_f$, $R_g$ and $R_h$ represents an electron donor or attractor group chosen from among: halogen atoms, cyano, nitro, $(C_1$-$C_4)$ alkyl, $(C_1$-$C_4)$alkenyl, $(C_1$-$C_4)$alkynyl and $(C_1$-$C_4)$alcoxy groups.

27. Monomer of formula (I) according to claim 20, characterized in that the metal of the metalloporphyrin is chosen from among Co, Ni, Mg, Fe, Zn, Mn, Pd, Cu, Pt, V, Mo, Al, Sn and Ge.

28. Monomer of formula (I) according to claim 27, characterized in that M is chosen from among: Co, Zn et Mn.

29. Monomer of formula (I):

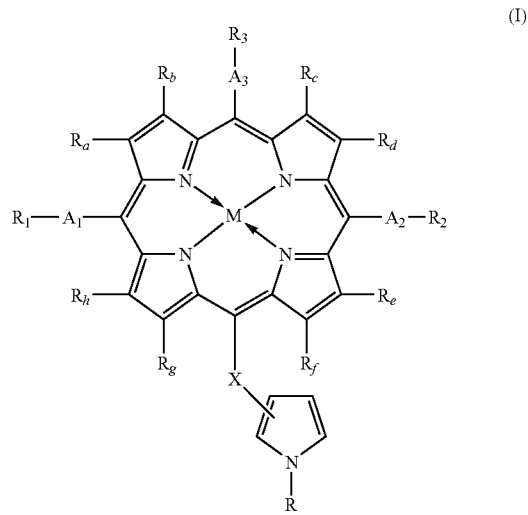

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—$(CH_2)_{n1}$— wherein n1 is an integer lying in a range of 0 to 5,

—$(CH_2$—$CH_2$—$O)_{n2}$— wherein n2 is an integer lying in a range of 1 to 5,

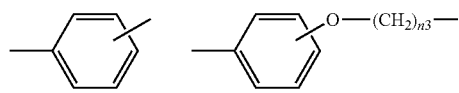

wherein n3 is an integer in a range of 1 to 5,

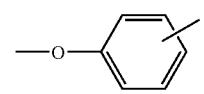

the groups $R_a$, $R_b$, $R_c$, $R_d$, $R_e$, R or $R_f$, $R_g$ and $R_h$ each independently other, are a hydrogen atom, an electron donor group or an electron attractor group, X is a spacer arm, notably chosen from among the following chains:

—$(CH_2)_{m1}$— wherein m1 is an integer lying in a range of 1 to 6,

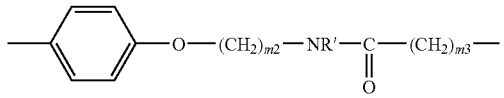

wherein m2 and m3 each independently of each other, represent an integer lying in a range of 1 to 3 and R' represents a hydrogen atom or a $(C_1$-$C_4)$alkyl group, —$(CH_2$—$CH_2$—$O)_{m4}$— wherein m4 represents an integer lying in a range of 1 to 3, a polypeptide chain comprising 1 to 3 amino acids, —$(CH{=}CH)_{m5}$— wherein m5 is an integer lying in a range of 1 to 3, M is a transition metal, or Mg, Al, Sn or Ge, and R is a hydrogen atom or a methyl, ethyl or methoxy group characterized in that at least one of groups $R_1$, $R_2$ and $R_3$ is a N-methylpyridinium in salt or —COOH form.

30. Monomer of formula (I):

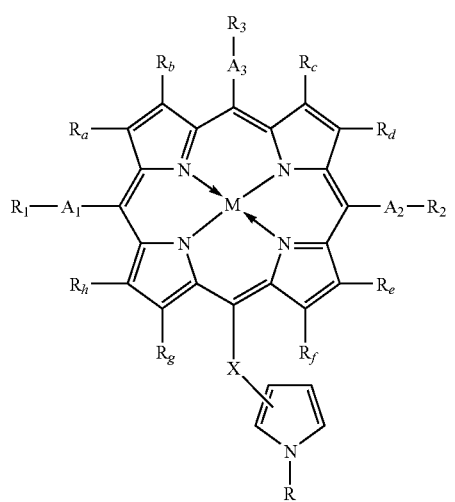

(I)

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—$(CH_2)_{n1}$— wherein n1 is an integer lying in a range of 0 to 5,

—$(CH_2$—$CH_2$—$O)_{n2}$— wherein n2 is an integer lying in a range of 1 to 5,

[phenyl and phenyl-O-(CH₂)ₙ₃— structures]

wherein n3 is an integer in a range of 1 to 5,

[—O-phenyl structure]

the groups $R_a$, $R_b$, $R_c$, $R_d$, $R_e$, R or $R_f$, $R_g$ and $R_h$ each independently of each other, are a hydrogen atom, an electron donor group or an electron attractor group, X is a spacer arm, notably chosen from among the following chains:

—$(CH_2)_{m1}$— wherein m4 is an integer lying in a range of 1 to 6,

[phenyl-O-(CH₂)m2-NR'-C(=O)-(CH₂)m3 structure]

wherein m2 and m3 each independently of each other, represent an integer lying in a range of 1 to 3 and R' represents a hydrogen atom or a $(C_1$-$C_4)$alkyl group, —$(CH_2$—$CH_2$—$O)_{m4}$— wherein m4 represents an integer lying in a range of 1 to 3, a polypeptide chain comprising 1 to 3 amino acids, —$(CH{=}CH)_{m5}$— wherein m5 is an integer lying in a range of 1 to 3, M is a transition metal, or Mg, Al, Sn or Ge, and R is a hydrogen atom or a methyl, ethyl or methoxy group characterized in that -$A_1$-$R_1$=-$A_2$-$R_2$.

31. Monomer of formula (I) according to claim 30, characterized in that -$A_1$-$R_1$=-$A_2$-$R_2$=N-methylpyridinium in salt form or:

[phenyl-COOH structure]

32. Monomer of formula (I):

(I)

[porphyrin structure as in claim 30]

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—$(CH_2)_{n1}$— wherein n1 is an integer lying in a range of 0 to 5,

—$(CH_2$—$CH_2$—$O)_{n2}$— wherein n2 is an integer lying in a range of 1 to 5,

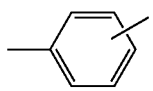 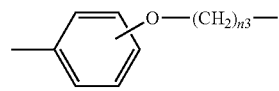

wherein n3 is an integer in a range of 1 to 5,

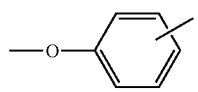

the groups $R_a$, $R_b$, $R_c$, $R_d$, $R_e$, R or $R_f$, $R_g$ and $R_h$ each independently of each other, are a hydrogen atom, an electron donor group or an electron attractor group, X is a spacer arm, notably chosen from among the following chains:

—$(CH_2)_{m1}$— wherein m1 is an integer lying in a range of 1 to 6,

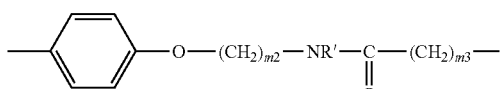

wherein m2 and m3 each independently of each other, represent an integer lying in a range of 1 to 3 and R' represents a hydrogen atom or a $(C_1\text{-}C_4)$alkyl group, —$(CH_2$—$CH_2$—$O)_{m4}$— wherein m4 represents an integer lying in a range of 1 to 3, a polypeptide chain comprising 1 to 3 amino acids, —$(CH=CH)_{m5}$- wherein m5 is an integer lying in a range of 1 to 3, M is a transition metal, or Mg, Al, Sn or Ge, and R is a hydrogen atom or a methyl, ethyl or methoxy group characterized in that -$A_3$-$R_3$ represents a group:

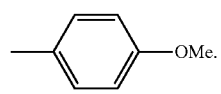

33. Monomer of formula (I):

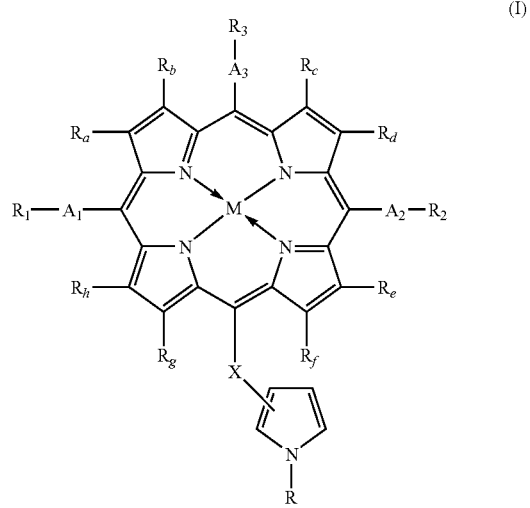

(I)

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—$(CH_2)_{n1}$— wherein n1 is an integer lying in a range of 0 to 5,

—$(CH_2$—$CH_2$—$O)_{n2}$— wherein n2 is an integer lying in a range of 1 to 5,

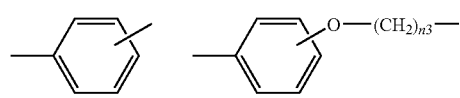

wherein n3 is an integer in a range of 1 to 5,

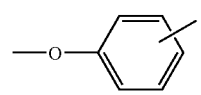

the groups $R_a$, $R_b$, $R_c$, $R_d$, $R_e$, R or $R_f$, $R_g$ and $R_h$ each independently of each other, are a hydrogen atom, an electron donor group or an electron attractor group, X is a spacer arm, notably chosen from among the following chains:

—$(CH_2)_{m1}$— wherein m1 is an integer lying in a range of 1 to 6,

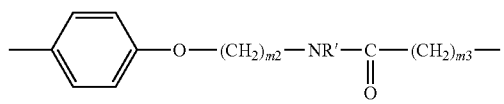

wherein m2 and m3 each independently of each other, represent an integer lying in a range of 1 to 3 and R' represents a hydrogen atom or a ($C_1$-$C_4$)alkyl group, —($CH_2$—$CH_2$—O)$_{m4}$— wherein m4 represents an integer lying in a range of 1 to 3, a polypeptide chain comprising 1 to 3 amino acids, —(CH═CH)$_{m5}$— wherein m5 is an integer lying in a range of 1 to 3, M is a transition metal, or Mg, Al, Sn or Ge, and R is a hydrogen atom or a methyl, ethyl or methoxy group characterized in that -$A_1$-$R_1$=-$A_2$-$R_2$=-$A_3$-$R_3$.

34. Monomer of formula (I) according to claim 33, characterized in that -$A_1$-$R_1$=-$A_2$-$R_2$=-$A_3$-$R_3$═N-methylpyridinium in salt form.

35. Monomer able to be obtained from a monomer of formula (I):

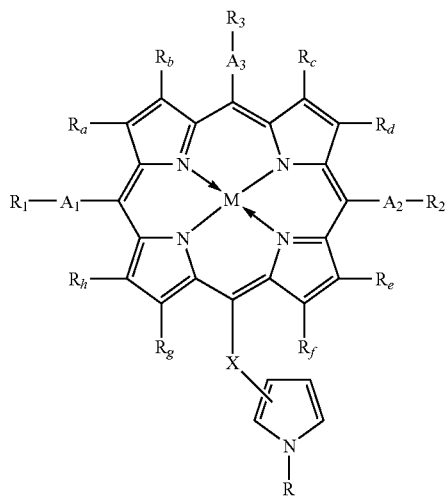

(I)

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—($CH_2$)$_{n1}$— wherein n1 is an integer lying in a range of 0 to 5,

—($CH_2$—$CH_2$—O)$_{n2}$— wherein n2 is an integer lying in a range of 1 to 5,

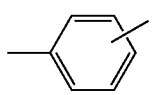 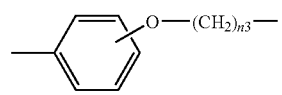

wherein n3 is an integer in a range of 1 to 5,

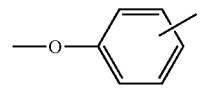

the groups $R_a$, $R_b$, $R_c$, $R_d$, $R_e$, R or $R_f$, $R_g$ and $R_h$ each independently of each other, are a hydrogen atom, an electron donor group or an electron attractor group, X is a spacer arm, notably chosen from among the following chains:

—($CH_2$)$_{m1}$— wherein m1 is an integer lying in a range of 1 to 6,

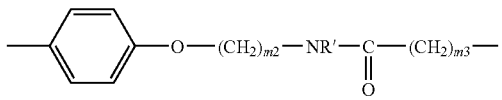

wherein m2 and m3 each independently of each other, represent an integer lying in a range of 1 to 3 and R' represents a hydrogen atom or a ($C_1$-$C_4$)alkyl group, —($CH_2$—$CH_2$—O)$_{m4}$— wherein m4 represents an integer lying in a range of 1 to 3, a polypeptide chain comprising 1 to 3 amino acids, —(CH═CH)$_{m5}$— wherein m5 is an integer lying in a range of 1 to 3, M is a transition metal, or Mg, Al, Sn or Ge, and R is a hydrogen atom or a methyl, ethyl or methoxy group characterized in that at least two of groups $R_1$, $R_2$ and $R_3$, each independently, represent an amine or carboxylic acid function by coupling, on an amine or carboxylic function present on the metalloporphyrin, a biological ligand chosen from among the polynucleotides and in particular from oligonucleotides, polypeptides, proteins, antigens, antibodies, haptenes and biotin.

36. Monomer of formula (I):

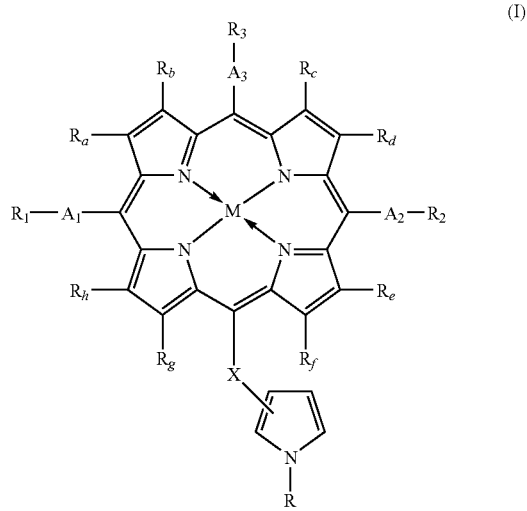

(I)

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—$(CH_2)_{n1}$— wherein n1 is an integer lying in a range of 0 to 5,

—$(CH_2$—$CH_2$—$O)_{n2}$— wherein n2 is an integer lying in a range of 1 to 5,

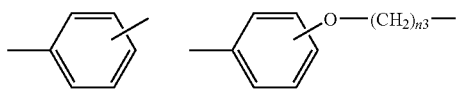

wherein n3 is an integer in a range of 1 to 5,

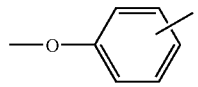

the groups $R_a$, $R_b$, $R_c$, $R_d$, $R_e$, R or $R_f$, $R_g$ and $R_h$, each independently of each other, are a hydrogen atom, an electron donor group or an electron attractor group, X is a spacer arm, notably chosen from among the following chains:

—$(CH_2)_{m1}$— wherein m1 is an integer lying in a range of 1 to 6,

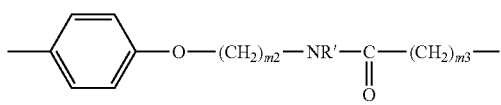

wherein m2 and m3 each independently of each other, represent an integer lying in a range of 1 to 3 and R' represents a hydrogen atom or a $(C_1$-$C_4)$alkyl group, —$(CH_2$—$CH_2$—$O)_{m4}$— wherein m4 represents an integer lying in a range of 1 to 3, a polypeptide chain comprising 1 to 3 amino acids, —$(CH=CH)_{m5}$— wherein m5 is an integer lying in a range of 1 to 3, M is a transition metal, or Mg, Al, Sn or Ge, and R is a hydrogen atom or a methyl, ethyl or methoxy group characterized in that X is a group:

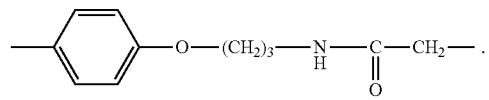

37. Monomer of formula (I):

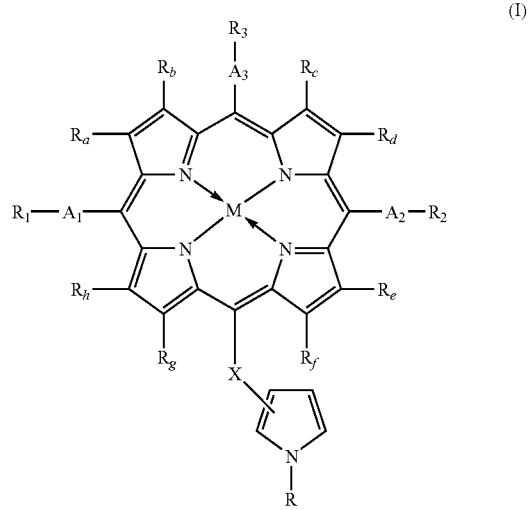

(I)

in which:

the groups $R_1$, $R_2$ et $R_3$ each independently of each other, are a hydrogen atom, a group ionized or ionizable in an aqueous solution or a biological ligand, on the understanding that at least two of groups $R_1$, $R_2$ and $R_3$, the same or different, are an ionized or ionizable group, $A_1$, $A_2$ and $A_3$ each independently of each other, represent a spacer arm particularly chosen from among the following chains:

—$(CH_2)_{n1}$— wherein n1 is an integer lying in a range of 0 to 5,

—$(CH_2$—$CH_2$—$O)_{n2}$— wherein n2 is an integer lying in a range of 1 to 5,

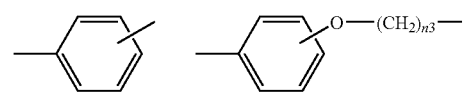

wherein n3 is an integer in a range of 1 to 5,

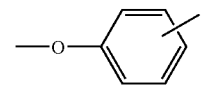

the groups $R_a$, $R_b$, $R_c$, $R_d$, $R_e$, R or $R_f$, $R_g$ and $R_h$ each independently of each other, are a hydrogen atom, an electron donor group or an electron attractor group, X is a spacer arm, notably chosen from among the following chains:

—$(CH_2)_{m1}$— wherein m1 is an integer lying in a range of 1 to 6,

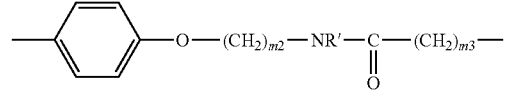

wherein m2 and m3 each independently of each other, represent an integer lying in a range of 1 to 3 and R' represents a hydrogen atom or a $(C_1-C_4)$alkyl group, —$(CH_2—CH_2—O)_{m4}$— wherein m4 represents an integer lying in a range of 1 to 3, a polypeptide chain comprising 1 to 3 amino acids, —$(CH=CH)_{m5}$— wherein m5 is an integer lying in a range of 1 to 3, M is a transition metal, or Mg, Al, Sn or Ge, and R is a hydrogen atom or a methyl, ethyl or methoxy group characterized in that it does not comprise any biological ligand.

38. In a method of producing an electrochemical by electropolymerization, the improvement comprising using at least one monomer according to claim 1 to produce the electrochemical probe by electropolymerization.

39. The method according to claim 38, characterized in that electropolymerization is conducted with the at least one monomer that carries a biological ligand.

40. Electroactive probe in the form of a conductive homopolymer able to be obtained by electropolymerization of a monomer carrying a biological ligand, the monomer, intended to be polymerized in an aqueous solution, comprising:

an electropolymerizable unit chosen from among acetylene, pyrroles, thiophenes, indoles, anilines, azines, p-phenylenevinylenes, p-phenylenes, pyrenes, furanes, selenophenes, pyrridazines, carbazoles, acrylates, methacrylates and their derivatives, and a metalloporphyrin substituted by at least two entities ionized or ionizable in an aqueous solution.

41. Electroactive probe according to claim 40, characterized in that it comprises at least two different biological ligands.

42. Electroactive probe according to claim 40, characterized in that all the monomers used have a pyrrole as electropolymerizable unit.

43. Electroactive probe according to claim 42, characterized in that copolymerization is conducted between the monomer carrying a biological ligand and a non-substituted pyrrole or a pyrrole-3-alcanol.

44. Electroactive probe according to claim 43, characterized in that copolymerization is conducted between the monomer that does not carry a biological ligand, a non-substituted pyrrole or a pyrrole-3-alcanol with a pyrrole carrying a biological ligand at position 3.

45. Method to detect at least one target ligand in a biological sample, in which the sample is contacted with an electroactive probe according to claim 40 carrying at least one probe ligand, under suitable conditions for the probe ligand/target ligand interaction, and the difference is evidenced and optionally quantified in the potential or current emitted by the probe before and after contacting with the sample.

46. Electrode comprising a conductive carrier of which all or part of the surface is coated with a probe according to claim 40.

47. Electroactive probe in the form of a conductive copolymer able to be obtained by copolymerization between at least two different monomers, at least one of the monomers carrying a biological ligand, characterized in that at least one of the monomers used is an electropolymerizable unit chosen from among acetylene, pyrroles, thiophenes, indoles, anilines, azines, p-phenylenevinylenes, p-phenylenes, pyrenes, furanes, selenophenes, pyrridazines, carbazoles, acrylates, methacrylates and their derivatives, and a metalloporphyrin substituted by at least two entities ionized or ionizable in an aqueous solution.

48. Electroactive probe according to claim 47, characterized in that at least one of the monomers used carries a biological ligand and at least one other monomer used does not carry a biological ligand.

49. Electroactive probe according to claim 47, characterized in that copolymerization uses the at least two monomers in which the metal is different.

\* \* \* \* \*